United States Patent
Zhang et al.

(10) Patent No.: US 7,838,495 B2
(45) Date of Patent: *Nov. 23, 2010

(54) COMPOSITIONS AND METHODS OF USE OF EPB1, AND ERBB3 BINDING PROTEIN

(75) Inventors: Yuexing Zhang, Ellicott City, MD (US); Anne Hamburger, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/109,600

(22) Filed: Apr. 25, 2008

(65) Prior Publication Data

US 2008/0269133 A1 Oct. 30, 2008

Related U.S. Application Data

(60) Provisional application No. 60/914,430, filed on Apr. 27, 2007.

(51) Int. Cl.
| | |
|---|---|
| *A61K 38/16* | (2006.01) |
| *A61K 31/7105* | (2006.01) |
| *A61K 31/711* | (2006.01) |
| *C07K 14/00* | (2006.01) |

(52) U.S. Cl. .............. 514/12; 514/21; 514/44; 530/350; 424/93.2

(58) Field of Classification Search ............ None
See application file for complete search history.

(56) References Cited

U.S. PATENT DOCUMENTS 6,080,728 A * 6/2000 Mixson .............. 514/44 R
7,247,700 B2 * 7/2007 Korsmeyer et al. ........ 530/300

OTHER PUBLICATIONS

NCBI information page (downloaded from the web on Sep. 28, 2009).*
Lessor et al ((Journal of Cellular Physiology, 2000, vol. 183, pp. 321-329).*
Zhang and Hamburger (British Journal of Cancer, 2005, vol. 92, pp. 140-146).*
Arlen and Gulley (Future Oncology, 2005, vol. 1, pp. 19-22).*
Iyer et al (Human Gene Therapy, Jan. 2006, vol. 17, pp. 125-132).*
Zhang et al (PNAS, 2005, vol. 102, pp. 9890-9895).*
Vargas et al (Prostate Cancer and Prostatic Diseases, 2006, vol. 9, pp. 245-253).*
Abrahamsson et al (European Urology, 2005, vol. 48, pp. 900-905).*
Zhang et al (Nucleic Acids Research, 2003, vol. 31, pp. 2168-2177).*

* cited by examiner

*Primary Examiner*—Karen A Canella
(74) *Attorney, Agent, or Firm*—Whitham, Curtis, Christofferson & Cook, P.C.

(57) ABSTRACT

Inhibition of the proliferation of hormone refractory prostate cancer cells is achieved by administering EPB1, an ErbB3 binding protein, in combination with another anti-proliferation therapy such as administration of antiandrogens, other anticancer agents, radiation therapy, or surgery. Administration of EPB1 reverses the phenotype of hormone-resistant prostate cancer cells to hormone-sensitive prostate cancer cells.

42 Claims, 17 Drawing Sheets

```
ATGTCGGGCGAGGACGAGCAACAGGAGCAAACTATCGCTGAGGACCTGGTCGTGACCAAGTATAAGATGG
GGGGCGACATCGCCAACAGGGTACTTCGGTCCTTGGTGGAAGCATCTAGCTCAGGTGTGTCGGTACTGAG
CCTGTGTGAGAAAGGTGATGCCATGATTATGGAAGAAACAGGGAAAATCTTCAAGAAAGAAAAGGAAATG
AAGAAAGGTATTGCTTTTCCCACCAGCATTTCGGTAAATAACTGTGTATGTCACTTCTCCCCTTTGAAGA
GCGACCAGGATTATATTCTCAAGGAAGGTGACTTGGTAAAAATTGACCTTGGGGTCCATGTGGATGGCTT
CATCGCTAATGTAGCTCACACTTTTGTGGTTGATGTAGCTCAGGGGACCCAAGTAACAGGGAGGAAAGCA
GATGTTATTAAGGCAGCTCACCTTTGTGCTGAAGCTGCCCTACGCCTGGTCAAACCTGGAAATCAGAACA
CACAAGTGACAGAAGCCTGGAACAAAGTTGCCCACTCATTTAACTGCACGCCAATAGAAGGTATGCTGTC
ACACCAGTTGAAGCAGCATGTCATCGATGGAGAAAAAACCATTATCCAGAATCCCACAGACCAGCAGAAG
AAGGACCATGAAAAAGCTGAATTTGAGGTACATGAAGTATATGCTGTGGATGTTCTCGTCAGCTCAGGAG
ACGGCAACGCCAAGGATGCAGGACAGAGAACCACTATTTACAAACGAGACCCCTCTAAACAGTATGGACT
GAAAATGAAAACTTCACGTGCCTTCTTCAGTGAGGTGGAAAGGCGTTTTGATGCCATGCCGTTTACTTTA
AGAGCATTTGAAGATGAGAAGAAGGCTCGGATGGGTGTGGTGGAGTGCGCCAAACATGAACTGCTGCAAC
CATTTAATGTTCTCTATGAGAAGGAGGGTGAATTTGTTGCCCAGTTTAAATTTACAGTTCTGCTCATGCC
CAATGGCCCCATGCGGATAACCAGTGGTCCCTTCGAGCCTGACCTCTACAAGTCTGAGATGGAGGTCCAG
GATGCAGAGCTAAAGGCCCTCCTCCAGAGTTCTGCAAGTCGAAAAACCCAGAAAAAGAAAAAAAAGAAGG
CCTCCAAGACTGCAGAGAATGCCACCAGTGGGGAAACATTAGAAGAAAATGAAGCTGGGGACTGA
```

Figure 1

```
          10         20         30         40         50         60
MSGEDEQQEQ TIAEDLVVTK YKMGGDIANR VLRSLVEASS SGVSVLSLCE KGDAMIMEET 70         80         90        100        110        120
GKIFKKEKEM KKGIAFPTSI SVNNCVCHFS PLKSDQDYIL KEGDLVKIDL GVHVDGFIAN 130        140        150        160        170        180
VAHTFVVDVA QGTQVTGRKA DVIKAAHLCA EAALRLVKPG NQNTQVTEAW NKVAHSFNCT 190        200        210        220        230        240
PIEGMLSHQL KQHVIDGEKT IIQNPTDQQK KDHEKAEFEV HEVYAVDVLV SSGEGKAKDA 250        260        270        280        290        300
GQRTTIYKRD PSKQYGLKMK TSRAFFSEVE RRFDAMPFTL RAFEDEKKAR MGVVECAKHE 310        320        330        340        350        360
LLQPFNVLYE KEGEFVAQFK FTVLLMPNGP MRITSGPFEP DLYKSEMEVQ DAELKALLQS 370        380        390
SASRKTQKKK KKKASKTAEN ATSGETLEEN EAGD
```

Figure 2

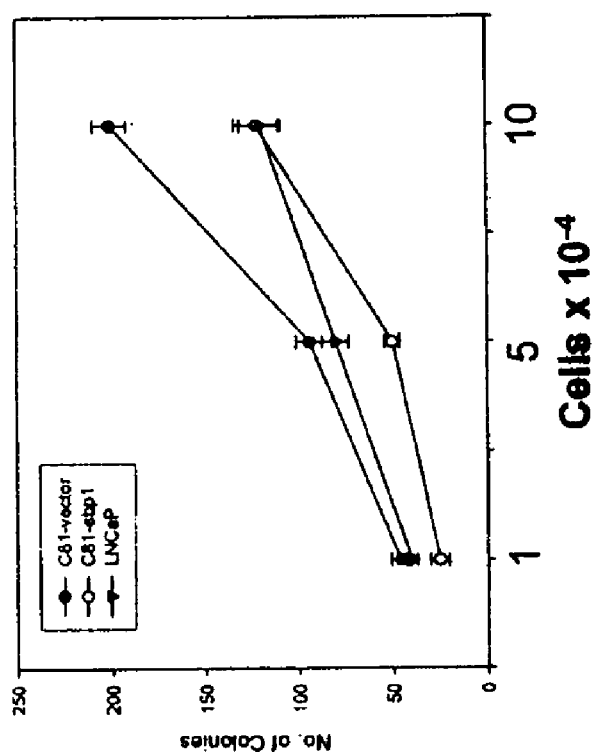
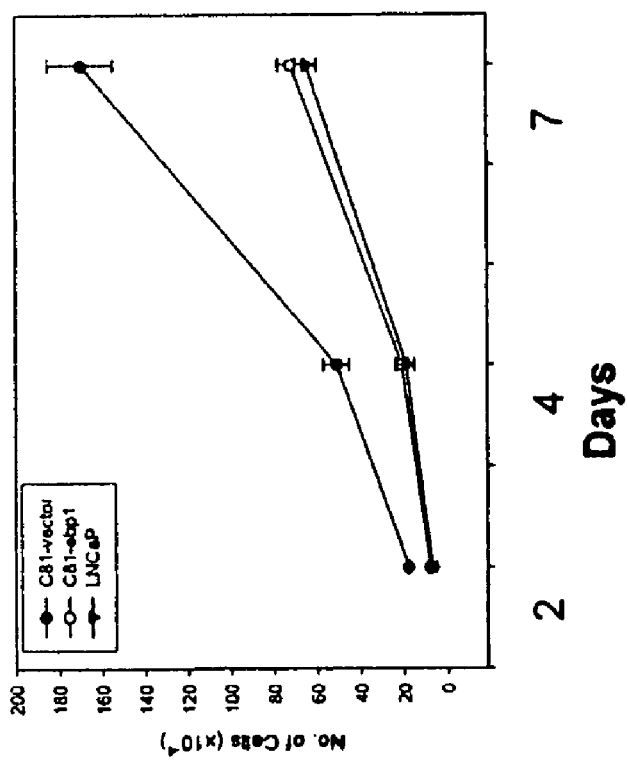
*Figure 4A*

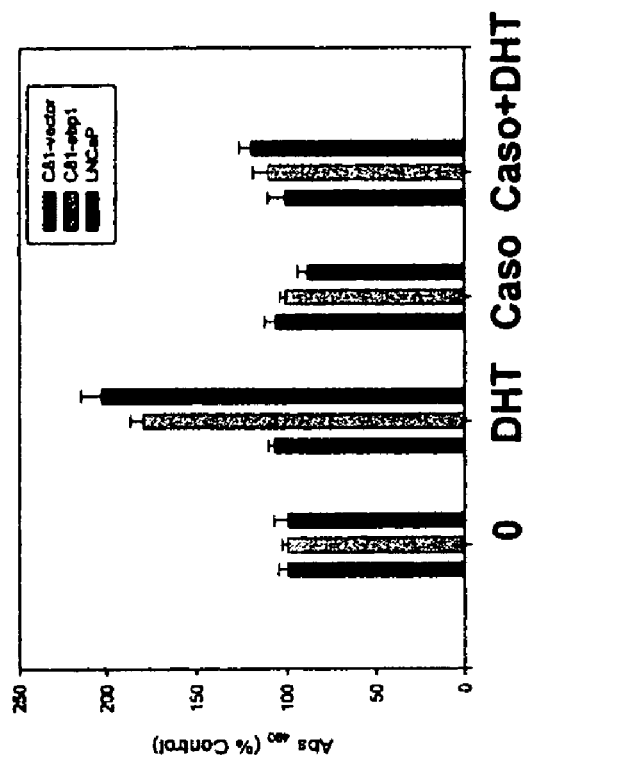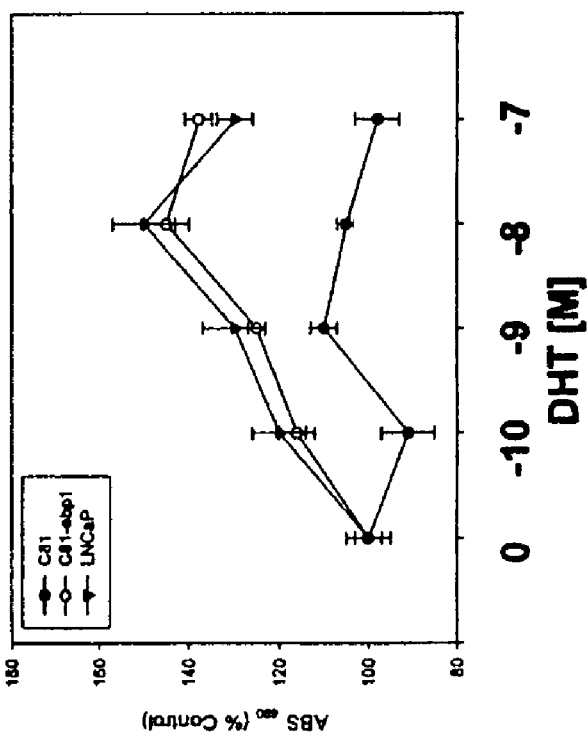
Figure 4B

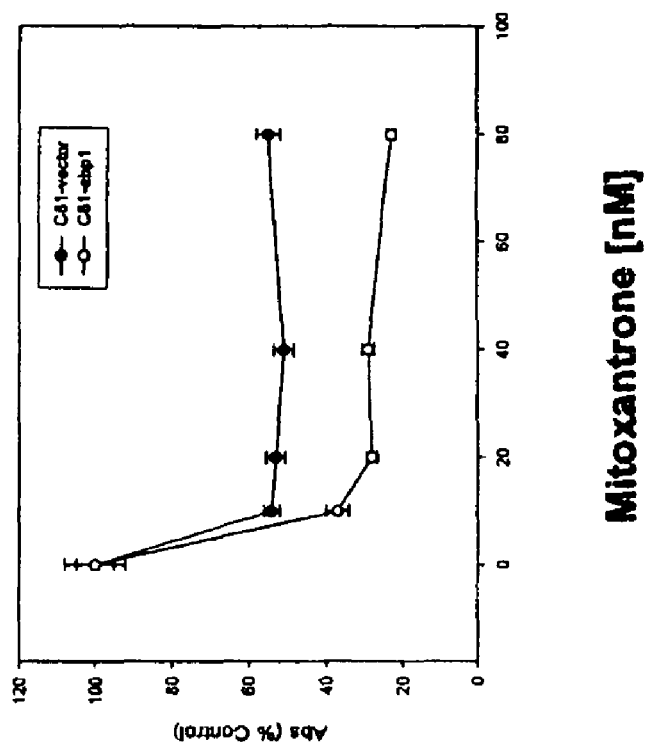
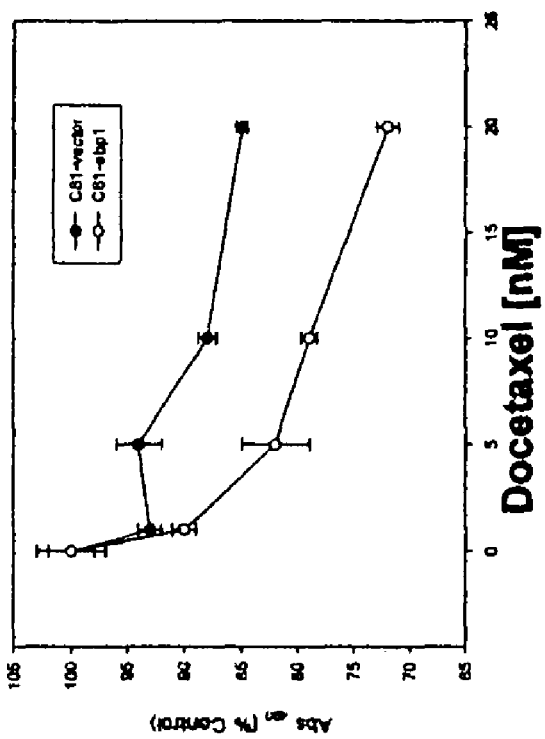
*Figure 4C*

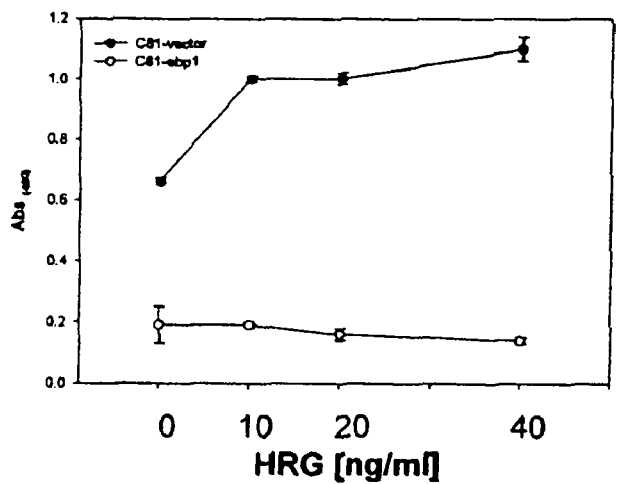
*Figure 6A*
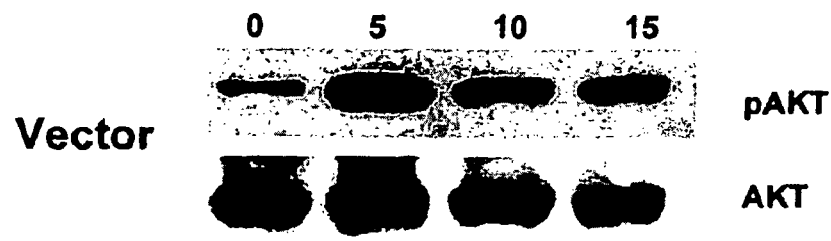
*Figure 6B*
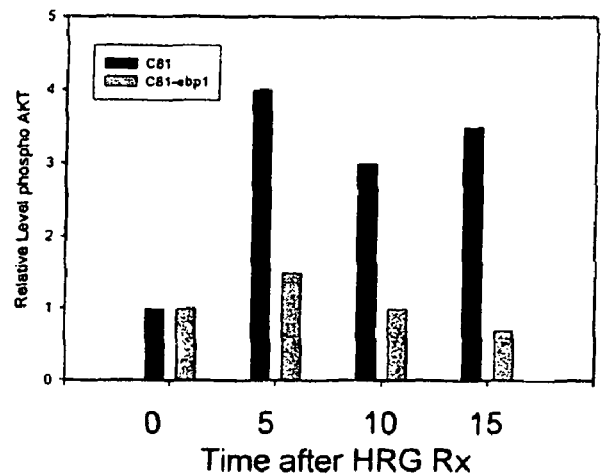
*Figure 6C*

*Figure 7A*
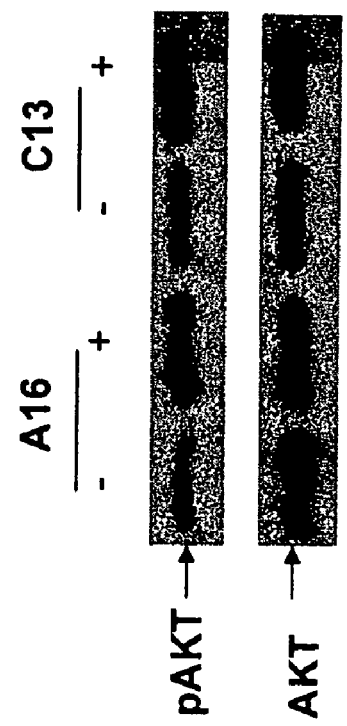
*Figure 7B*
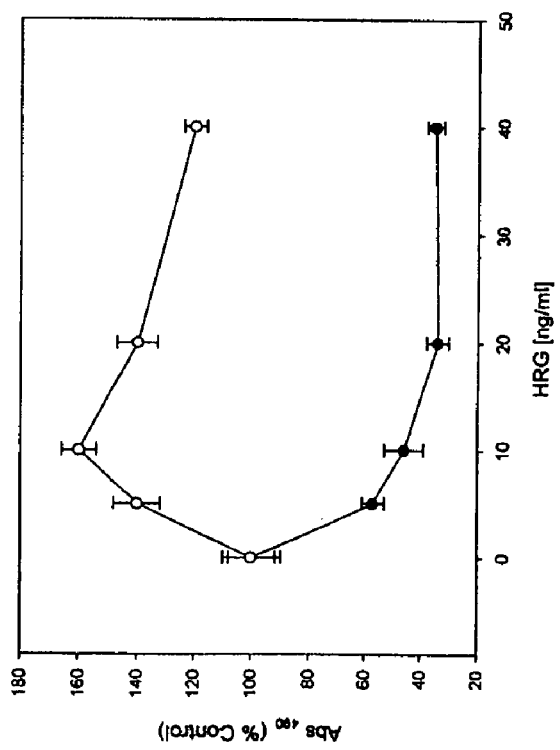

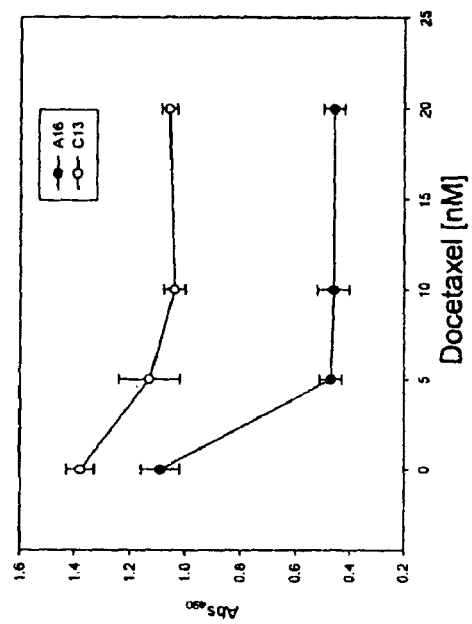
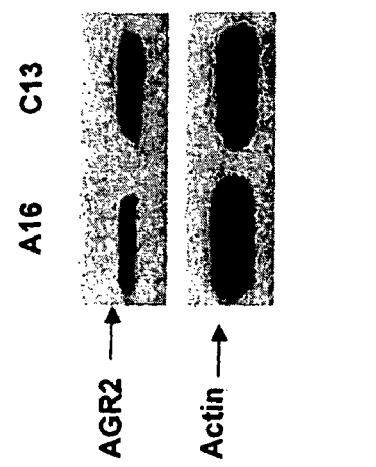
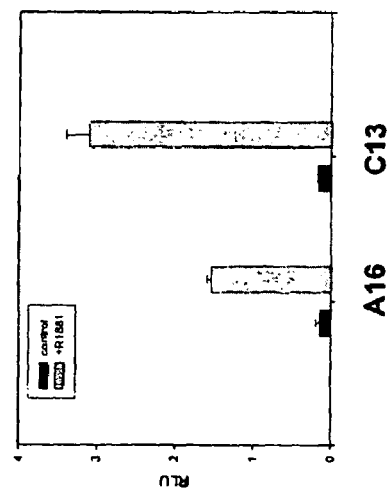
*Figure 7C*

Figure 9A
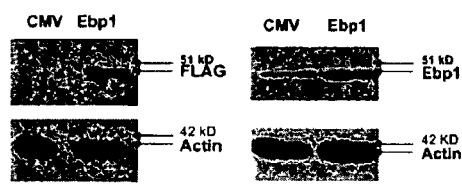
Figure 9B
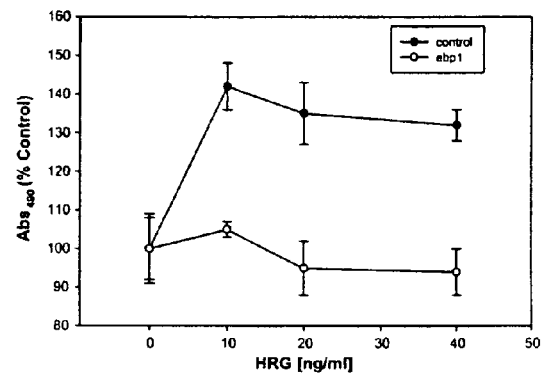
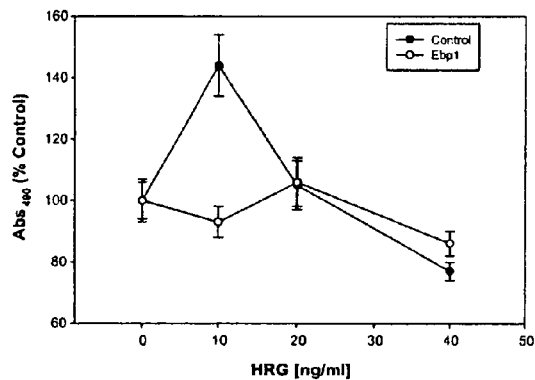
Figure 9C
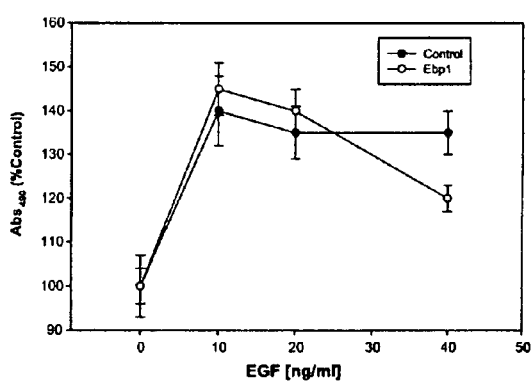
Figure 9D

Figure 10A
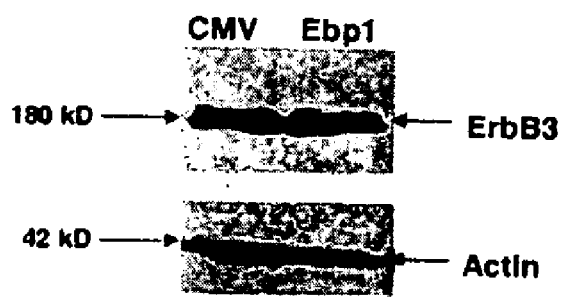
Figure 10B
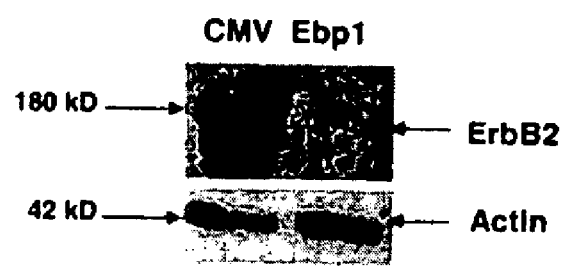
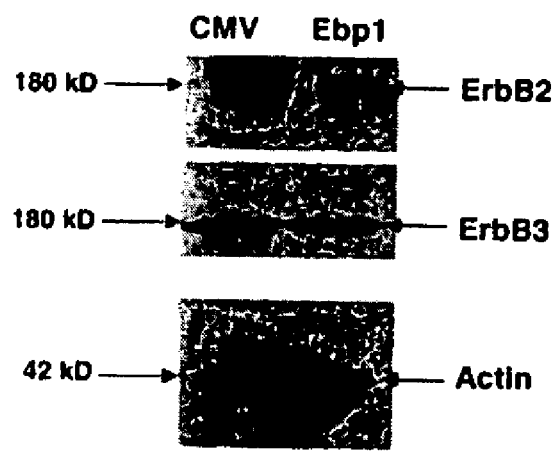
Figure 10C

Figure 12A
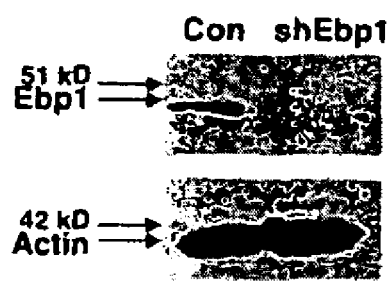
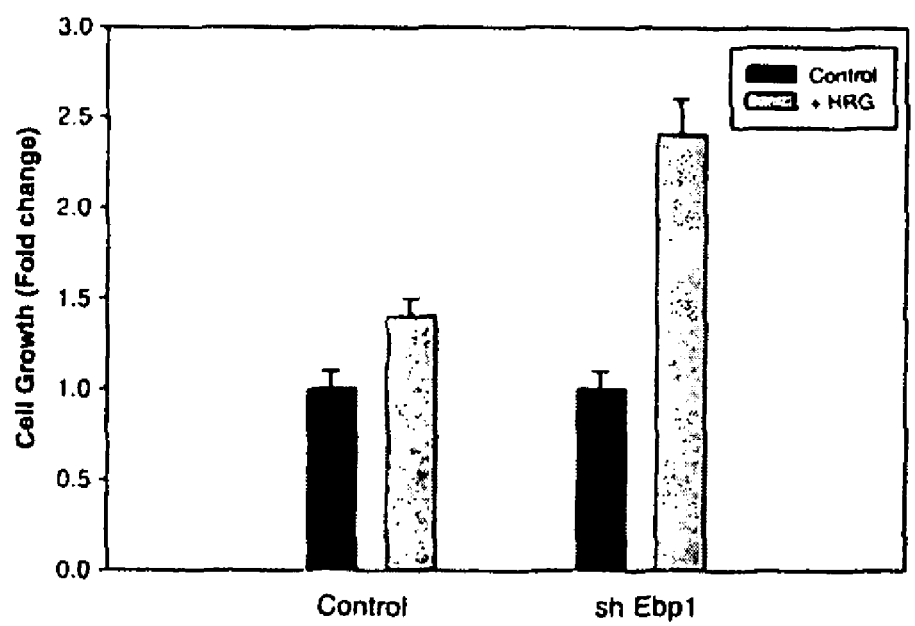
Figure 12B

COMPOSITIONS AND METHODS OF USE OF EPB1, AND ERBB3 BINDING PROTEIN

CROSS-REFERENCE TO RELATED APPLICATIONS

This application claims benefit of U.S. provisional patent application 60/914,430, filed Apr. 27, 2007, the complete contents of which is hereby incorporated by reference.

STATEMENT OF FEDERALLY SPONSORED RESEARCH AND DEVELOPMENT

This invention was made, in part, with government support under Grant Nos. NIH R01 CA076047 and R21 CA088882 awarded by the National Institutes of Health, and DOD W81XWH-07-1-0267 awarded by the Department of Defense. The government has certain rights in the invention.

SEQUENCE LISTING

This application includes as the Sequence Listing the complete contents of the accompanying text file "Sequence.txt", created Apr. 24, 2008, containing 4,096 bytes, hereby incorporated by reference.

FIELD OF THE INVENTION

The present invention relates to compositions and methods for administering and expressing EPB1, an ErbB3 binding protein, in order to inhibit dysregulated cell proliferation. In particular, the invention provides compositions and methods for the administration and expression of EPB1 in order to treat cancer, especially prostate cancer.

BACKGROUND OF THE INVENTION

Prostate cancer is the second most prevalent cancer among men in the United States and ranks second to lung cancer in terms of annual mortality (Weir et al., 2003, Annual Report to the Nation on the Status of Cancer, 1975-2000, featuring the uses of surveillance data for cancer prevention and control, J. Natl. Cancer Inst., 95:1276-1299). Prostate cancer can begin as an androgen-dependent tumor that undergoes clinical regression in response to pharmacological and surgical strategies that reduce testosterone concentration can be effective in treating prostate cancer at this stage. However, despite this treatment, the cancer can eventually regrow as a lethal androgen or hormone-independent tumor (Feldman et al., 2001, The Development of Androgen-Independent Prostate Cancer, Nat. Rev. Cancer, 1:34-45).

The molecular basis for hormone-independent cancer progression is poorly understood. However, most androgen-independent prostate cancers still express androgen receptor (AR) and aberrant AR signaling is postulated to be an important mechanism of progression to androgen independence (Taplin et al., 2004, Androgen Receptor: A Key Molecule in the Progression of Prostate Cancer to Hormone Independence, J. Cell Biochem, 91:483-490). The pathways involved in AR-mediated survival of prostate cancer cells in the absence of androgens include amplification or mutation of the AR, deregulation of growth factors or cytokines, and alteration of AR coregulators. Thus, the AR is a key molecule in pathways leading to androgen independence.

Both increased sensitivity of AR to androgens and activation of AR by growth factor and/or cytokines are proposed to account for androgen-independent growth (Feldman et al., 2001, The Development of Androgen-Independent Prostate Cancer, Nat. Rev. Cancer, 1:34-45). Clinically, upregulation of the AR has been recently demonstrated to be consistently associated with hormone-independent disease (Edwards et al., 2003, Androgen Receptor Gene Amplification and Protein Expression in Hormone Refractory Prostate Cancer, Br. J. Cancer, 89:552-556) (Taplin et al., 1995, Mutation of the Androgen-Receptor Gene in Metastatic Androgen-Independent Prostate Cancer, N. Engl. J. Med., 332:1393-1398). In a xenograft model, Chen et al. (Chen et al., 2004, Molecular Determinants of Resistance to Antiandrogen Therapy, Nat. Med. 10:33-39) recently reported that a two- to five-fold increase in AR mRNA was the only change consistently associated with the development of androgen resistance. As a result, cells exhibit an increased sensitivity to low levels of androgen. In addition, androgen receptor antagonists are converted to agonists.

Thus, inhibition of AR expression is key to the design of new agents effective for treatment of prostate cancer (Isaacs et al., 2004, Androgen Receptor Outwits Prostate Cancer Drugs, Nat. Med., 10:26-27). Strategies that target the AR include the use of RNA interference, ribozymes, and antisense molecules to decrease AR mRNA (Eder et al., 2002, Inhibition of LNCaP Prostate Tumor Growth In Vivo by an Antisense Oligonucleotide Directed Against the Human Androgen Receptor, Cancer Gene Ther., 9:117-125) (Zegarra-Moro et al., 2002, Disruption of Androgen Receptor Function Inhibits Proliferation of Androgen-Refractory Prostate Cancer Cells, Cancer Res., 62:1008-1013), heat shock protein 90 inhibitors, such as 17 AAG, to destabilize AR protein (Solit et al., 2002, 17-Allylamino-17-Demethoxygeldanamycin Induces the Degradation of Androgen Receptor and HER-2/neu and Inhibits the Growth of Prostate Cancer Xenografts, Clin. Cancer Res., 8:986-993), and pharmacological inhibitors of AR protein synthesis or function (Mitchell et al., 1999, Resveratrol Inhibits the Expression and Function of the Androgen Receptor in LNCaP Prostate Cancer Cells, Cancer Res., 59:5892-5895) (Zhu et al., 2001, Silymarin Inhibits Function of the Androgen Receptor by Reducing Nuclear Localization of the Receptor in the Human Prostate Cancer Cell Line LNCaP, Carcinogenesis, 22:1399-1403). However, the manipulation of endogenous AR corepressors to downregulate AR function has not yet been reported. Androgen receptor antagonists used in the treatment of prostate cancer cause recruitment of corepressor complexes to the AR, which underlies their inhibitory activity. Shang et al. (Shang et al., 2002, Formation of the Androgen Receptor Transcription Complex, Mol. Cell, 9:601-610) have demonstrated that the androgen antagonist bicalutamide recruits the repressors NCoR and SMRT to the AR bound to the prostate specific antigen (PSA) promoter. Chen et al. (Chen et al., 2004, Molecular Determinants of Resistance to Antiandrogen Therapy, Nat. Med., 10:33-39) demonstrated that increases in AR protein levels lead to a decrease in corepressor recruitment to AR-regulated promoters after bicalutamide treatment. Conceivably, the lack of association of AR with inhibitory coregulators might contribute to the increased AR transactivation potency in prostate cancer. The clinical resistance of these agents may reflect a failure of corepressor recruitment to the AR.

Another potential approach toward prostate cancer is gene therapy. Intraprostatic injection has been proposed as a minimally invasive technique to deliver gene therapy that could be readily performed by urologists or radiologists. The unsolved issue is to identify genes that would be efficacious for therapy. The most extensively studied gene therapeutic approach to date for prostate cancer is suicide gene therapy, typically involving the tumor-targeted delivery of genes encoding metabolic enzymes that convert systemically delivered, relatively innocuous prodrugs into highly toxic metabolites. However, the effectiveness of these strategies for human prostate cancer may be blunted because of their limited effect on slowly dividing prostate cells that require long term administration of prodrugs to increase the proportion of cells affected. Furthermore, these genes can be inhibited by anti-apoptotic proteins like Bcl-2 family members, which have been shown to be upregulated in progressive, hormone-independent prostate cancer.

The prior art has thus far failed to provide successful methods of treatment for cancers such as prostate cancer, particularly for the hormone independent prostate cancer.

BRIEF SUMMARY OF THE INVENTION

The present invention is predicated on the discovery that when EPB1, an ErbB3 binding protein, is expressed within androgen-independent prostate cancer cells, the cells are converted to an androgen-dependent (i.e. androgen-sensitive) phenotype. This is important because conversion to androgen-sensitivity renders the prostate cancer cells susceptible to anti-androgen therapy. Anti-androgen therapy is known to be highly effective in promoting cessation of uncontrolled growth of androgen-sensitive tumors.

The present invention provides compositions and methods for the administration of EPB1. While in one embodiment, such compositions and methods are used to treat prostate cancer, those of skill in the art will recognize that other types of cancers may also be treated in this manner. Without being bound by theory, it is believed that Epb1 acts within cells to repress the activity of cell-cycle genes whose unregulated activity results in hyperproliferation, i.e. uncontrolled, unregulated growth, which is the hallmark of cancer. Thus, any cancer cell in which administration of Epb1 protein inhibits ungoverned, abnormal and/or pathological activity of cell-cycle genes of the cancer cell, may be treated by the methods and compositions of the invention. For example, when administered to a cancer cell that contains androgen receptors (ARs), EPB1 binds to the ARs and attenuates or modifies their activity, resulting in repression of the cell-cycle genes of the cancer cell. As demonstrated in the exemplary treatment of androgen-refractory prostate cancer cells described herein, administration of EPB1 results in, for example, a change of phenotype from androgen-independent to androgen-dependent, a decrease in tumor volume, and an increased sensitivity to the effects of a variety of an antiproliferation therapy. In some embodiments of the invention, Epb1 is administered by gene therapy, i.e. a vector containing nucleic acid sequences that encode Epb1 is introduced into the cancer cells, and the protein is expressed within the cancer cell. In other embodiments the invention is administered as a protein therapy

BRIEF DESCRIPTION OF THE DRAWINGS

FIG. 1. The nucleotide sequence (SEQ ID NO: 1) of EPB1 (GenBank Accession No. NM-006191).

FIG. 2. The amino acid sequence (SEQ ID NO: 2) of EPB1 (GenBank Accession No. NM-006191).

FIG. 4A-C. EBP1 restoration ameliorates the hormone refractory phenotype A. (Left panel) Growth in monolayer culture. Equal numbers ($5 \times 10^4$) of vector or EBP1 stably transfected cells were plated at Day 0 in complete media and viable cell numbers determined at the indicated times. Each point represents mean±S.E. of 3 wells. Representative of 3 experiments (Right panel). Colony growth in soft agar. C81 cells stably transfected with either pcDNA or EBP1 were plated in soft agar at the cell densities indicated and colony numbers assessed at Day 10. Each point represents mean±S.E. of 3 dishes. Data is representative of 3 experiments. B. (Left Panel) Response of EBP1 and vector transfected C81 cells to dihydrotestosterone (DHT). EBP1 and vector control C81 transfected cells and early passage LNCaP cells were plated in complete media at $5 \times 10^3$ cells/well in 96 well plates for one day. The next day, cells were switched to steroid reduced medium for two days as described in the Materials and Methods. DHT was then added at the indicated concentrations. Cells were refed media every 3 days. Total cell numbers were determined seven days later by MTT assays. Each point represents mean±S.E. of 6 wells. Data is representative of two experiments. (Right Panel) Effect of Bicalutamide on DHT stimulated growth. Cells were plated as described in the Materials and Methods. After 2 days in steroid reduced medium, cells were fed with fresh steroid reduced medium with or without 10 μM bicalutamide (Casodex) in the presence or absence of 10 nM DHT. Total cell numbers were assessed 7 days later by MTT assay. Cells were refed media every 3 days. The data shown are mean±S.E. of six wells. Similar results were found in 2 independent experiments. C. EBP1 expression sensitizes C81 cells to chemotherapeutic drugs. C81 vector control or EBP1 transfectants were plated in 96 well plates in complete media and allowed to attach overnight. The cells were then placed in steroid reduced media for two days and then refed with steroid reduced media in the presence of the indicated concentrations of Docetaxel (left panel) or Mitoxantrone (right panic). Total cell numbers were determined by MTT assays 5 days later. Each point represents mean±S.E. of 6 wells. Data is representative of two experiments.

FIG. 6A-C. EBP1 overexpression inhibits the response to HRG A. EBP1 and vector control transfected cells were plated in complete media at $5 \times 10^3$ cells/well for one day. The next day, cells were switched to steroid reduced-media and HRG added at the indicated concentrations. Total cell numbers were determined seven days later by MTT assay. Each point represents mean±S.E. of 6 wells. Data is representative of three experiments. B. AKT activation in response to HRG C81-EBP1 or vector control cells were serum starved overnight and then treated with HRG (20 ng/ml) for the indicated times (mm). Cell lysates were immunoblotted with antibody to phospho-AKT or total AKT as indicated. C. Densitometric evaluation of AKT phosphorylation. Data is representative of two independent experiments.

FIG. 7A-C. Suppression of EBP1 by shRNA promotes a hormone refractory phenotype A. Western blot analysis of Ebp1. Lysates of LNCaP cells stably transduced with a control lentivirus (A16) or an EBP1 targeted shRNA (13C) were collected and resolved by SDS-PAGE. Western blots were probed for endogenous EBP1 or ACTIN as indicated. B. Inhibition of EBP1 expression abrogates the ability of HRG to arrest growth (Left panel) Control and shRNA EBP1 targeted cells were plated in complete media at $5 \times 10^7$ cells/well for one day. The next day, cells were switched to steroid reduced-media and HRG added at the indicated concentrations. Total cell numbers were determined seven days later by MTT assay. Each point represents mean±S.E. of 6 wells. Data is representative of three experiments. (Right Panel) AKT phosphorylation in EBP1 knock out cells Control (A16) or EBP 1 knock out cells (C13) were treated with HRG (20 ng/ml) for 15 mm and cell lysates assessed for the presence of phospho and total AKT as indicated. C. (Left panel) Elimination of EBP1 expression enhances the activity of an AR regulated promoter A 16 or C 13 cells were transfected with an MMTV-luciferase reporter plasmid. Twenty-four hours after transfection, cells were switched to phenol-red free RPMI 1640 media with 1% CSS containing R1881 ($10^{-8}$M) or vehicle control. Sixteen hours later, luciferase activity was measured. Each point represents mean±S.E. of triplicate wells, Representative of 3 experiments. (Middle Panel) AGR2 is over expressed in C13 LNCaP cells that do not express EBP1. Lysates of logarithmically growing A16 and C13 cells were resolved by SDS-PAGE and analyzed by Western blotting using antibodies to AGR2 and ACTIN as indicated. (Right Panel). Elimination of EBP1 expression affects the response to Docetaxel. C13 or A16 cells were plated in 96 well plates in complete media and allowed to attach overnight. The cells were then placed in steroid reduced media for two days and then refed with steroid reduced media in the presence of the indicated concentrations of docetaxel. The viability of the cells was determined by MTT assays 5 days later.

Figure 8A:
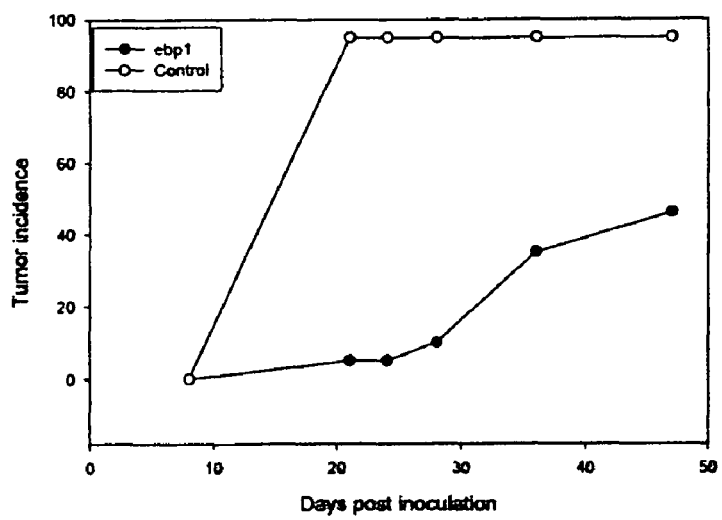
Figure 8B:
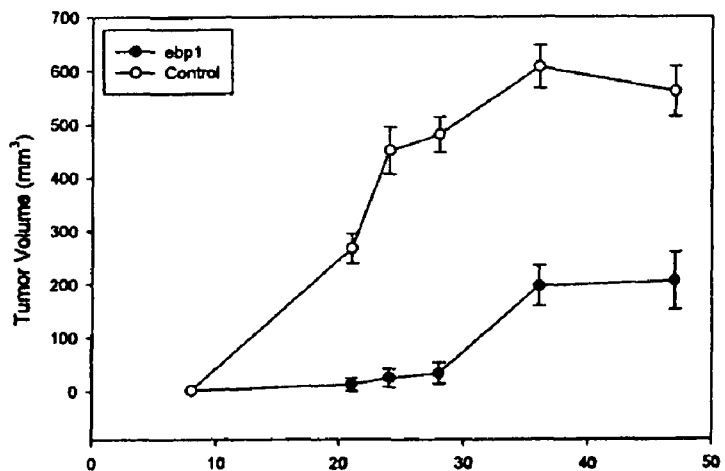
Figure 8C:
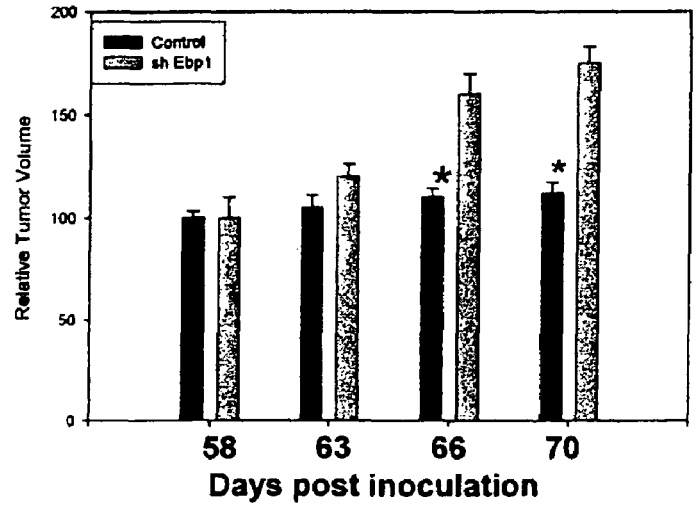

FIG. 8A-C. Manipulation of EBP1 expression affects growth of prostate cancer cells in vivo. A. Ectopic expression of EBP1 reduces the growth of androgen independent cells in athymic female mice C81 vector or EBP1 transfected cells were injected subcutaneously into female athymic mice. Tumor development with time is shown (n=10 animals, 20 sites per group). B. Tumor volumes and growth rate. Tumor volumes were calculated as described in "Materials and Methods". Each point represents the mean±SE (10 mice per group injected at 20 sites). C. Elimination of EBP1 expression enhances growth of androgen dependent LNCaP cells in vivo. A16 lentivirus control or C13 EBP1 shRNA transduced LNCaP cells were injected subcutaneously into female athymic mice. Tumor volumes were calculated as described in "Materials and Methods". Each point represents the mean±SE (10 mice per group injected at 20 sites). * indicates p 0.04.

FIG. 9A-D. Ectopic expression of EBP1 blocks HRG-induced proliferation. (A) MCF 7 cells were stably transfected with a control Flag vector (CMV) or a FLAG-EBP1 vector (EBP1). Cells lysates were analyzed by Western blotting for FLAG and actin levels as indicated (left panel) or EBP1 and actin (right panel). (B) MCF-7 vector control (Control) or EBP1 transfected cells (EBP1) were plated in 96-well plates in complete media overnight, and then switched to media with 2% FBS and the indicated concentrations of HRGb1 as described in Section 2. Growth was determined 4 days later using a Promega Proliferation Assay. Each point represents the mean±SD for six wells. Data shown are representative of three experiments. (C) AU565 vector control (Control) or EBP1 transfected cells (EBP1) were plated in 96-well plates in complete media overnight, and then switched to media with 2% FBS and the indicated concentrations of HRGβ1. Growth was determined 4 days later using a Promega Proliferation Assay. Each point represents the mean±SD for six wells and is representative of two experiments. (D) MCF-7 vector control (Control) or EBP1 transfected cells (EBP1) were plated in 96-well plates in complete media overnight, and then switched to media with 2% FBS and the indicated concentrations of EGF. Growth was determined 4 days later using a Promega Proliferation Assay. Each point represents the mean±SD for six wells and is representative of two experiments.

FIG. 10A-C. Effect of ectopic expression of EBP1 on ErbB3 or ErbB2 protein levels. (A and B) Lysates of logarithmically growing MCF-7 vector control cells (CMV) or EBP1 transfected cells (Ebp1) or (C) AU565 cells were blotted with antibodies for ErbB3 or ErbB2 and actin as indicated. Data are representative of three experiments.

Figure 11A:
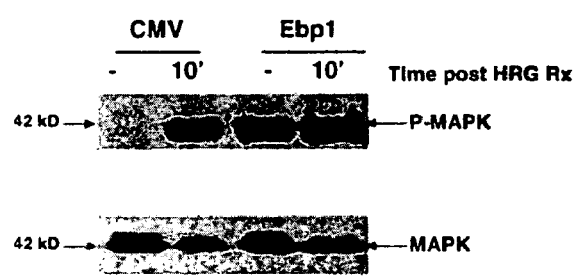
Figure 11B:
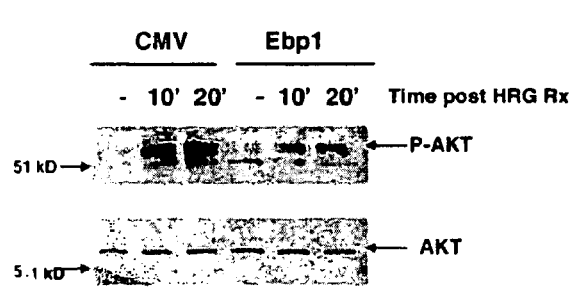
Figure 11C:
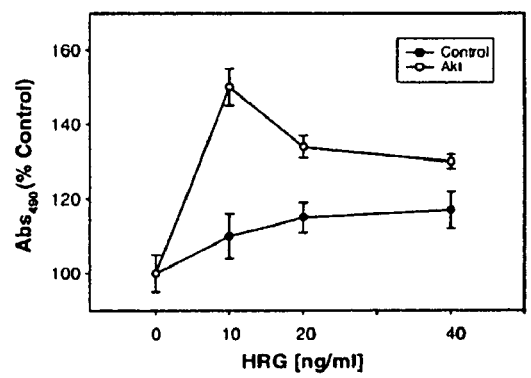

FIG. 11A-C. Ebp1 affects HRG-induced downstream signaling pathways. Serum starved MCF-7 vector control (CMV) or EBP1 transfected cells (Ebp1) cells were stimulated with HRG (20 ng/ml) for the indicated times. Cells lysates were blotted with antibodies to (A) phosphor MAPK and total MAPK or (B) phospho-Akt or total AKT. Data are representative of three experiments. (C) MCF-7 ebp1 stably transfected cells were transiently transfected with a constitutively activated AKT in complete media. Eight hours after transfection, cells were refed with media with 2% serum and the indicated concentrations of HRG. Growth was assessed by MTT assay 3 days later. Data are representative of two experiments.

FIG. 12A-B. EBP1 shRNA promotes HRG stimulated cell growth. (A) Lysates of MCF-7 cells stably transduced with a control lentivirus (Con) or an EBP1 targeted shRNA (shEbp1) were collected and resolved by SDS-PAGE. Western blots were probed for endogenous EBP1 or actin as indicated. (B) MCF-7 cells transduced with a control lentivirus or a lentivirus with shRNA targeted to EBP1 were plated in 2% FBS and 10 ng/ml HRG as described in Section 2. Cell proliferation was measured 4 days later by a Promega Proliferation Assay. Each bar represents the mean of six wells ±SD. Data are representative of three experiments.

Figures 13A, 13B, 13C:
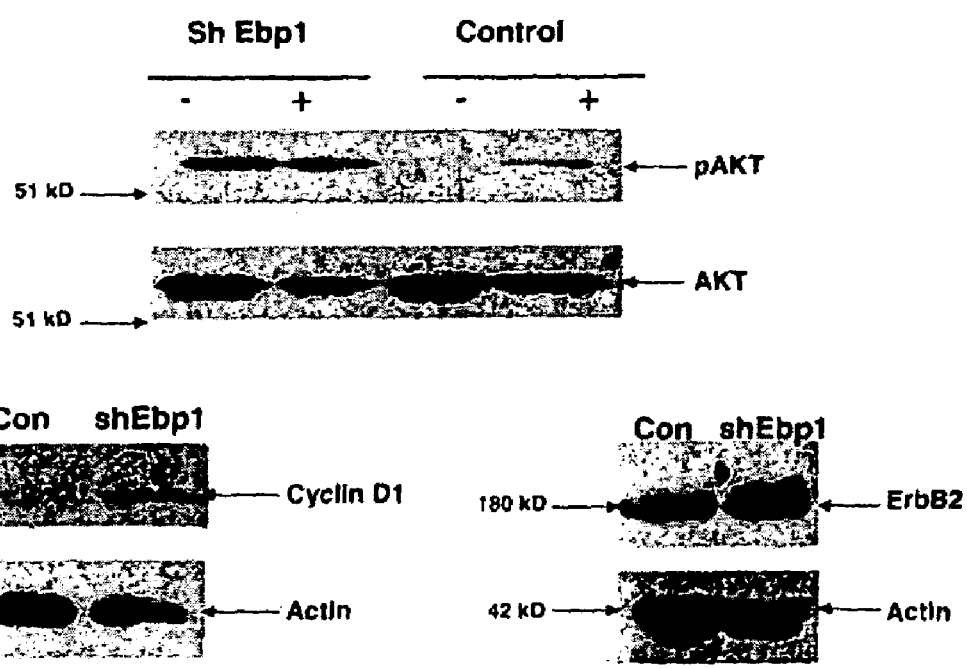

FIG. 13A-C. Changes in downstream signaling pathways in EBP1 knockdown cells. (A) MCF-7 cells transduced with a lentivirus with shRNA targeted to EBP1 (shEbp1) or a control lentivirus (Con) were serum starved (□) and then stimulated with HRG (20 ng/ml) for 10 min (+). Cells lysates were blotted with antibodies to phospho-Akt or total AKT as indicated. (B and C) Lysates of logarithmically growing MCF-7 cells transduced with a control lentivirus (Con) or a lentivirus targeted to EBP1 (shEbp1) were analyzed by Western blotting for cyclin D or actin or ErbB2 and actin as indicated. Data are representative of two experiments.

DETAILED DESCRIPTION OF THE INVENTION

The present invention is predicated on the discovery that when EPB1, an ErbB3 binding protein, is expressed within androgen-independent prostate cancer cells, the cells are converted to an androgen-dependent or androgen-sensitive phenotype. This is important because conversion to androgen-sensitivity makes the prostate cancer cells susceptible to anti-androgen therapy, thereby promoting cessation of uncontrolled growth, and control of the disease process. Without being bound by theory, it appears that Erb1 physically interacts with the N-terminal domain of AR, thereby repressing AR-mediated transactivation and decreasing BCL-2, AR, and ErbB2 protein levels in the cancer cells. As a result, growth and metastatic potential of the cancer cells is attenuated or destroyed. Importantly, cancer cells that are so treated become more susceptible to killing or damage by other known cancer treatments, e.g. other chemotherapy agents, radiation, etc.

The capability to inhibit transcriptional activity of the AR by targeting the N-terminal domain to block androgen-independent tumor growth presents a new direction for the clinical management of hormone-independent prostate cancer, given the fact that AR can be activated in the absence of cognate ligand by alternative pathways through a mechanism involving its N-terminal domain. As described in the Examples presented below, growth and transcription of AR-regulated reporter genes in response to androgen is decreased in EPB1 LNCaP transfectants but the cells do not become androgen-independent. The agonist activity of the anti-androgen cyproterone acetate is also abolished in EPB1 transfectants. This is of potential clinical interest also as mutation of AR leading to promiscuous activation has been postulated to be one mechanism of the development of androgen resistance. Endogenous EPB1 is reduced in LAPC androgen-independent xenografts and in the C-81 androgen-independent cell line grown in vitro. EPB1 inhibits tumorigenesis of LNCaP cells in a xenograft mouse model once EPB1 is stably transfected. EPB1 can downregulate androgen receptor and its target genes—the critical component in the design of prostate cancer treatment now that the AR, itself, has been documented to outwit prostate cancer drugs.

Thus, in one aspect, the present invention provides a method of repressing a cell-cycle gene, which is regulated by an E2F transcription factor, in a cell. The method comprises contacting the cell with a cell-cycle gene-repressing amount of EPB1. By "cell-cycle gene" we mean a gene whose expression varies with different phases of the cell cycle. The EPB1 can be in the form of a nucleic acid, such as DNA or RNA, which directly or indirectly results in expression of the ErbB3 binding protein, or the protein itself. The cell can be in a tumor. The tumor can be in a mammal such as a human.

In another embodiment, the invention provides a method of inhibiting unregulated proliferation of a hormone-insensitive cell, the proliferation of which is otherwise susceptible to regulation by administration of a hormone. The method includes the steps of providing the cell with a therapeutically effective amount of EPB1 to convert said cell to a hormone-regulated phenotype (i.e. to a cell that exhibits characteristics of a hormone-sensitive cell and that is responsive to hormones); and providing the cell with at least one antiproliferation therapy to reduce unregulated cell proliferation.

I. Definitions

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order (e.g., methods comprising administering more than one composition or agent is not limited by the order of administration of the one or more composition or agent) unless otherwise indicated herein or otherwise clearly contradicted by context. The use of any and all examples, or exemplary language (e.g., "such as", "for example", etc.) provided herein, is intended merely to better illustrate the invention and does not pose a limitation on the scope of the invention. Furthermore, no language in the specification should be construed as indicating any non-claimed element as essential to the practice of the invention.

The use of the term "about" refers to numeric values, including whole numbers, fractions, percentages, etc., whether or not explicitly indicated. The term "about" generally refers to a range of numerical values (e.g., +/−5-10% of the recited value) that one would consider equivalent to the recited value (e.g., having the same function or result). In some instances, the term "about" may include numerical values that are rounded to the nearest significant figure.

Antiproliferation therapy includes, for example, surgical therapy, radiation therapy, administering an anticancer agent (including, for example, a single agent and a combination of two or more agents), such as, for example, an antiandrogen, immunotherapy, antineoplastons, investigational drugs, vaccines, less conventional therapies (sometimes referred to as novel or innovative therapies, which include, for example, chemoembolization, hormone therapy, local hyperthermia, photodynamic therapy, radiofrequency ablation, stem cell transplantation, and gene therapy), prophylactic therapy (including, for example, prophylactic mastectomy or prostatectomy), alternative and complementary therapies (including, for example, dietary supplements, megadose vitamins, herbal preparations, special teas, physical therapy, acupuncture, massage therapy, magnet therapy, spiritual healing, meditation, pain management therapy, and naturopathic therapy (including, for example, botanical medicine, homeopathy, Chinese medicine, and hydrotherapy), and a combination of any of the foregoing. In particular embodiments, an antiproliferation therapy includes a therapy selected from the group consisting of an antiandrogen, administration of an anticancer agent, radiation therapy, and surgery. When a combination therapy of the invention is contemplated (including, for example, a combination of EBP1 and an antiproliferation therapy), the combination comprises, for example, administration of the therapies concurrently (i.e., at the same time), sequentially (i.e., at different times), or any combination thereof.

"Inhibit" as used herein has the generally understood meaning, e.g. to decrease, attenuate, restrict, reduce, repress, lessen, down-regulate, slow, lower, etc. In some embodiments of the invention, unregulated cell proliferation of cells that can otherwise be regulated by hormone administration is inhibited. Such inhibition is generally characterized by a decrease in the activity that is inhibited of at least about 10%, 20%, 30%, 40%, 50%, 60%, 70%, 80%, or 90% or more. Preferably, the decrease is at least about 50%, more preferably at least about 75%, and most preferably about 90% or more. In some cases, the activity may be inhibited 100%, i.e. the activity may be entirely abolished.

Similarly, references to "transforming" (e.g. as in "transforming at least a portion of said cells"), "treating" (e.g. as in "treating cancer"), or "reversing" (e.g. reversing a phenotype), "sensitizing" (e.g. "sensitizing a cancer cell to treatment with an antiproliferation therapy"), "reducing" (e.g. as in "reducing proliferation" or "reducing unregulated cell proliferation"), "repressing" (as in "gene repressing"), etc., what is meant is that a physical observable (i.e. a measurable outcome) is changed to an extent that is at least about 10%, 20%, 30%, 40%, 50%, 60%, 70%, 80%, or 90% or more different from a control that is not so transformed, treated, reversed, sensitized, reduced, etc. Preferably, the change is at least about 50%, more preferably at least about 75%, and most preferably about 90% or more, and may be 100%. For example, when "treating" a disease, the change is generally an amelioration of symptoms or the severity of symptoms, or the number of symptoms. For example, if treating cancer, the change may be a decrease in tumor volume, the number of tumors, or the growth rate of tumors; a decrease in the number of cancer cells vs non-cancer cells in samples taken e.g. before and after treatment, or in a treated experimental sample vs a control (untreated) sample; or a difference in metastatic potential or metastatic occurrences; or a change to a more favorable phenotype (e.g. one that is more amenable to treatment or for which the prognosis for recovery or control of the disease is better. For example, for prostate cancer cells, a change from androgen-insensitivity to androgen-sensitivity, or increased sensitivity to damage or killing by other therapeutic agents may represent such a change. Such change may be measured within a single entity over time (e.g. a cell that is treated, an individual that is treated, etc.). More frequently, such change is measured in a group of entities (e.g. a group or plurality of cells, individual subjects, etc.).

The use of the phrases such as a "cell-cycle gene-repressing amount" or a "prostate cancer-inhibiting (or treating) amount" of EPB1 can be determined in accordance with dosage range finding techniques as are known in the art. For example, if a viral vector is used, a cell should be contacted, for example, with about 1-100, or preferably about 5 to 50, or more preferably about 10-25 viral vector particles per cell. If liposomes or protein-complexed or polymer-packaged DNA is used, a cell should be contacted with, for example, about 0.5 to 5.0 μl, preferably about 1-2.5 μl, and most preferably about 1.5 microliters of DNA encoding Erb1 per 50,000 cells. Generally, cell-targeting methods can reduce the number of particles needed, as can chemical/physical transfection of uncomplexed nucleic acids or proteins. If EPB1 protein is administered or provided directly to a cell, the quantity that is administered should be in the range of from about 0.5 to about 5 μg/ml, and preferably about 1 μg/ml.

A "therapeutically effective amount" or a "therapeutic effective amount" is an amount of an EPB1 of the invention that alleviates (alone or in combination with one or more of an antiproliferation therapy) totally or partially, a pathophysiological effect of cancer. A therapeutically effective amount or a therapeutic effective amount can also be an amount that is given prophylactically thereby inhibiting a pathophysiological effect of cancer, an amount that transforms a hormone-independent cancer into a hormone-dependent cancer (e.g., changes the phenotype of a prostate cancer that is hormone refractory to a prostate cancer that is hormone susceptible), or amount that can sensitize a cancer cell to an antiproliferation therapy. The amount will depend upon, for example, subject size, gender, magnitude of the associated condition or injury, and genetic or non-genetic factors associated individual pharmacokinetic or pharmacodynamic properties of the administered molecule of the invention. For a given subject in need thereof a therapeutically effective amount or a therapeutic effective amount can be determined by those of ordinary skill in the art and by methods known to those of ordinary skill in the art.

As used herein dysregulated cell growth refers to cells that are characterized by unwanted, usually pathological (disease-causing) uncontrolled growth, either by direct growth into adjacent tissue through invasion or by growth at distal sites through metastasis. Dysregulated growth may also be referred to as unregulated growth, hyperproliferation, over proliferation, unwanted cell growth or unwanted cell proliferation, pathological proliferation, etc. The methods of the invention are directed to correcting or destroying a cell or cells demonstrating such dysregulated and/or hyperproliferative growth.

The methods of the invention generally involve administering or providing the protein EPB1 to such cells. Administration can be carried out in any suitable manner. For example, chemical transfection (e.g., calcium phosphate, lipid complexes, or protein complexes) or physical transfection (e.g., electroporation, microinjection, or ballistics) can be used to introduce EPB1-expressing nucleic acids, in accordance with methods known in the art. Electroporation with high-voltage electric impulses can transiently increase cell membrane permeability, allowing large molecules, including cytotoxic agents, to enter the cell. Cells can be contracted with EPB1 protein by direct contact, such as by injection into or in the vicinity of the cell in which repression of a cell-cycle gene is desired.

The EPB1 can be expressed from a vector, such as a viral vector, in which case the cell is contacted with the viral vector. Examples of suitable viral vectors include lentiviral vectors, retroviral vectors, adenoviral vectors, adeno-associated viral vectors, and herpes viral vectors. The viral vector can be targeted to a cell-surface molecule if desired. Alternatively or additionally, the cell, in which repression of a cell-cycle gene is desired, can be contacted directly. For example, if the cell is in a tumor, the viral vector can be injected into or in the immediate vicinity of the tumor.

The nucleotide sequence of EBP1, the gene that encodes the EPB1 protein, is set forth in FIG. 1 as SEQ ID NO: 1. The amino acid sequence of EPB1 is set forth in FIG. 2 as SEQ ID NO: 2. It is understood by one of ordinary skill in the art that, due to the degeneracy of the genetic code, more than one nucleotide sequence can encode for the same amino acid sequence. All nucleotide sequences the encode EPB1 can be used in the context of the present invention. One of ordinary skill in the art will also appreciate that such nucleotide and amino acid sequences can involve the use of nonnaturally occurring or modified nucleotides or amino acids, respectively. Also appreciated is that nucleotide and amino acid sequences can be modified somewhat, such as by insertion, deletion, and other types of mutations, without adversely affecting the activity of the protein. In some instances, such modifications may enhance the activity of the protein.

The use of nonnaturally occurring or modified nucleotides and amino acids, the introduction of mutations in nucleotide and amino acid sequences, and the construction of viral vectors is within the skill in the art, as is the targeting of viral vectors to cell-surface molecules. See, e.g., Sambrook et al., Molecular Cloning: A Laboratory Manual, Cold Spring Harbor Laboratory, 3rd edition, 2001; Federico, Lentivirus Gene Engineering Protocols, Humana Press, 2003; and Machida, Viral Vectors for Gene Therapy: Methods and Protocols, Humana Press, 2002.

Alternatively, the EPB1 can be expressed from polymer-packaged DNA, in which case the cell is contacted with the polymer-packaged DNA (see, e.g., Mixson, U.S. Pat. No. 6,080,728, which is hereby incorporated by reference).

In some embodiments, the invention provides for the use of the entire EPB1 protein or for nucleic acids encoding the entire EPB1 protein, as set forth in SEQ ID NO: 1. However, those of skill in the art will recognize that the expression of the entire primary sequence of Epb1 is not necessarily required. For example, portions of the Epb1 protein may display the same or similar efficacy as does the entire protein in the practice of the invention. For example, mimetic polypeptides or peptides which include or are based on (usually contiguous) portions of EPB1 may also be used, e.g. to mediate the conversion of androgen-independent tumors to androgen-sensitive tumors, to treat cancers, to sensitize cancer cells to other therapeutic agents, etc. Such peptides will generally be in the range of at least about 10-15 amino acids in length (but may be longer, e.g. about 20, or 30, or 40, 45, or 50 or more amino acids), and will typically be capable of adopting secondary and/or tertiary structure capable of binding to proteins within a cancer cell that control or influence the cell cycle, e.g. AR and or ErbB3. For example, the last 45 amino acids of EPB1 appear to be necessary or important for EPB1 function (e.g. residues 350-394) and this portion of the sequence may be used. Peptides or polypeptides comprising any such portion of the EPB1 protein may be administered, so long as the peptide or polypeptide contains one or more binding motifs that allow binding to cell-cycle controlling molecules (e.g. AR, ErbB3, etc.). Further, such binding should efficacious in modulating (inhibiting, decreasing, etc.) the activity of the cell-cycle regulating protein with the result that cancer can be treated, phenotypes reversed, cells sensitized, etc., as described herein. Such peptides or polypeptides may also be contained in a chimeric or fusion amino acid sequence that also contains other beneficial or suitable elements, e.g. targeting elements, stabilizing elements, etc. For example, EBP1, which regulates ErbB3 induction of cell cycle regulated genes, might be targeted to prostate cancer cells that overexpress ErbB3 by fusing the protein (or portions of the protein as discussed above) to antibodies that target ErbB3.

The invention also provides a method comprising repressing a cell-cycle gene, which is regulated by an E2F transcription factor, in a cell in combination with one or more methods of regulating cell growth. In particular embodiments, the method comprises contacting the cell with a cell-cycle gene-repressing amount of EPB1 and the administration of an antiandrogen, an anticancer agent, radiation therapy, surgery, or any combination thereof.

The invention also provides a method of treating prostate cancer in a patient or subject in need thereof (usually a mammal) comprising administering EPB1 to the patient (e.g. a prostate cancer-inhibiting amount of EPB1) in combination with one or more modes of antiproliferation (e.g. anticancer) therapies. In particular embodiments, the method comprises administering EPB1 in combination with the administration of an antiandrogen, an anticancer agent, anticancer combinations (i.e., combinations of anticancer agents), radiation therapy, surgery, or any combination thereof. Epb1 and the antiproliferation agent may be administered together. Alternatively, they may be administered one at a time, i.e. the EPB1 may, for example, be administered first, followed by administration of the antiproliferative therapy, or vice versa.

In specific embodiments of the invention the patient or subject is a mammal, frequently a primate, and in preferred embodiments of the invention the mammal is a human.

The invention also encompasses compositions for administration comprising EPB1 (or nucleic acids encoding EPB1) one or more anticancer agents, generally with a physiologically or pharmacologically suitable (compatible) carrier. The preparation of such compositions for use as vaccines is well known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of active agent(s) in the formulations may vary. However, the amount of EPB1 (or nucleic acids encoding EPB1) in such compositions will generally be in the range of about 1-99%, and the one or more anticancer agents will be present in the amount of about 1-99% each.

In certain embodiments, the invention comprises administering EPB1 in combination with an antiandrogen, and the invention is thus drawn to compositions comprising EPB1 in combination with an antiandrogen. An antiandrogen is a molecule (including a non-steroidal molecule and a steroidal molecule) that is naturally occurring or made, synthetically made, or semi-synthetically made, which is generally characterized by an activity that reduces, inhibits, or blocks the biological effect of an androgen molecule, including for example, testosterone, and metabolites of testosterone, including for example, dihydrotestosterone (DHT). An antiandrogen can have an effect, for example, at the level of receptor binding of an androgen to its respective receptor or at the level of biosynthesis of an androgen (e.g., 5-alpha reductase inhibition).

Antiandrogens that comprise the compositions and methods of the instant invention include, for example, finasteride, dutasteride, FCE 28260 (Giudici D, et al, J Steroid Biochem Mol Biol. 1996 June; 58(3):299-305), abarelix, bicalutamide, buserelin, casodex, estrogen(s), conjugated estrogen(s), esterified estrogens(s), estrace, estromustine, estradiol, conjugated testosterone(s), esterified testosterone(s), eulexin, flutamide, goserelin, gynodiol, histrelin, leuprolide, menest, nilutamide, triptorelin, ketoconazole, cyproterone, or spironolactone. In other particular embodiments, an antiandrogen comprises two or more of the foregoing antiandrogens. In specific embodiments, an antiandrogen is bicalutamide.

In certain embodiments, the invention comprises administering EPB1 in combination with an anticancer agent or a combination of anticancer agents, and the invention is thus also drawn to compositions comprising EPB1 in combination with an anticancer agent or a combination of anticancer agents. An anticancer agent is a molecule that is naturally occurring or made, synthetically made, or semi-synthetically made, which is generally characterized by an activity that maintains, reduces, inhibits, or blocks cell growth, replication, and/or malignancy.

Anticancer agents that comprise the compositions and methods of the instant invention include, for example, Abraxane, Aldara, Alimta, Aminolevulinic Acid, Anastrozole, Aprepitant, Arimidex, Aromasin, Arranon, Arsenic Trioxide, Avastin, Azacitidine, Bevacizumab, Bexarotene, Bortezomib, Capecitabine, Cetuximab, Cisplatin, Clofarabine, Clofarex, Clolar, Dacogen, Dasatinib, Decitabine, Docetaxel, Ellence, Eloxatin, Emend, Epirubicin Hydrochloride, Erbitux, Erlotinib, Exemestane, Faslodex, Femara, Fulvestrant, Gefitinib, Gemcitabine, Gemtuzumab Ozogamicin, Gemzar, Gleevec, Herceptin, Hycamtin, Imatinib Mesylate, Iniquimod, Iressa, Kepivance, Lenalidomide, Letrozole, Levulan, Methazolastone, Mylosar, Mylotarg, Nanoparticle Paclitaxel, Nelarabine, Nexavar, Nolvadex, Oncaspar, Oxaliplatin, Paclitaxel, Paclitaxel Albumin-stabilized Nanoparticle Formulation, Palifermin, Panitumumab, Pegaspargase, Pemetrexed Disodium, Platinol-AQ, Platinol, Revlimid, Rituxan, Sclerosol Intrapleural Aerosol, Sorafenib Tosylate, Sprycel, Sterile Talc Powder, Sunitinib Malate, Sutent, Synovir, Tamoxifen, Tarceva, Targretin, Taxol, Taxotere, Temodar, Temozolomide, Thalomid, Thalidomide, Topotecan Hydrochloride, Trastuzumab, Trisenox, Vectibix, Velcade, Vidaza, Vorinostat, Xeloda, Zoledronic Acid, Zolinza, Zometa, doxorubicin, adriamycin, bleomycin, daunorubicin, dactinomycin, epirubicin, idarubicin, mitoxantrone, valrubicin, hydroxyurea, mitomycin, fluorouracil, 5-FU, methotrexate, floxuridine, interferon alpha-2b, glutamic acid, plicamycin, 6-thioguanine, aminopterin, pemetrexed, raltitrexed, cladribine, clofarabine, fludarabine, mercaptopurine, pentostatin, capecitabine, cytarabine, carmustine, BCNU, lomustine, CCNU, cytosine arabinoside, cyclophosphamide, estramustine, hydroxyurea, procarbazine, mitomycin, busulfan, medroxyprogesterone, estramustine phosphate sodium, ethinyl estradiol, estradiol, megestrol acetate, methyltestosterone, diethylstilbestrol diphosphate, chlorotrianisene, testolactone, mephalen, mechlorethamine, chlorambucil, chlormethine, ifosfamide, bethamethasone sodium phosphate, dicarbazine, asparaginase, mitotane, vincristine, vinblastine, etoposide, teniposide, Topotecan, IFN-gamma, irinotecan, campto, irinotecan analogs, carmustine, fotemustine, lomustine, streptozocin, carboplatin, oxaliplatin, BBR3464, busulfan, dacarbazine, mechlorethamine, procarbazine, thioTEPA, uramustine, vindesine, vinorelbine, alemtuzumab, tositumomab, methyl aminolevulinate, porfimer, verteporfin, lapatinib, nilotinib, vandetanib, ZD6474, alitretinoin, altretamine, amsacrine, anagrelide, denileukin diftitox, estramustine, hydroxycarbamide, masoprocol, mitotane, tretinoin, or other anticancer agents, including, for example, antibiotic derivatives, cytotoxic agents, angiogenesis inhibitors, hormones or hormone derivatives, nitrogen mustards and derivatives, steroids and combinations, and antimetholites. In other particular embodiments, an anticancer agent comprises two or more of the foregoing anticancer agents. In specific embodiments, an anticancer agent is mitoxantrone or docetaxel.

Specific combinations of anticancer agents that comprise the compositions and methods of the instant invention include, for example, CHOP (Cytoxan, Hydroxyrubicin (Adriamycin), Oncovin (Vincristine), Prednisone), CHOP-R (CHOP, rituximab), FOLFOX (Fluorouracil, leucovorin (folinic acid), oxaliplatin), VAD (Vincristine, Adriamycin (doxorubicin), dexamethasone), Thal/Dex (Thalidomide, dexamethasone), COP or CVP (Cyclophosphamide, vincristine (Oncovin), and prednisone), m-BACOD (Methotrexate, bleomycin, doxorubicin (Adriamycin), cyclophosphamide, vincristine (Oncovin), dexamethasone (Decadron)), ProMACE-CytaBOM (Prednisone, doxorubicin (adriamycin), cyclophosphamide, etoposide, cytarabine, bleomycin, vincristine (Oncovin), methotrexate, leucovorin), COPP (Cyclophosphamide, Oncovin (vincristine), procarbazine, prednisone), MACOP-B (Methotrexate, leucovorin, doxorubicin (Adriamycin), cyclophosphamide, vincristine (Oncovin), prednisone, bleomycin), MOPP (Mechlorethamine, vincristine (oncovin), procarbazine, prednisone), ProMACE-MOPP (Methotrexate, doxorubicin (Adriamycin), cyclophosphamide, etoposide, MOPP), ABVD (Adriamycin, bleomycin, vinblastine, dacarbazine), BEACOPP (Bleomycin, etoposide, Adriamycin (doxorubicin), cyclophosphamide, Oncovin (vincristine), procarbazine, prednisone), Stanford V (Doxorubicin (Adriamycin), mechlorethamine, bleomycin, vinblastine, vincristine (Oncovin), etoposide (VP-16), prednisone), ECF (Epirubicin, cisplatin, fluorouracil), BEP (Bleomycin, etoposide, platinum (cisplatin)), and PCV (Procarbazine, lomustine (CCNU), vincristine).

In certain embodiments, the invention comprises administering EPB1 to a mammal in combination with radiation therapy. Radiation therapy is the use of certain types of high-energy radiant to kill cancer cells and/or shrink tumors or as prophylactic treatment to prevent cancer. Generally, radiation therapy uses high-energy radiation from, for example, x-rays, gamma rays, neutrons, and other sources. Radiation may be external in origin (e.g., come from a machine outside the body, external-beam radiation therapy) or may originate from radioactive material placed in the body (e.g., internal radiation therapy, implant radiation, or brachytherapy). Systemic radiation therapy uses a radioactive substance (e.g., radiopharmaceuticals, radioactive drugs, radionucleotides, etc.) such as a radiolabeled monoclonal antibody directed to cancer cells that circulates throughout the body. Types of radiation therapy include, but are not limited to, intraoperative radiation therapy, prophylactic cranial irradiation, interstitial radiation, intracavitary or intraluminal radiation, stereotactic radiation, 3-D conformal radiation, external beam radiation, high-dose rate (HDR) brachytherapy, intensity modulated radiation therapy (IMRT), MammoSite radiation therapy system (RTS), TheraSphere, and TomoTherapy highly integrated adaptive radiotherapy (HI-ART). Radiation therapy can also be used in combination with radiosensitizers and radioprotectors, which are entities that modify a cell's response to radiation. Radiosensitizers make a cell more sensitive to the effects of radiation whereas radioprotectors make a cell less sensitive to the effects of radiation. Several compounds are under study as radiosensitizers. In addition, some anticancer agents, such as, for example, 5-fluorouracil and cisplatin, make cancer cells more sensitive to radiation therapy. Hyperthermia, the use of heat, can also be used in conjunction with radiation therapy. The combination of heat and radiation can increase the efficacy of radiation therapy directed to cancer cells.

In certain embodiments, the invention comprises administering EPB1 to a mammal in combination with surgery. Surgery generally involves an invasive procedure directed to physically removing cancer cells. Surgery includes, for example, tumor resection and cavitron ultrasonic surgical aspiration (CUSA).

As discussed above, in one embodiment, Epb1 is delivered as a protein. However, it may also be delivered as a nucleic acid encoding the protein. For example, EPB1 may be delivered to cells via an EPB1-expressing viral vector. Accordingly, the present invention provides compositions comprising an EPB1-expressing viral vector. The viral vector may express a cell-cycle gene-repressing amount of EPB1. The viral vector can be a lentiviral vector. Alternatively or additionally, the viral vector can be targeted to a cell-surface molecule.

In another embodiment, the present invention provides a composition comprising polymer-packaged DNA comprising and expressing a cell-cycle gene-repressing amount of EPB1. Pharmaceutical compositions are known in the art. See e.g., Gennaro, Remington: The Science and Practice of Pharmacy, Lippincott, Williams & Wilkins, 20.sup.th ed., 2003. It noted that although the invention provides embodiments drawn to viral vectors and polymer-packaged DNA as a mechanism of administering EPB1, the scope of invention is broader than such. The delivery of EPB1 may include, for example, all viral and non-vector means of delivering a gene.

In certain embodiments, the present invention relates to the delivery of an amino acid sequence of the invention conjugated to, fused with, or otherwise combined with, a peptide known as protein transduction domain (PTP). A PTD is a short peptide that facilitates the movement of an amino acid sequence across an intact cellular membrane wherein said amino acid sequence would not penetrate the intact cellular membrane without the PTD. The conjugation with, fusion to, or otherwise combination of a PTD with a heterologous molecule (including, for example, an amino acid sequence, nucleic acid sequence, or small molecule) is sufficient to cause transduction into a variety of different cells in a concentration-dependent manner. Moreover, when drawn to the delivery of amino acids, it appears to circumvent many problems associated with polynucleotide and drug based delivery. Without being bound by theory, PTDs are typically cationic in nature causing PTDs to track into lipid raft endosomes and release their cargo into the cytoplasm by disruption of the endosomal vesicle. PTDs have been used for delivery of biologically active molecules, including amino acid sequences (see, for example, Viehl C. T., et al., Ann. Surg. Oncol. 12:517-525 (2005); Noguchi H., et al., Nat. Med. 10:305-309 (2004); and Fu A. L., et al., Neurosci. Lett. 368: 258-62 (2004); Del Gazio Moore et al., J Biol Chem. 279(31): 32541-4 (2004); US Application Publication No. 20070105775). For example, it has been shown that TAT-mediated protein transduction can be achieved with large proteins such as beta-galactosidase, horseradish peroxidase, RNAase, and mitochondrial malate dehydrogenase, whereby transduction into cells is achieved by chemically cross-linking the protein of interest to an amino acid sequence of HIV-1 TAT (see, for example, Fawell et al., PNAS, 91:664-668 (1994); Del Gazio et al., Mol Genet Metab. 80(1-2):170-80 (2003)).

Protein transduction methods encompassed by the invention include an amino acid sequence of the invention conjugated to, fused with, or otherwise combined with, a PTD. In particular embodiments a PTD of the invention includes, for example, the PTD from human transcription factor HPH-1, mouse transcription factor Mph-1, Sim-2, HIV-1 viral protein TAT, Antennapedia protein (Antp) of *Drosophila*, HSV-1 structural protein Vp22, regulator of G protein signaling R7, MTS, polyarginine, polylysine, short amphipathic peptide carriers Pep-1 or Pep-2, and other PTDs known to one of ordinary skill in the art or readily identifiable to one of ordinary skill in the art (US Application Publication No. 20070105775). One of ordinary skill in the art could routinely identify a PTD by, for example, employing known methods in molecular biology to create a fusion protein comprising a potential PTD and, for example, green fluorescent protein (PTD-GFP) and detecting whether or not GFP was able to transduce a cellular membrane of intact cells, which can be determined by, for example, microscopy and the detection of internal fluorescence. It is noted that the particular PTD is not limited by any of the foregoing and the invention encompasses any known, routinely identifiable, and after-arising PTD.

Methods of protein transduction are known in the art and are encompassed by the present invention (see, for example, Noguchi et al. (2006) Acta Med. Okayama 60:1-11; Wadia et al. (2002) Curr. Opin. Biotechnol. 13:52-56; Viehl C. T., et al., Ann. Surg. Oncol. 12:517-525 (2005); Noguchi H., et al., Nat. Med. 10:305-309 (2004); and Fu A. L., et al., Neurosci. Lett. 368:258-62 (2004); Del Gazio Moore et al., J Biol Chem. 279(31):32541-4 (2004); US Application Publication No. 2007/0105775; Gump et al., Trends in Molecular Medicine, 13(10):443-448 (2007); Tilstra et al., Biochem Soc Trans. 35(Pt 4):811-5 (2007); WO/2006/121579; US Application Publication No. 2006/0222657). In certain embodiments, a PTD may be covalently cross-linked to an amino acid sequence of the invention or synthesized as a fusion protein with an amino acid sequence of the invention. In other embodiments, methods for delivering an amino acid sequence of the invention includes a non-covalent peptide-based method using an amphipathic peptide as disclosed by, for example, Morris et al. Nat. Biotechnol. 19:1173-1176 (2001) and U.S. Pat. No. 6,841,535 and indirect polyethylenimine cationization as disclosed by, for example, Kitazoe et al. J. Biochem. 137:643-701 (2005)).

As a non-limiting illustration of a method of making a PTD fusion protein, an expression system that permits the rapid cloning and expression of in-frame fusion polypeptides using an N-terminal 11 amino acid sequence corresponding to amino acids 47-57 of TAT is used (Becker-Hapak et al., Methods 24:247-56 (2001); Schwarze et al., Science 285: 1569-72 (1999)). Using this expression system, cDNA of the amino acid sequence of interest is cloned in-frame with the N-terminal 6×His-TAT-HA encoding region in the pTAT-HA expression vector. The 6×His motif provides for the convenient purification of a fusion polypeptide using metal affinity chromatography and the HA epitope tag allows for immunological analysis of the fusion polypeptide.

Although recombinant polypeptides can be expressed as soluble proteins within *E. coli*, TAT-fusion polypeptides are often found within bacterial inclusion bodies. In the latter case, these proteins are extracted from purified inclusion bodies in a relatively pure form by lysis in denaturant, such as, for example, 8 M urea. The denaturation aids in the solubilization of the recombinant polypeptide and assists in the unfolding of complex tertiary protein structure which has been observed to lead to an increase in the transduction efficiency over highly-folded, native proteins (Becker-Hapak et al., supra). This latter observation is in keeping with earlier findings that supported a role for protein unfolding in the increased cellular uptake of the TAT-fusion polypeptide TAT-DHFR (Bonifaci et al., Aids 9:995-1000 (1995)). It is thought that the higher energy of partial or fully denatured proteins may transduce more efficiently than lower energy, correctly folded proteins, in part due to increased exposure of the TAT domain. Once inside the cells, these denatured proteins are properly folded by cellular chaperones such as, for example, HSP90 (Schneider et al., Proc. Natl. Acad. Sci. USA 93:14536-41 (1996)).

Following solubilization, bacterial lysates are incubated with NiNTA resin (Qiagen), which binds to the 6×His domain in the recombinant protein. After washing, proteins are eluted from the column using increasing concentrations of imidazole. Proteins are further purified using ion exchange chromatography and finally exchanged into PBS +10% glycerol by gel filtration (Nagahara et al., supra).

In certain embodiments the invention encompasses administration of an amino acid sequence of the invention conjugated to, fused with, or otherwise combined with, a PTD. In other embodiments, the invention encompasses administration of a nucleic acid sequence of the invention conjugated to, fused with, or otherwise combined with, a PTD. Both, an amino acid sequence and a nucleic acid sequence can be transduced across a cellular membrane when conjugated to, fused with, or otherwise combined with, a PTD. As such, administration of an amino acid sequence and a nucleic acid sequence is encompassed by the present invention. Routes of administration of an amino acid sequence or nucleic acid sequence of the invention include, for example, intraarterial administration, epicutaneous administration, ocular administration (e.g., eye drops), intranasal administration, intragastric administration (e.g., gastric tube), intracardiac administration, subcutaneous administration, intraosseous infusion, intrathecal administration, transmucosal administration, epidural administration, insufflation, oral administration (e.g., buccal or sublingual administration), oral ingestion, anal administration, inhalation administration (e.g., via aerosol), intraperitoneal administration, intravenous administration, transdermal administration, intradermal administration, subdermal administration, intramuscular administration, intrauterine administration, vaginal administration, administration into a body cavity, surgical administration (e.g., at the location of a tumor or internal injury), administration into the lumen or parenchyma of an organ, or other topical, enteral, mucosal, or parenteral administration, or other method, or any combination of the forgoing as would be known to one of ordinary skill in the art (see, for example, Remington's Pharmaceutical Sciences, 18th Ed. Mack Printing Company, 1990, incorporated herein by reference).

Methods of the invention are not limited by the order in which individual elements are administered. By way of illustration and without placing any limitations on the instant invention, specific compositions of the invention include, for example, a EPB1-expressing viral vector, which may be administered prior to, concomitant with, or subsequent to administration of an antiandrogen, an anticancer agent, radiation therapy, or surgery. Furthermore, the combination of therapies described herein is not meant to limit the invention in any manner. A combination of therapies can include, for example, those known and/or used in the art. A combination of therapies can also include, for example, a combination of any number and type of therapies known and/or used in the art. For example, a combination of therapies, which is not limited by the order of administration, of the invention can include, two or more therapies (e.g., an EPB1-expressing viral vector in combination with an anticancer agent), three or more therapies (e.g., an EPB1-expressing viral vector in combination with an anticancer agent and radiation therapy), four or more therapies, five or more therapies, and so forth.

Although embodiments of the invention are drawn to prostate cancer, the invention is not so limited. The invention can be used to treat cancer generally. Cancer refers to a pathophysiological state whereby a cell is characterized by dysregulated and/or hyper proliferative cellular growth and the ability to induce said growth, either by direct growth into adjacent tissue through invasion or by growth at distal sites through metastasis in both, adults or children, and both, acute or chronic, including, but not limited to, carcinomas and sarcomas, such as, acute lymphoblastic leukemia, acute myeloid leukemia, adrenocortical cancer, AIDS-related cancers, AIDS-related lymphoma, anal cancer, astrocytoma (cerebellar or cerebral), basal cell carcinoma, bile duct cancer, bladder cancer, bone cancer, brain stem glioma, brain tumor (e.g., ependymoma, medulloblastoma, supratentorial primitive neuroectodermal, visual pathway and hypothalamic glioma), cerebral astrocytoma/malignant glioma, breast cancer, bronchial adenomas/carcinoids, Burkitt's lymphoma, carcinoid tumor (e.g., gastrointestinal), carcinoma of unknown primary site, central nervous system lymphoma, cervical cancer, chronic lymphocytic leukemia, chronic myelogenous leukemia, chronic myeloproliferative disorders, colon cancer, colorectal cancer, cutaneous T-cell lymphoma, endometrial cancer, ependymoma, esophageal cancer, Ewing's Family of tumors, extrahepatic bile duct cancer, eye cancer (e.g., intraocular melanoma, retinoblastoma, gallbladder cancer, gastric cancer, gastrointestinal carcinoid tumor, gastrointestinal stromal tumor (GIST), germ cell tumor (e.g., extracranial, extragonadal, ovarian), gestational trophoblastic tumor, glioma, hairy cell leukemia, head and neck cancer, squamous cell head and neck cancer, hepatocellular cancer, Hodgkin's lymphoma, hypopharyngeal cancer, islet cell carcinoma (e.g., endocrine pancreas), Kaposi's sarcoma, laryngeal cancer, leukemia, lip and oral cavity cancer, liver cancer, lung cancer (e.g., non-small cell), lymphoma, macroglobulinemia, malignant fibrous histiocytoma of bone/osteosarcoma, medulloblastoma, melanoma, Merkel cell carcinoma, mesothelioma, metastatic squamous neck cancer with occult primary, mouth cancer, multiple endocrine neoplasia syndrome, multiple myeloma/plasma cell neoplasm, mycosis fungoides, myelodysplastic syndromes, myelodysplastic/myeloproliferative diseases, myeloma, nasal cavity and paranasal sinus cancer, nasopharyngeal cancer, neuroblastoma, non-Hodgkin's lymphoma, oral cancer, oral cavity cancer, osteosarcoma, oropharyngeal cancer, ovarian cancer (e.g., ovarian epithelial cancer, germ cell tumor), ovarian low malignant potential tumor, pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, pregnancy and breast cancer, primary central nervous system lymphoma, rectal cancer, retinoblastoma, rhabdomyosarcoma, salivary gland cancer, soft tissue sarcoma, uterine sarcoma, Sézary syndrome, skin cancer (e.g., non-melanoma or melanoma), small intestine cancer, supratentorial primitive neuroectodermal tumors, T-cell lymphoma, testicular cancer, throat cancer, thymoma, thymoma and thymic carcinoma, thyroid cancer, transitional cell cancer of the renal pelvis and ureter, trophoblastic tumor (e.g. gestational), unusual cancers of childhood and adulthood, urethral cancer, endometrial uterine cancer, uterine sarcoma, vaginal cancer, vulvar cancer, Waldenström's macroglobulinemia, Wilms' Tumor, and women's cancers.

The following examples serve to illustrate the present invention. The examples are not intended to limit the scope of the present invention in any way.

EXAMPLES

Example 1

Initial Studies of EPB1

Materials and Methods

Cell culture: All cell lines were obtained from the American Type Culture Collection (Manassas, Va.) and maintained at 37° C. in a humidified atmosphere of 5% $CO_2$ in air. Cell lines were routinely cultured in RPMI 1640 media supplemented with 10% fetal bovine serum (FBS).

Microarray Analysis: First and second strand cDNA were synthesized from 5-15 μg of total RNA at Genome Explorations (Nashville, Tenn.) using the SuperScript Double-Stranded cDNA Synthesis Kit (Gibco Life Technologies, Gaithersburg, Md.) and an oligo-dT.sub.24-T7 (5'-GGC CAG TGA ATT GTA ATA CGA CTC ACT ATA GGG AGG CGG-3') (SEQ ID NO: 3) primer according to the manufacturer's instructions. cRNA was synthesized labeled with biotinylated UTP and CTP by in vitro transcription using the T7 promoter-coupled, double-stranded cDNA as template and the T7 RNA Transcript Labeling Kit (ENZO Diagnostics Inc., Farmingdale, N.Y.). The fragmented cRNA was hybridized for U133A oligonucleotide arrays (Affymetrix, Santa Clara, Calif.) containing ~33,000 full-length annotated genes, together with additional probe sets designed to represent EST sequences. The arrays were then stained with phycoerythrein-conjugated streptavidin (Molecular Probes, Eugene, Oreg.), and the fluorescence intensities were determined using a laser confocal scanner (Hewlett-Packard, Palo Alto, Calif.). The scanned images were analyzed using Microarray software (Affymetrix). Sample loading and variations in staining were standardized by scaling the average of the fluorescent intensities of all genes on an array to constant target intensity for all arrays used. The signal intensity for each gene was calculated as the average intensity difference, represented by [E(PM−MM)/(number of probe pairs)], where PM and MM denote perfect-match and mismatch probes. Data analysis was conducted using Microarray Suite 5.0 (Affymetrix) following user guidelines. Only genes with a minimum expression level of 500 were included in this analysis. Only genes whose expression varied more than three-fold with a p value of <0.05 were considered to be significantly different between the two cell lines. AR-regulated genes include the Androgen Receptor (AR), PSA (kallikrein 3), Kallikrein 2, POV-1, TMPRSS2, and prostate-derived factor.

Real-Time Quantitative Reverse-Transcription PCR: The method of Nakanishi et al. (Nakanishi et al., 2003, Quantitative Analysis of Breast Cancer Resistance Protein and Cellular Resistance to Flavopiridol in Acute Leukemia Patients, Clin. Cancer Res., 9: 3320-3328) was used as previously described. RNA was extracted (Zhang et al., 2003, Repression of E2F1-Mediated Transcription by the ErbB3 Binding Protein EPB1 Involves Histone Deacetylases, Nucleic Acids Research, 31: 2168-2177) and cDNA was synthesized using random hexanucleotides from 1 .mu.g of RNA. Real-time quantitative RT-PCR was then performed on the LightCycler (Roche, Indianapolis, Ind.) platform to determine the relative mRNA levels of EPB1, AR, kallikrein-2 and POV-1. The following forward and reverse primers were selected using Primer Express software and synthesized by Core Laboratory of University of Maryland School of Medicine: EPB1, sense: 5'-GCACGCCAATAGAAGG-3' (SEQ ID NO: 4) and anti-sense: 5'-GTAAACGGCATGGCATC-3' (SEQ ID NO: 5), sense: 5'-AAGGCTATGAATGTCAGCCCA-3' (SEQ ID NO: 6) and antisense: 5'-CATTGAGGCTAGAGAG-CAAGGC-3' (SEQ ID NO: 7), Kallikrein-2, sense: 5'-CATC-CAGTCTCGGATTG-3' (SEQ ID NO: 8) and antisense: 5'-CTCATATTGTAGAGCGGGT-3' (SEQ ID NO: 9), POV-1, sense: 5'-AGTGCTGTGTTCGCCTTG-3' (SEQ ID NO: 10) and antisense: 5'-CACCTCAGAGCCGCTAAG-3' (SEQ ID NO: 11), Actin, sense: 5' GCT ATC CAG GCT GTG CTA TC-3' (SEQ ID NO: 12) and antisense TGT CAC GCA CGA TTT CC-3' (SEQ ID NO: 13). An SRBR Green PCR Kit was used (Applied Biosystems, Foster City, Calif.), and the analyses were performed in duplicate or triplicate in a total volume of 15 μl including 0.9 μl of 25 mM $MgCl_2$, 1.5 μl SYBR Green I, 0.3 μl Enzyme Mix, 0.75 μl of each primer (50 ng/μl), and 2 μl of cDNA synthesized with random hexamers. Target mRNA values were normalized using actin mRNA as an internal control. The relative quantitation of gene expression was performed using the comparative $\Delta\Delta C_t$ (threshold method) using β-actin as an internal control (Nikitakis et al., 2002, The Nonsteroidal Anti-Inflammatory Drug Sulindac Causes Down-Regulation of Signal Transducer and Activator of Transcription 3 in Human Oral Squamous Cell Carcinoma Cells, Cancer Research, 62:1004-1007).

Western Blot Analysis: Briefly, total cell extracts were prepared by direct lysis of cells with buffer containing 50 mM Tris-HCl (pH 7.4), 1 mM EDTA, 250 mM NaCl, 1% Triton® X-100, 0.5 mM dithiothreitol (DTT) and 1 mM phenylmethylsulfonyl (PMSF). Protein concentrations were measured using a detergent compatible kit (BioRad, Hercules, Calif.). Proteins were resolved by SDS-PAGE and analyzed by Western blotting as described (Xia et al., 2001, Analysis of the Expression Pattern of EPB1, an ErbB-3-Binding Protein, Biochem. Biophys. Res. Commun., 289:240-244). The AR antibody was from Santa Cruz Biotechnology (Santa Cruz, Calif.), the EPB1 antibody from Upstate (Lake Placid, N.Y.), the polyclonal antibody to actin from Sigma (St. Louis, Mo.), and the POV-1 antibody was a gift.

ChIP Assays: The method of Shang et al. (Shang et al., 2002, Formation of the Androgen Receptor Transcription Complex, Mol. Cell, 9:601-610) was used. Briefly, LNCaP EPB1 transfectants were grown in RPMI 1640 medium supplemented with 5% charcoal-stripped FBS (Sigma). After 3 days of culture, cells were treated with 5 μM bicalutamide for one hour, washed with phosphate-buffered saline (PBS) and centrifuged for 5 min. The pellets were then resuspended in 0.3 ml of lysis buffer (1% SDS, 10 mM EDTA, 50 mM Tris-HCl, pH 8.1, and 1× protease inhibitor cocktail (Roche). DNA was sheared on ice to the appropriate lengths (.about.500 basepairs) with 3 sets of 10-second pulses at 20% maximal output, followed by centrifugation for 10 min at 13,000 rpm at 4° C. Supernatants were mixed, aliquoted and diluted in NET-N buffer (20 mM Tris-HCl, pH 8.0, 150 mM NaCl, 10 mM EDTA, 0.5% NP-40, 1.5 mM $MgCl_2$, 10% glycerol and protease inhibitor cocktail) for a final volume of 1.5 ml. A portion of the diluted cell supernatant (1%) was kept to have crosslinks reversed and quantitate the amount of DNA present in samples for the PCR protocol. After pre-clearing with salmon sperm DNA/protein A agarose slurry for 30 min at 4° C., immunoprecipitation was performed overnight on a rotary shaker at 4° C. with specific antibodies or pre-immune IgG as a control. The samples were then mixed with sonicated salmon sperm DNA (100 μg/ml) and Protein A/G agarose (Oncogene Research Products, San Diego, Calif.) for another 6 h incubation. Agarose beads were washed sequentially in low salt, high salt, LiCl and TE buffer provided with a kit from Upstate and extracted two times with freshly prepared elution buffer (1% SDS, 0.1 M $NaHCO_3$). Eluates were pooled and incubated at 65° C. for 6 h to reverse the formaldehyde crosslinks. DNA was purified by phenol/chloroform extraction, and precipitated in the presence of 0.3 M sodium acetate and 20 μg tRNA in 2 volumes of ethanol at −20° C. overnight. The DNA pellets were dissolved in 50 μl of water. Nested PCR amplification of a 210 bp PSA promoter fragment (−250 to −39) was carried out using a 5' primer 5'-TCTGCCTTTGTC-CCCTAGAT-3' (SEQ ID NO: 14) and a 3' primer 5'-AACCT-TCATTCCCCAGGACT-3' (SEQ ID NO: 15). The PCR products were resolved on 2.5% agarose gels and visualized with ethidium bromide.

Cell Growth Assays: To measure growth in complete media, cells ($2\times10^4$) were seeded in triplicate in individual wells of 12-well tissue culture plates in RPMI-1640 with 10% FBS and cultured for the indicated number of days. Cells were trypsinized, stained with Trypan Blue (0.4%), and counted in a hemacytometer. For soft agar growth assays, increasing concentrations of cells (as indicated) were plated in 35 mm Petri dishes in complete media and 0.3% Difco Bacto Agar over an 0.5% agar layer. Colonies were counted after 10 days of incubation. For studies assessing the effect of dihydrotestosterone (DHT) on cell growth, cells ($2\times10^4$) were plated in 12-well plates in complete media. After a 24-hour attachment period, the medium was replaced with steroid-free medium [phenol red-free RPMI 1640 and 5% charcoal-stripped FBS (Sigma)] for 48 hours. The final concentration of testosterone in the steroid-reduced media was less than 5 pM. After 48 hours of steroid depletion, cells were re-fed with fresh steroid-reduced medium with or without the indicated concentrations of DHT and/or bicalutamide (10 μM), and total cell numbers were assessed 7 days later.

Luciferase Reporter Assays: Vector control or EBP1-transfected LNCaP ($5\times10^4$) cells were plated in twelve-well plates in complete media. When cells reached 50-60% confluence, they were transfected with 0.5 μg of MMTV-luc using the Fugene-6 reagent (Roche). Cells were also transfected with the RL-TK vector as an internal control. Complete medium was replaced after 24 h with phenol red and serum-free DMEM-F12 or RPMI 1640 with or without 10 nM R1881 (Slagsvold et al., 2001, DNA Binding-Independent Transcriptional Activation by the Androgen Receptor Through Triggering of Coactivators, J. Biol. Chem., 276: 31030-6) (NEN, Boston, Mass.) or cyproterone acetate (Sigma). Luciferase activity was determined as previously described using a Dual-Luciferase kit (Promega, Madison, Wis.). The activities of renilla luciferase were used to normalize any variations in transfection efficiency. The promoter activities of each plasmid construct were calculated as the firefly-renilla luciferase activity ratios. All transfection experiments were carried out in triplicate wells and repeated three times.

In Vivo Studies in SCID Mice: Male SCID mice, 4-6 weeks of age, were purchased from the National Cancer Institute (Frederick, Md.). Animals were housed in a pathogen-free environment under controlled conditions of light and humidity and received food and water ad libitum. LNCaP cells were grown in complete medium and 800 μg/ml of G418 until 80% confluent. Cells were scraped into phosphate-buffered saline (PBS), collected by centrifugation, and suspended in Matrigel™ (10 mg/ml) (Collaborative Research, Waltham, Mass.) at $1\times10^7$ cells/ml. Each mouse received s.c. injections at one site on each flank with 100 μl of cell suspension. Tumors were measured three times a week with calipers, and tumor volumes were calculated by the formula $0.5236\times r_1^2\times r_2$ (r1<r2). The animal protocols were approved by the Institutional Animal Care and Use Committee at the University of Maryland.

After sacrifice, tumors were excised and fixed in 10% buffered neutral formalin. Sections of formalin-fixed, paraffin-embedded tissues were cut to 5 μm. Slides were stained with an EPB1 antibody (Upstate) diluted 1:50 using the standard avidin-biotin method (Vector Labs, Burlinghame, Calif.). Peroxidase activity was localized by the diaminobenzidine tetrachloride peroxidase reaction with Harris hematoxylin as a counterstain.

Measurement of PSA levels: Serum PSA levels were determined using a PSA ELISA kit from DSL, Inc (Webster, Tex.). Briefly, 25 μl of serum diluted in 1:5 in DPBS or conditioned media was mixed with assay buffer to a final volume of 75 μl and added to duplicate wells in the 96 well plates that had been coated with an anti-PSA antibody. Following a 1 h incubation and extensive washing of the plate, the wells were treated for 30 min with a second anti-PSA antibody labeled with horseradish peroxidase. After washing, the wells were treated with a tetramethylbendizine substrate for 10 min, and absorbance was read at 450 nm.

Statistical Analysis: Results of growth and luciferase assays were analyzed using a two-tailed Students t-test. Significance was established at P<0.05. The proportion of growing tumors in control versus EPB1 transfectants and the rate of growth were tested using Fisher's exact test, two-sided. AP<0.05 was considered to be statistically significant.

Ectopic expression of EPB1 downregulates androgen-regulated genes: Gene expression profiling of LNCaP cells stably transfected with EBP1 was used to determine the range of androgen-dependent genes affected by EPB1 overexpression. These cells overexpress EPB1 protein between two- and three-fold (Zhang et al., 2002, Repression of Androgen Receptor Mediated Transcription by the ErbB-3 Binding Protein EPB1, Oncogene, 21: 5609-5618). Changes in gene expression were measured using microarray analysis of 33,000 transcripts on the Affymetrix U133A chip. To compile a list of differentially regulated genes, only those genes that were activated or repressed at least 3-fold (p<0.05, 500 minimum expression units) were included. Of 8,000 genes that were evaluable, the expression of 167 genes was found to differ significantly between the two cell lines. Forty-one genes were induced and 126 were repressed. Seventy-two of these genes have HUGO approved names. Six androgen-responsive genes were found to be downregulated at least three-fold in EPB1-overexpressing cells as compared to controls. These include the Androgen Receptor (3.7 fold decrease), PSA (3.7 fold decrease) as previously reported (Zhang et al., 2002, Repression of Androgen Receptor Mediated Transcription by the ErbB-3 Binding Protein EPB1, Oncogene, 21: 5609-5618), Kallikrein 2 (3.2 fold decrease), POV-1 (5.0 fold decrease), TMPRSS2 (3.2 fold decrease), and prostate-derived factor (3.2 fold decrease). The Kallikrein 2 gene is regulated by AR, predominantly expressed in prostate tissue, secreted by LNCaP cells, and 78% homologous to PSA. The potential value of Kallikrein 2 in prostate cancer detection is strongly suggested by recent studies (Partin et al., Use of Human Glandular Kallikrein 2 for the Detection of Prostate Cancer: Preliminary Analysis, Urology, 54:839-845). The POV-1 gene encodes a transcript for a novel L amino acid transporter (Babu et al., 2003, Identification of a Novel System L Amino Acid Transporter Structurally Distinct from Heterodimeric Amino Acid Transporters, J. Biol. Chem., 278:43838-43845) that was found to be upregulated in aggressive prostate carcinoma (Chuaqui et al., 1997, Identification of a Novel Transcript Up-Regulated in a Clinically Aggressive Prostate Carcinoma, Urology, 50:302-307). The TMPRSS2 gene is androgen-regulated and also highly expressed in prostate and prostate cancer (Afar et al., 2001, Catalytic Cleavage of the Androgen-Regulated TMPRSS2 Protease Results in its Secretion by Prostate and Prostate Cancer Epithelia, Cancer Res., 61:1686-1692). Prostate-derived factor, a member of the bone morphogenetic protein family, also has been shown to be androgen-regulated and is expressed in high levels in the prostate (Paralkar et al., 1998, Cloning and Characterization of a Novel Member of the Transforming Growth Factor-Beta/Bone Morphogenetic Protein Family, J. Biol. Chem., 273:13760-13767).

The results of the microarray analysis were validated using real-time quantitative reverse-transcription PCR, Western blot, and ELISA methods. Real-time PCR methods indicated that AR mRNA was down-regulated more than 2-fold in EPB1 transfectants. Western blot analysis indicated that AR protein was decreased more than five-fold in LNCaP EPB1 transfectants. The expression of POV-1 mRNA and protein were each decreased about two-fold. PSA secretion in the conditioned media of EPB1 and vector control cells was assessed by ELISA. Levels of secreted PSA in the control cells were similar to those previously reported (Lee et al., 1995, Regulation of Proliferation and Production of Prostate-Specific Antigen in Androgen-Sensitive Prostatic Cancer Cells, LNCaP, by Dihydrotestosterone, Endocrinology, 136: 796-803). Results showed that secreted PSA protein was downregulated 10-fold in EPB1 transfectants as compared to controls. Finally, kallikirein-2 mRNA expression was decreased approximately 40%.

Chromatin immunoprecipitation experiments were conducted. EPB1 transfectants were serum-starved and then treated with bicalutamide for one hour. HDAC2 was recruited to the PSA promoter after exposure to bicalutamide as previously reported (Shang et al., 2002, Formation of the Androgen Receptor Transcription Complex, Mol. Cell, 9:601-610). EPB1 was not associated with the promoter in the absence of bicalutamide, but was recruited to the PSA promoter after bicalutamide exposure.

The data indicating that EPB1 is recruited to the PSA promoter in the presence of biclautamide suggest that EPB1 may be involved in the response to anti-androgens and play a role in the development of the androgen-independent phenotype. The presence of EPB1 was assayed in models of androgen independence. The C-81 LNCaP subline has been made androgen-independent by continuous high level passage in complete media (Igawa et al., 2002, Establishment and Characterization of Androgen-Independent Human Prostate Cancer LNCaP Cell Model, Prostate, 50:222-235). The LAPC-4 model has been extensively characterized as to its ability to recapitulate the progression of prostate cancer. This xenograft has wild-type AR receptor and grows as androgen-dependent cancers in male SCID mice. These tumors regress in response to androgen ablation but eventually regrow as androgen-independent tumors that overexpress ErbB2 (Klein et al., 1997, Progression of Metastatic Human Prostate Cancer to Androgen Independence in Immunodeficient SCID Mice, Nat. Med., 3:402-408). LAPC xenografts that were grown in either intact or castrated mice were also examined. The results indicated that expression of EPB1 protein was decreased in both C-81 and LAPC androgen-independent sublines.

Growth Characteristics of LNCaP EPB1 transfectants: The growth rate of the EPB1-transfected cells in complete media was compared to that of cells transfected with the empty vector. The growth rate of the EPB1 transfectants was significantly decreased ($p<0.05$) as compared with that of the vector control. The doubling time for EPB1 transfectants increased to 72 hours from 48 hours for the vector control line.

The soft agar growth of EPB1 transfectants was also examined. LNCaP vector controls and EPB1 transfectants were seeded at concentrations between $1\times10^4$ and $1\times10^5$ cells per dish and colony growth in soft agar assessed ten days later. Ectopic expression of EPB1 decreased colony growth approximately 90% at the highest cell concentration tested.

The sensitivity of EBP1 transfectants to DHT was also examined. Both LNCaP vector controls and EPB1 transfectants were placed in serum-free media and then stimulated with DHT. The growth of the vector controls was inhibited approximately 70% by the withdrawal of androgens as previously reported (Igawa et al., 2002, supra). The growth of EBP1 transfectants was inhibited 60%. Thus, EBP1 transfectants had not become androgen-independent. As previously reported (Igawa et al., 2002, supra), DHT at increasing concentrations stimulated the growth of LNCaP vector controls with a maximal 250% stimulation at $10^{-9}$ M DHT as compared to no DHT. In contrast, DHT at $10^{-9}$ M only slightly (35%) stimulated the growth of EBP1 transfectants.

The effect of the anti-androgen bicalutamide on DHT-stimulated growth was also examined. The DHT-stimulated growth of both LNCaP vector controls and EBP1-transfected cells was completely suppressed by 10 µM bicalutamide.

The effect of the stable overexpression of EPB1 on the transactivation of the MMTV-luciferase (MMTV-luc) reporter gene induced by R1881 and the partial agonist cyproterone acetate was also analyzed. Addition of R881 ($10^{-8}$ M) led to a 20-fold activation of luciferase activity of LNCaP vector controls. Cyproterone acetate ($10^{-7}$ M) induced a 5-fold activation of the AR as previously reported (Dotzlaw et al., 2002, The Amino Terminus of the Human AR is Target for Corepressor Action and Antihormone Agonism, Mol. Endocrinol, 16:661-673) and enhanced the transcriptional response in the presence of R1881. In contrast, neither R1881 nor cyproterone acetate nor the combination thereof stimulated AR activation in EPB1 transfectants.

The effect of a range of concentrations of cyproterone acetate on AR transactivation was also examined. LNCaP vector controls and EBP1 transfectants were transfected with the MMTV-luc reporter and their response to increasing concentrations of cyproterone acetate was tested. Cyproterone acetate induced activation of AR at concentrations of $10^{-6}$ to $10^{-8}$ as previously reported (Veldscholte et al., 1990, A Mutation in the Ligand Binding Domain of the Androgen Receptor of Human LNCaP Cells Affects Steroid Binding Characteristics and Response to Anti-Androgens, Biochem. Biophys. Res. Commun., 173:534-540). In contrast, cyproterone acetate failed to induce activation of the AR in the EPB1 transfectants at any concentration tested.

Results

EPB1 expression suppresses growth of prostate cancer xenografts: The effect of ectopic expression of EPB1 on the tumorigenicity of LNCaP cells was examined. EBP1- and vector-transfected cells were injected subcutaneously into SCID mice, and tumor growth was monitored. Tumor growth was first noted in both groups at day 20. However, on day 20, tumors were observed at only 10% of the EBP1 inoculation sites, as opposed to 35% of the sites for vector controls. At the end of the study, tumors had developed at more than 85% of the sites injected with the vector control cells, while less than 40% of sites inoculated with EBP1 transfectants developed tumors. This difference was significant at $p=0.04$ by Fisher's exact test, two-sided. The average tumor volumes were also significantly different between the EPB1 transfectants and vector controls. Average tumor volumes observed at the end of the study were $268\pm70$ mm$^3$ as compared with $1214\pm168$ mm$^3$ for the vector controls ($p=0.0003$). In addition, the growth rate was also slower for EPB1 transfectants at all time points measured ($p=0.0001$). Immunohistochemical staining of tissue sections of the tumors indicated that EPB1 expression was equivalent in both groups. Real-time PCR of EPB1 mRNA extracted from the tumors showed no change between the two groups. Thus, cells that grew to form tumors had lost overexpression of the transgene.

Thus, EPB1, an ErbB3 binding protein, is a potent repressor of AR signaling. Gene expression profiling identified that a cohort of AR target genes, potentially involved in androgen-independent growth of prostate cancer cells, was down-regulated in cells with only moderate EPB1 expression as compared with the vector-transfected cells. These results were validated by Real-Time Quantitative RT-PCR, Western blot and ELISA assays. Therefore, an AR corepressor can downregulate levels of AR protein.

A reduction in AR activity or expression appears to be a key component of prostate cancer treatment. Overexpression of an AR corepressor, EPB1, reduces AR protein levels and transcripton of AR-regulated genes in LNCAP cells, resulting in a less tumorigenic phenotype. In addition, endogenous EPB1 expression was lost in two different models of androgen-independent prostate cancer growth.

Restoration or increase of EPB1 expression can sensitize the androgen independent prostate cancer C81 cells to radiation. Radiotherapy is another important treatment for locally and regionally advanced prostate cancer. However, resistance of prostate cancer cells to radiation limits its efficacy and dose escalation is obviously not the solution to this common phenomenon. Bcl-2 overexpression may be the same critical molecule underlying the resistance to radiotherapy as to the chemotherapy in prostate cancer. 4 Gy gamma radiation killed 100% of EPB1 transfectants while less than 10% of C81 vector transfectants were dead in 72 h after exposure to the same 4 Gy gamma irradiation. These results demonstrate that EPB1 can sensitize cells to radiation. Without being bound by theory, it is contemplated that the increase in sensitivity to radiation might be due to the decreased levels of Bcl-2 in EPB1 transfectants given the importance of Bcl-2 function in resistance to radiation.

Example 2

EBP1, an ErbB3-Binding Protein, is Decreased in Prostate Cancer and Implicated in Hormone Resistance Summary Aberrant activation of the androgen receptor (AR) by the Erb2/ErbB3 heterodimer contributes to the development of hormone resistance in prostate cancer. EBP1, an ErbB3 binding protein, also acts as an AR corepressor. Because Ebp1 is decreased in preclinical models of hormone refractory prostate cancer, the expression of EBP1 in human prostate cancer was studied. The expression of the EBP1 gene was found to be significantly decreased in prostate cancer patients as compared with those with benign disease at both the mRNA and protein levels. Restoration of EBP1 expression in the hormone refractory C81 cell line led to an amelioration of the androgen independent phenotype based on established biological criteria and a reduction in the expression of a cohort of AR target genes. The ability of the Erb3 ligand Heregulin (HRG) to stimulate growth and AKT phosphorylation, observed in hormone refractory prostate cancer cells, was abolished in C81-EBP1 transfectants. Abrogation of EBP1 expression by shRNA in hormone dependent LNCaP cells resulted in aberrant HRG-stimulated cell growth and AKT phosphorylation. Restoration of EBP1 expression decreased the tumorigenicity of C81 xenografts in female mice and elimination of EBP1 expression enhanced the ability of LNCaP cells to grow in female mice. These data support a role for EBP1 in preventing the development of hormone refractory prostate cancer via inhibition of both AR signaling and HRG-stimulated growth and AKT signaling.

Introduction

The development of hormone refractory disease is a determinant of poor prognosis in prostate cancer. As extensive data indicate that AR is responsible for development of hormone resistance (I; 2), downregulation of AR expression and activity has been proposed as a critical component in treatment of advanced prostate cancer (3). ErbB family members and their ligands have been implicated in the development of androgen independence due to their stimulatory effects on AR function (4; 5). The ways in which the ErbB2/ErbB3 pathway influences the AR axis is an area of intense investigation.

EBP1, a protein that binds both the ErbB3 receptor and the AR, has been cloned and characterized. EBP1 is the human homologue of the mouse cell cycle regulated, DNA binding protein p38-2G4, the product of the PA2G4 gene (6). EBP1 has several important structural motifs including a predicted amphipathic helical domain for protein/protein or protein/DNA interactions and an LXXLL motif flanked by basic regions present in many nuclear receptor binding proteins (7). EBP1 physically associates with AR and suppresses AR signaling (8). Overexpression of the EBP1 gene in androgen dependent LNCaP cells downregulates expression of AR and its target genes. This results in cell growth inhibition, reduced PSA secretion and retardation of tumor growth in an animal model. EBP1 expression is reduced in two models of hormone refractory prostate cancer (9).

The ErbB3/4 ligand heregulin (HRG) is an important modulator of growth of prostate cancer cells. HRG inhibits growth and induces differentiation of hormone dependent AR positive, ErbB1-3 positive LNCaP cells (10; 11; 12). In contrast, HRG triggers the growth of hormone refractory, AR positive, ErbB 1-3 positive prostate cancer cells and induces AKT activation (13; 14). It has been previously demonstrated that Ebp1 associated with the cytoplasmic domain of ErbB3 in LNCaP cells in the absence of HRG, but dissociated from ErbB3 upon HRG stimulation. HRG treatment enhanced both the association of Ebp1 with the AR and the ability of Ebp1 to repress AR transactivation (9). These studies suggested that EPB1 may be a downstream effector of HRG action in prostate cancer cells.

In the present study, the effects of EBP1 on the hormone refractory phenotype in prostate cancer cells were determined. Increased expression of EBP1 in C81 cells led to an amelioration of the androgen independent phenotype via inhibition of both AR signaling and the PI3K/AKT pathway. Knock down of EBP1 expression in hormone dependent LNCaP cells led to a hormone resistant phenotype. These studies suggest the role of EBP1 as an endogenous negative regulator of hormone refractory prostate cancer.

Methods

Cell culture. All cell lines were obtained from the American Type Culture Collection (Manassas, Va.) and were routinely cultured in RPMI 1640 medium supplemented with 10% FBS.

Creation of stably transfected cell lines. Subconfluent C81 cells in 100-mm tissue culture dishes were transfected with 10 μg of CMV-10 or CMV10-EBP1 expression plasmids using FuGENE®-6 according to the manufacture's protocol. Cells were selected in G418 (800 μg/ml) for 5 weeks and resistant colonies expanded. Both individual clones and mass transfectants were obtained.

To generate Ebp1 silenced cell lines, LNCaP cells were seeded into 96 well plates and transduced with $10^6$ transducing units of lentiviral particles corresponding to different shRNA constructs targeted to the PA2G4 (EBP1) gene (Mission shRNA, Sigma, St. Louis, Mo.) according to the manufacturer's protocol. Cell lines were selected in 2 μg/ml of puromycin and surviving colonies of cells expanded as mass cultures. Five individual shRNA lentiviral particle constructs were tested. Only one construct (13C) corresponding to NT 302-322 of pa2g4 (Genbank NM_006191.1) inhibited Ebp1 expression. Another construct, 16A, did not inhibit Ebp1 expression and served as a control in the experiments cited.

Microarray Analysis and Bioinformatics. RNA was prepared using the Trizol Reagent as previously described (8). Microarray processing and data analysis was performed at Genome Explorations (Nashville, Tenn.). U133A oligonucleotide arrays (Affymetrix) containing ~33,000 full length annotated genes together with additional probe sets designed to represent EST sequences were used for the analysis. Only genes with a minimum expression level of 500 were included in this analysis. Genes whose expression varied more than three fold with a p value of <0.05 were considered to be significantly different between the two cell lines. Oncomine analyses were performed by using Oncomine 3.0 (www.oncomine.org).

Real Time Quantitative Reverse-Transcription PCR. Both cell culture samples and a commercial panel of cDNAs from normal prostate and prostate tumors (TissueScan, Origene, Rockville, Md.) were examined. The method of Nakanishi et al. (15) was used as previously described. Real-time quantitative RT-PCR was performed on the LightCycler® (Roche) platform. The following forward and reverse primers were selected using Primer Express software and synthesized by the Core Laboratory of University of Maryland School of Medicine: Ebp1, sense: 5'-GCA CGC CAA TAG AAG G-3' (SEQ ID NO: 16) and antisense: 5'-GTA AAC GGC ATG GCA TC-3' (SEQ ID NO: 17) kallikrein-2 sense: 5'-CAT CCA GTC TCG GAT TG-3' (SEQ ID NO: 18) and antisense: 5'-CTC ATA TTG TAG AGC GGG T-3' (SEQ ID NO: 19), TSPY, sense: 5'-CAG GGC TTC TCA TTC CAC TC-3' (SEQ ID NO: 20) and antisense: 5'-CCA TCA TAT TCA ACT CAA CAA CTGG-3' (16; SEQ ID NO: 21), AGR2, sense: 5'-ATT GGC AGA GCA GTT TCT CC-3' (SEQ ID NO: 22) and antisense, 5'-GAG CTG TAT CTG CAG GTT CGT (17; SEQ ID NO: 23) 13-Actin, sense: 5'-GCT ATC CAG GCT GTG CTA TC-3' (SEQ ID NO: 24) and antisense 5'-TGT CAC GCA CGA TTT CC-3' (SEQ ID NO: 25). A SYBR®Green PCR Kit was used as per the manufacturer's instructions (Applied Biosystems, Foster City, Calif.) and the analyses were performed in duplicate or triplicate.

Target mRNA values were normalized using β-actin mRNA as an internal control. The relative quantitation of gene expression was performed using the comparative ΔΔ Ct (threshold method) using 913-actin as an internal control.

Tissue Microarray and Immunohistochemical Analysis

An intermediate density tissue microarray from patients with prostate cancer and one from normal prostate and patients with benign prostatic hyperplasia (BPH) was received from the Cooperative Prostate Cancer Tissue Resource (CPCTR; NC). For the benign group, fifteen normal prostate tissues taken from prostate cancer patients and 27 prostate tissues from normals were used. For the malignant group, 153 tumors from patients with both localized and metastatic prostate cancer (Gleason grades 4-10) were evaluated. The VECTASTAIN® Elite ABC kit, purchased from Vector Laboratories, (Burlingame, Calif.) was used for immunohistochemical analysis. Briefly, slides were deparaffinized with xylene and rehydrated through graded alcohol washes. Slides were then incubated in 0.3% hydrogen peroxide for 30 mm to quench endogenous horseradish peroxidase. The slides were then blocked by incubation in normal goat serum (dilution 1:10) followed by incubation for 60 mm with anti Ebp1 antibody (Upstate 1:200) in PBS (pH 7.4) as previously described (18). Slides were then treated with biotin labeled anti rabbit IgG and incubated with preformed avidin-biotin peroxidase complex. Finally sections were counterstained with hematoxylin, dehydrated and mounted. Immunohistochemical staining was assessed independently by two observers and a consensus of grading was reached. Immunostaining was evaluated manually and graded using a two score system based on intensity score and proportion score. Intensity was scored on the following scale: 0=negative, 1=weak, 2=moderate, 3=strong. Distribution of immunopositive tumor cells was scored on a scale of 0 (0%), 1 (1-25), 2 (25-50), 3 (40-75), 4 (75-100). The immunoreactivity score was determined by the sum of intensity score and proportion score. The nonparametric Wilcoxon rank sum test was conducted to determine significant differences between the benign prostate epithelium and the malignant tissue.

Measurement of PSA levels. Serum PSA levels were determined using a PSA ELISA kit from DSL, Inc (Webster, Tex.) as previously described (9).

Western Blot Analysis. Western blot analysis was performed as previously described (19). The Ebp1 antibody was from Upstate (Lake Placid, N.Y.), the polyclonal antibody to actin from Sigma, the AKT and phospho AKT antibodies from Cell Signaling (Beverly, Mass.) and the AGR2 antibody was previously described (20)

Cell Growth Assays Cell growth measurement in complete media was performed as described using a hemocytometer (21). For soft agar growth assays, increasing concentrations of cells (as indicated) were plated in 35 mm Petri dishes in 0.3% agar in complete media and colonies were counted after 10 days of incubation (21). For studies assessing the effect of DHT, HRG or chemotherapeutic agents on cell growth, cells ($5 \times 10^3$) were plated in 96 well plates in complete media. After a 24-hour attachment period, the medium was replaced with steroid free medium [phenol red free RPMI 1640 and 5% charcoal stripped fetal bovine serum (Sigma)]. After 48 hours of steroid depletion, cells were refed with fresh steroid reduced medium with or without the indicated concentrations of DHT, bicalutamide (Casodex) (10 μM), HRG or the chemotherapeutic drugs at the concentrations indicated. Relative cell growth was determined using a Promega Proliferation Reagent (Promega, Madison Wis.) as per manufacturer's instructions with absorbance being read at 490 mm using a Dynex plate reader.

Luciferase Reporter Assays Cells ($5 \times 10^4$) were plated in 12 well plates in complete media. When cells reached 50-60% confluence, they were transfected using the FuGENE®-6 Reagent (Roche, Indianapolis, Ind.) according to the manufacturer's instructions. Cells were transfected with 0.5 μg of an MMTV-luciferase reporter plasmid and 5 ng of a TK *Renilla* plasmid (Promega, Madison, Wis.) as an internal control. Complete medium was replaced 24 h after transfection with phenol red free RPMI 1640 with CSS with or without R1881 ($10^{-8}$M). Luciferase activity was determined using the Promega Dual luciferase assay kit as described by the manufacturer.

In Vivo Studies in Athymic Mice Female nude athymic NCr-nu/nu mice, 4-6 weeks of age, were purchased from the National Cancer Institute (Frederick, Md.). Animals were housed in a pathogen free environment under controlled conditions of light and humidity and received food and water ad libitum. Cells were suspended in Matrigel™ (10 mg/ml) (Collaborative Research, Waltham Mass.) at $1.5 \times 10^7$ cells/ml. Each mouse received subcutaneous injections at one site on each flank with 300 μl of cell suspension. Tumors were measured with calipers. Tumor volumes were calculated by the formula width$^2$×length/2 b×b×1/2. Mean tumor volume±S.D. were calculated and plotted against time. The animal protocol was approved by the Institutional Animal Care and Use Committee at the University of Maryland.

Statistical Analysis Results of growth assays were analyzed using a two-sided Students t-test. Significance was established at P<0.05. The proportion of developed tumors in control and EBP1 transfectants was compared using Fisher's exact test. All hypothesis tests were two-sided. The different groups were compared at the 0.05 level of significance.

Results

Reduced Expression of the Ebp1 Gene in Prostate Cancer Patients

Figure 3B:
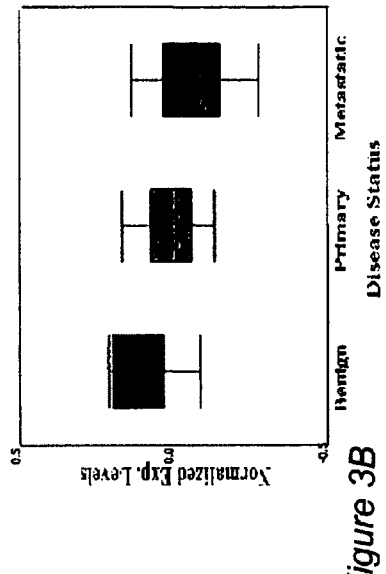
FIG. 3A-D. EBPI expression is decreased with prostate cancer progression. A. Quantitative RT-PCR was performed for EBP1 mRNA expression on a panel of benign [normal (7) BPH (11)] prostate cancer Stage I and II (21), and prostate cancer Stage III and IV (9) tissues obtained from Origene. The relative levels of all test mRNAs were normalized to β actin. B. A public data set was obtained and processed by Oncomine 3.0 for EBP1 expression. The average gene expression level at three different stages (Benign n=23, Primary n=64, and Metastatic n=25) of the disease is presented. C. Boxplots of immunohistochemical staining intensity of normal prostate tissue (n=40) or tissue from patients with prostate cancer (n=148). D. Representative staining of normal prostate epithelium (left panel), Grade 7 Gleason (middle panel) showing nuclear staining or a prostate tumor, Gleason grade (right panel).
Figure 3A:
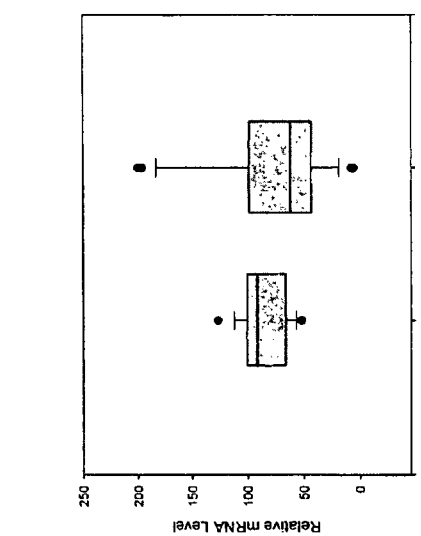
Figure 3D:
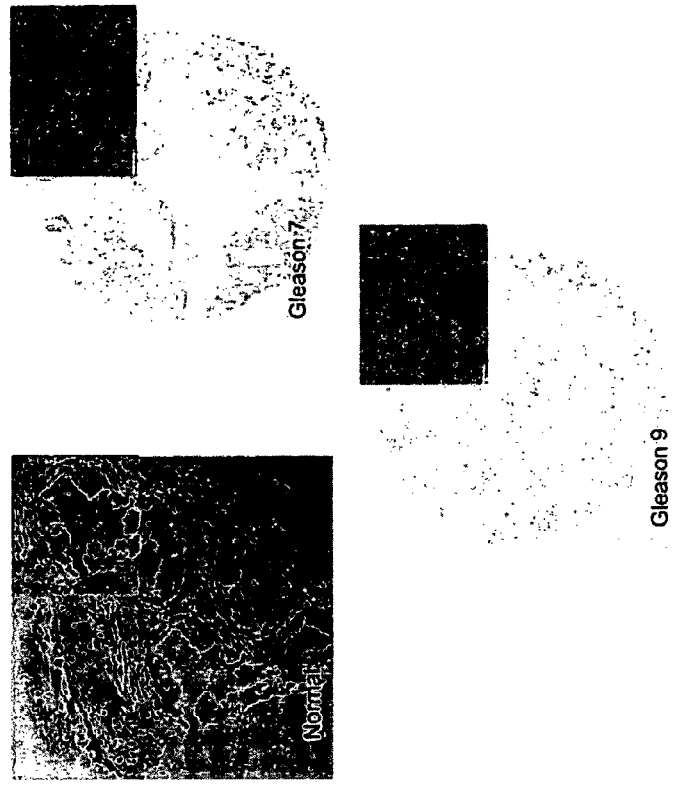
Figure 3C:
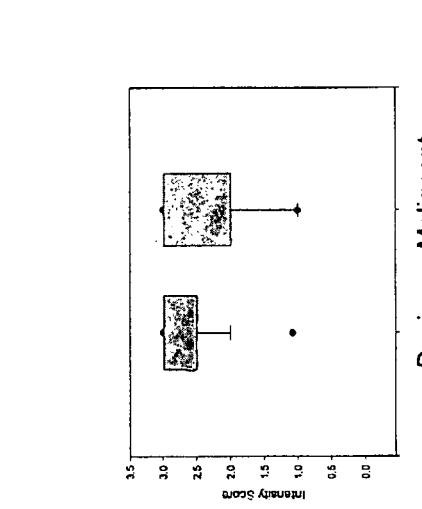

Since reduced expression of EPB1 had been found in preclinical models of prostate cancer (9), a commercially prepared cDNA panel consisting of nonpaired benign prostate and prostate tumor samples was also screened. EBP1 was significantly decreased (p<0.03) in prostate cancers as compared with normal tissue (FIG. 3A). The expression of the EBP1 (PA2G4) gene in patients was then determined using public gene expression data bases. Oncomine analysis of a data set posted by Yu et al (22) revealed that PA2G4 was significantly down-regulated in prostate tumors relative to normal prostate samples (P<0.00001) and further down-regulated in metastases (P<0.00001) (FIG. 3B). The studies of Vanaja et al. (23) (P<0.05), Singh et al (24) (P<0.1), and LaTulippe et al (25) (P<0.01) also indicate that EBP1 expression is similarly decreased (data not shown). To examine the expression of EBP1 protein in human prostate tumor tissues, immunohistochemical analysis was done on a tissue array containing benign (n=40) and prostate cancer (n=148) specimens. EBP1 staining intensity was decreased in the cytoplasm of the prostate tumor samples as compared with the benign samples (2.73 vs. 2.11) (p<0.002) (FIG. 3C). EBP1 staining was predominantly detected in the cytoplasm of both normal epithelial and prostate tumor cells (FIG. 3D). Nuclear and cytoplasmic staining was observed in 30% of prostate cancer specimens (FIG. 3D, middle panel), but not in benign tissue. This resembles the nuclear and cytoplasmic distribution of EBP1 observed in cell culture (19; 26; 27) (FIG. 3D).

Increased Expression of Ebp1 in Hormone Refractory C81 Cells Ameliorates the Hormone Refractory Phenotype To analyze whether the increased expression of EBP1 could ameliorate the hormone refractory phenotype, FLAG-EBP1 or empty vector stably transfected C81 cell lines were established. EBP1 expression was increased approximately three fold (FIG. 4A) in EBP1 transfectants. EBP1 transfectants were then examined based on established biological criteria for androgen independence (1): growth rate, response to hormones and chemotherapy. The growth rate of the EBP1 transfectants in complete media was significantly decreased (p<0.05) as compared with that of the vector control (FIG. 4A, left panel). Ectopic expression of EBP1 also decreased colony growth in soft agar approximately 50% at the highest cell concentration tested (FIG. 4A, right panel).

Androgen independent cells in culture can be either refractory to hormone stimulation or sensitized to low doses of hormone. In comparison to the parental LNCaP cells, C81 cells are no longer growth stimulated by DHT (28). The growth of EBP1 transfectants was found to be reduced to one third of that of the vector controls in the absence of androgens (data not shown). The vector control C81 cells were unresponsive to androgen (FIG. 4B, left panel) as previously reported (28). In contrast, EBP1 transfected C81 cells responded to androgen in a similar manner as the original low passage LNCaP androgen sensitive cells (FIG. 4B, left panel) (28). To determine if the androgen-stimulated growth of the EBP1 transfected cells was mediated via the AR, the effect of the anti-androgen bicalutamide (Casodex) on DHT stimulated growth was examined. The DHT-stimulated growth of the EBP1 transfected cells was suppressed by 10 μM bicalutamide (FIG. 4B, right panel), suggesting that the increased growth in the presence of androgens was mediated via the AR.

A combination of Mitoxantrone and Docetaxel is currently the standard palliative treatment in hormone-refractory prostate cancer patients (29). C81 cells were relatively refractory to Docetaxel in androgen deprived conditions as previously reported (30), but EBP1 transfected cells were significantly more sensitive to 5-20 nM of Docetaxel under these same conditions (FIG. 4C, left panel). The sensitivity of both vector control and EBP1 transfectants to Mitoxantrone plateaued at 20 nM. However, growth of EBP1 transfectants was decreased approximately 80% as opposed to 40% for the vector controls at this concentration (FIG. 4C, right panel). In contrast, the sensitivity of the EBP1 transfectants to both drugs was the same as vector controls when cells were grown in complete media (data not shown).

Figure 5A:
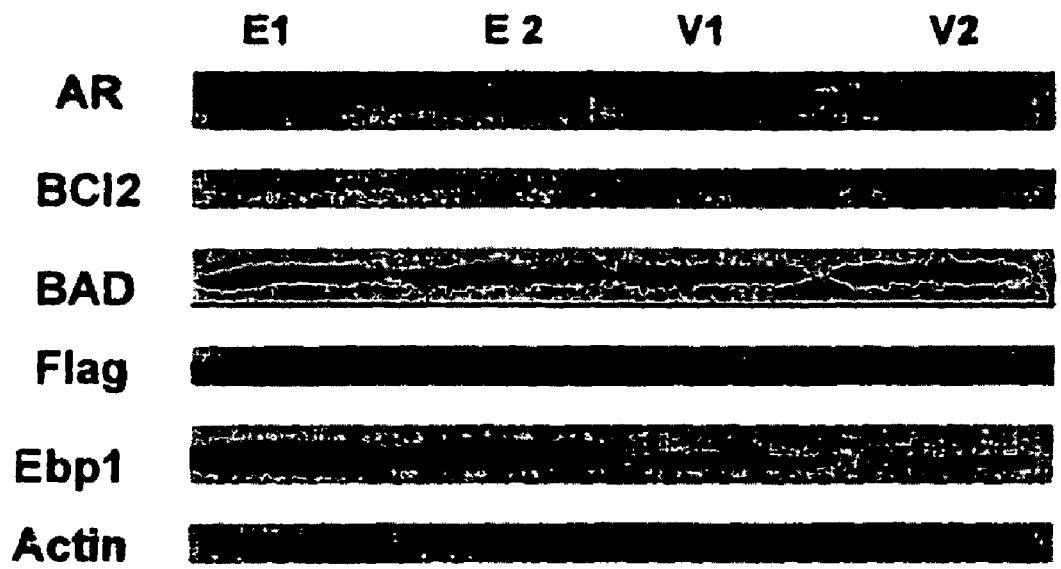
FIG. 5A-D. Expression of genes associated with androgen independence is decreased in C81 EBP1 transfectants. A. Lysates of logarithmically growing clones of C81 EBP1 transfectants (E1,2) or vector controls (V 1,2) were resolved by SDS-PAGE and immunoblotted for AR, BCL-2, BAD, FLAG, EBP1 and ACTIN as indicated. Representative of 3 experiments. B. Secreted PSA as measured by ELISA. EBP1 and vector control cells were plated at $1 \times 10^6$ cells/100 mm dish in complete media. Forty-eight hours later, conditioned media were collected and frozen. PSA activity was assessed by ELISA. Levels of PSA were adjusted to total cell number. Data is representative of 2 experiments. C. Validation of mRNA levels in EBP1 transfectants. Quantitative RT PCR was performed for the KALLIKREIN-2, AGR2 and TSPY genes in EBP1 and vector transfectants. The relative levels of all test mRNAs were normalized to β-ACTIN. Results are representative of 3 experiments using different sets of cells. D. Expression of AGR2 protein in vector and EBP1 C81 transfectants. Lysates of vector control (V) or EBP1 (E) transfected cells grown in complete media were resolved by SDS-PAGE and analyzed by Western blotting with antibody to AGR2.

Restoration of Ebp1 Protein Levels Significantly Reduces Expression of Molecules Associated with the Androgen Refractory Phenotype To elucidate how restoration of EBP1 gene expression in C81 cells mitigates the hormone refractory phenotype, the expression levels of proteins that play a key role in androgen independence was examined. Western blot analysis of two individual C81 clones stably transfected with a FLAG-tagged EBP1 or vector controls (FIG. 5A) showed that ectopic expression of EBP1 markedly reduced the protein levels of AR, consistent with our previous report for LNCaP cells (9), and Bcl2, another molecule associated with the androgen independent phenotype (31). In contrast, the level of the proapoptotic protein BAD remained the same as the vector controls.

Next, a microarray analysis of mass transfected EBP1 and vector transfected C81 cell lines was conducted to determine the spectrum of differentially expressed genes contributing to the hormone refractory phenotype. Six AR target genes potentially involved in androgen independent growth were found to be downregulated at least three fold in EBP1 overexpressing cells as compared to controls (Table 1). These include PSA (kallikrein 3), Kallikrein 2, TMPRSS2, and Prostate differentiation factor as previously reported for LNCaP cells (9). In addition, the expression of the AR regulated gene AGR2 (20) and the candidate oncogene TSPY (Testis-specific protein, Y-encoded) (16) was significantly down regulated in the EBP1 transfectants.

TABLE 1

Androgen Regulated Genes Decreased in EBP1 transfected C81 cells*

| Accession No. | Gene Name | Fold Decrease | P value |
|---|---|---|---|
| NM_003308 | TSPY | 9.5 | .002 |
| AF088867 | AGR2 | 7.1 | .0002 |
| NM_003527 | Prostate Cancer overexpressed POV | 5 | .001 |
| UI7040 | Prostate Specific Antigen | 5.5 | .001 |
| BCOO5 196 | Prostatic Kallikrein 2 | 5.4 | .004 |

TABLE 1-continued

Androgen Regulated Genes Decreased in EBP1 transfected C81 cells*

| Accession No. | Gene Name | Fold Decrease | P value |
|---|---|---|---|
| AF003934 | Prostate Differentiation Factor mRNA | 5.4 | .0002 |
| AF2700487 | Androgen regulated serine protease TMPRSS2 | 4.0 | .01 |

*A microarray analysis of EBP1 transfected and vector control cells was performed as described in the Materials and Methods. The expression of 67 genes (minimum of 3 fold change) was found to differ significantly between the two cell lines. Twenty-two genes were induced and 45 were repressed. AR signaling associated genes are presented in the Table.

Figure 5B:
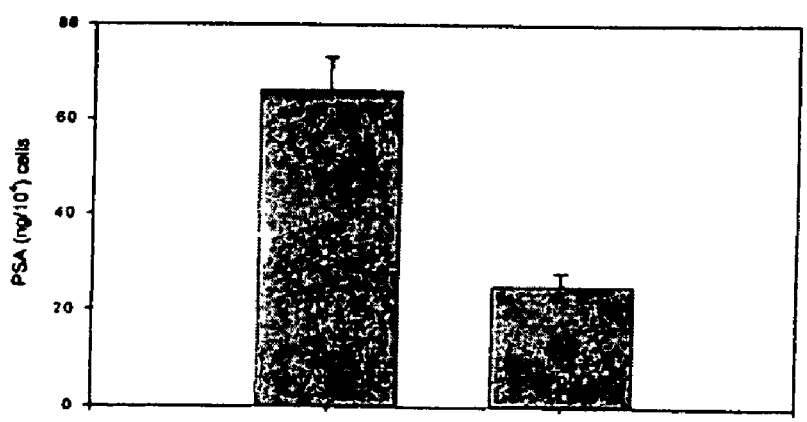
Figure 5C:
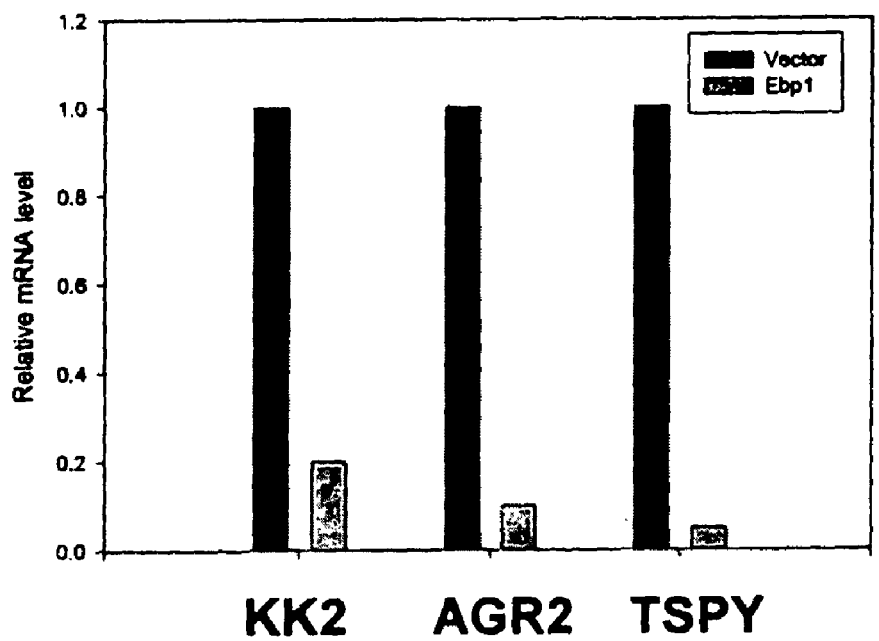
Figure 5D:
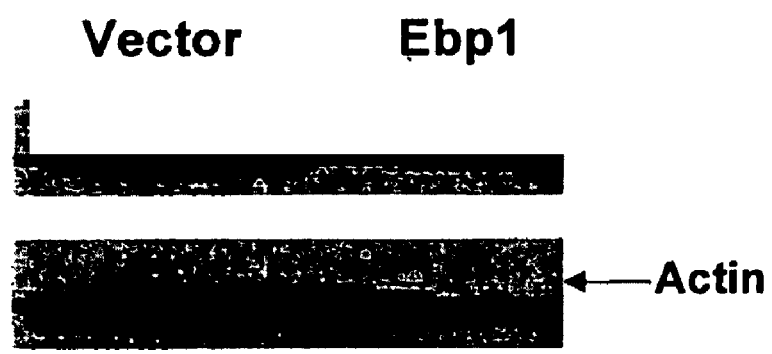

Real time quantitative RT-PCR, Western blot and ELISA methods were employed to validate four representative genes whose expression is associated with prostate cancer progression. As circulating PSA levels serve as a marker for the hormone-independent growth of prostate cancer (32), PSA secretion into the conditioned media of Ebp1 and vector control cells was assessed by ELISA. Secreted PSA protein levels were decreased 60% in EBP1 transfectants as compared to C81 vector controls (FIG. 5B). The Kallikren 2 gene is regulated by AR and is being evaluated as a marker for prostate cancer progression (33). Real time RT-PCR methods indicated that Kallikrein-2 mRNA was downregulated over 80% in EBP1 transfectants as compared with vector controls (FIG. 5C). TSPY mRNA was also downregulated over 90%. AGR2, the human homologue of the *Xenopus* anterior gradient 2 gene, is regulated by AR and its overexpression is associated with enhanced metastasis (34). Real time RT-PCR indicated that AGR2 mRNA was downregulated over 90% in EBP1 transfectants as compared with vector controls (FIG. 5C). Western blot analysis detected decreased AGR2 protein in C81 EBP1 transfectants growing in complete media (FIG. 5D).

Restoration of EBP1 Expression Blocked HRG-Activated PI3KlAKT Signaling

HRG activated pathways can contribute to ligand independent activation of AR (1). The ability of EBP1 to affect the responsiveness of C81 androgen independent cells to HRG was examined. As previously noted (FIG. 3D), growth of EBP1 transfectants in androgen depleted media was reduced by 2/3 as compared with vector transfected controls (FIG. 6A). HRG induced the growth of vector control C81 cells in androgen-free media as expected (13). However, the ectopic expression of EBP1 completely abrogated the ability of C81 cells to grow in response to HRG (FIG. 6A).

As restoration of EBP1 expression inhibited HRG-induced growth, the ability of EBP1 to attenuate HRG signaling was examined. HRG-induced AKT phosphorylation and activation is important in growth of androgen independent cells (35; 36) and inhibition of AKT phosphorylation delays the transition to androgen independence (37). AKT was basally phosphorylated in C81 vector and EBP1 transfected cells as expected (FIG. 6B), presumably due to loss of PTEN expression (38). Densitometry indicated that I-IRG induced a 4 fold increase in AKT phosphorylation at 5 mm that gradually declined in vector control cells (FIG. 6C). In contrast, HRG failed to induce an increase in AKT phosphorylation in EBP1 transfectants.

Abrogation of EBP1 Protein Expression by shRNA in LNCaP Cells Results in a Hormone Refractory Phenotype To further test the hypothesis that EBP1 is important in the reversal of the hormone refractory phenotype, LNCaP cells in which EBP1 expression had been ablated were created by transduction with a lentivirus targeting the EBP1 gene. EBP1 expression was knocked down in the C13, but not the A16 cell line (FIG. 7A). HRG inhibited the growth of A16 cells as expected (11). In contrast, HRG stimulated the growth of C13 LNCaP cells in which EBP1 expression had been ablated, similar to its effects on androgen independent cell lines (FIG. 7B, left panel). To examine the potential role of PI3K/AKT signaling pathway in this phenomenon, EBP1 knock down cells were treated with HRG and phosphorylated AKT was measured. AKT was basally phosphorylated in both LNCaP and EBP1 knock out cells. However, HRG induced a greater increase in pAKT protein levels in EBP1 depleted LNCaP cells as compared with controls (FIG. 7B, right panel).

The alteration of expression of two genes associated with hormone refractory growth in EBP1 knock out cells was further demonstrated. Levels of secreted PSA in conditioned media of log phase cells were 12.5 ng/$10^4$ cells for A16 cells and 75 ng/$10^4$ cells for the shEBP1 transduced C13 cells. Abrogation of the expression of the EBP1 gene led to an upregulation of AGR2 (FIG. 7C, left panel). We also tested the transcriptional response of an AR regulated MMTV promoter to R1881. The response was significantly ($p<0.05$) enhanced in EBP1 knock out cells (FIG. 7C, middle panel). Finally, we examined the response of A16 and C13 cells to docetaxel. The A16 control cells were sensitive to docetaxel with a 65% reduction in growth observed at 5 nM of the drug, In contrast, C13 cells were relatively resistant to docetaxel with a maximum of 15% growth inhibition at 20 nM (FIG. 7C, right panel).

Manipulation of Ebp1 Expression Affects Growth in Animal Models

To corroborate if the effects observed in vitro are observed in vivo, the consequence of expression of EBP1 on the tumorigenicity of C81 cells in female nude mice was examined. EBP1 and vector transfected cells were injected subcutaneously into female nude mice and tumor growth was monitored in two independent experiments (FIG. 8). The first measurable tumor derived from C81 vector transfectants was detected on day 8. In contrast, tumor development and growth of EBP1 transfectants were much slower with the first tumor being observed on day 20. On Day 28 post transplantation, tumors were observed at only 1/26 of the EBP1 inoculation sites, as opposed to 24/26 of the sites for vector controls. At the end of both studies, tumors had developed at 25/26 of the sites injected with the vector control cells, while 10/26 of the sites inoculated with EBP1 transfectants developed tumors (FIG. 8A) ($p=0.00001$ by Fisher's exact test, two sided). Average tumors volumes for the EBP1 transfectants observed at the end of the first study (3 animals per group, 6 sites per group) were $104\pm70$ mm$^3$ as compared with $998\pm206$ mm$^3$ (Mean+S.E.) for the vector controls ($p=0.01$). In the second experiment (10 animals per group, 20 sites per group), the average tumor volume was $206\pm54$ for the EBP1 transfectants and $561\pm47$ for the vector controls ($p=0.0001$) (FIG. 8B).

The ability of A16 and C13 cells (in which EBP1 expression had been decreased) to form tumors in female nude mice was also examined. At the concentrations used, we found that parental low passage LNCaP cells formed tumors in the same manner as the A16 cells with measurable growth being observed at all sites at Day 50 (data not shown). However, growth of LNCaP controls and A16 cells leveled off at day 58. In contrast, C13 cells continued to grow. At the termination of the experiment at Day 68 post inoculation, the average tumor volume was $307\pm64$ mm$^3$ for the A16 controls and $542\pm67$ mm$^3$ for the C13 EBP1 knock out cells ($p=0.04$) (FIG. 8C).

Wet weights of the tumors were also significantly different: A16=0.150±0.03 versus C13=0.288±0.05 grams (p.03).

Discussion

Emerging studies indicate the importance of ErbB receptor signaling in hormone refractory prostate cancer (39). EBP1, an ErbB3 binding protein, also functions as an AR corepressor, suggesting its role in suppression of ErbB mediated activation of AR. In these studies, it was demonstrated that restoration of EBP1 expression ameliorated the hormone refractory phenotype of C81 cells and that elimination of EBP1 expression resulted in a hormone refractory phenotype in hormone dependent LNCaP cells. These studies suggest the therapeutic potential of EBP1, an endogenous AR corepressor, for treatment of advanced prostate cancer.

Restoration of EBP1 gene expression in hormone refractory C81 cells led to a reversal of the androgen independent phenotype based on a series of established criteria. These biological changes were likely due in part to the decreased expression of proteins contributing to the androgen independent phenotype. AR protein levels were decreased in C81-EBP1 transfectants, consistent with our previous finding obtained from low passage hormone dependent LNCaP cells (9). Previous studies have found that EBP1 modulates AR activity by binding androgen responsive elements within AR target genes and recruiting HDAC complexes to repress transcription (40). This recruitment of transcriptional repressors may have lead to the decreased expression of AR target genes such as PSA, TMPRSS2, and KALLIKREN-2 that are potentially involved in androgen independent growth. The decreased expression of these AR target genes may have restored the physiological response of C81 cells to DHT as observed herein, and resulted in the growth inhibition induced by Casodex. The increased dependence of C81 EBP1 transfected cells on androgens was also evidenced by the fact that EBP1 transfected cells grew poorly in female mice. Similarly, inhibition of EBP1 expression in hormone dependent LNCaP cells enhanced their tumorigenicity in female mice.

Notably, expression of the androgen regulated genes AGR2 and TSPY, undetectable in low passage LNCaP cells in the absence of androgens (9), was decreased in C81-EBP1 transfectants. Further, inhibition of EBP1 protein expression in LNCaP cells led to upregulation of AGR2. AGR2, the human homologue of the *Xenopus* anterior gradient 2 gene, is increased in LNCaP cells in response to androgen treatment and overexpressed in primary prostate adenocarcinoma (20). Moreover, elevated AGR2 expression is significantly associated with poor survival of prostate cancer patients (41). As there is no effective therapy for metastatic prostate cancer, the possible role of EBP1 as a modulator of AGR2 gene expression warrants further investigation.

A combination of Mitoxantrone and Docetaxel is currently the standard palliative treatment in hormone-refractory prostate cancer patients (42). BCL-2, which is overexpressed in several models of androgen independent cancer in vitro (43; 44) and in human refractory prostate cancers (31), is a potent inhibitor of apoptosis induced by these drugs. Unexpectedly, the protein level of BCL-2 was decreased in EBP1 transfected C81 cells. The mechanism of the inhibition of BCL-2 expression in C81-EBP1 transfectants is not known. Our microarray data showed no changes in BCL-2 mRNA levels in EBP1 transfectants as compared with vector controls. EBP1 can directly bind BCL-2 mRNA, suggesting that EBP1 may have effects on translation efficiency (45).

Alternatively, EBP1 may alter the stability of the BCL-2 protein. Nevertheless, an increase in sensitivity to docetaxel and mitoxantrone was observed in EBP1 transfected cells in the absence of androgens. Given the importance of BCL-2 in sensitivity to these drugs in prostate cancer (46) (30), the decreased levels of BCL-2 in EBP1 transfectants may have contributed to this effect. It is of interest that changes in sensitivity were only observed in androgen deprived conditions. Studies of drug sensitivity of LNCaP C33 and C81 variants were similarly conducted in steroid free media (30), to mimic changes observed in androgen deprived conditions in vivo. It is possible that activation of alternative pathways, such as ErbB signaling, become more important for cell growth and survival in the androgen deprived environment and EBP1, by interfering with such pathways, inhibits growth.

A growing literature indicates that ErbB signaling in androgen-deprived conditions is vital to androgen refractory growth and that the Erb2/ErbB3 heterodimer is a critical target in hormone refractory prostate cancer (5). Results of this study showed that ectopic expression of EBP1 completely abrogated the ability of HRG to induce growth of C81 androgen independent cells or activate AKT in androgen deprived media. This is the first report that an endogenous AR corepressor can inhibit HRG induced AKT phosphorylation in hormone refractory cells. These data suggest that restoration of EBP1 not only diminishes HRG-activated signaling which exacerbates hormone refractory prostate cancer (13), but also undermines continued activation of PI(3)K/AKT signaling. Knock down of EBP1 expression resulted in aberrant HRG-induced growth stimulation, rather than growth inhibition, in hormone dependent LNCaP cells. In keeping with this finding, knock down of EBP1 protein may allow antagonistic molecules such as HRG to function as AR agonists and provide mechanistic insight into EBP1 status in a clinical setting.

In summary, the studies presented here show that overexpression of EBP1, an AR corepressor that interacts with ErbB3, modulated the hormone refractory phenotype both in vitro and in vivo. These studies support the role of EBP1 as an endogenous negative regulator of the AR signaling. These studies provide a rationale for the design of novel therapeutic approaches, based on EBP1 biology, for the treatment of hormone refractory prostate cancer.

REFERENCES FOR EXAMPLE 2

(1) Feldman B J, Feldman D. The development of androgen-independent prostate cancer. Nat Rev Cancer 2001 October; 1(1):34-45.

(2) Grossmaim M E, Huang H, Tindall D J. Androgen receptor signaling in androgen refractory prostate cancer. J Natl Cancer Inst 2001 Nov. 21; 93(22): 1687-97.

(3) Isaacs J T, Isaacs W B. Androgen receptor outwits prostate cancer drugs. Nat Med 2004 January; 10(1):26-7.

(4) El Sheikh S S, Domin J, Abel P, Stamp G, Lalani e. Androgen-independent prostate cancer: potential role of androgen and ErbB receptor signal transduction crosstalk. Neoplasia 2003 March; 5(2):99-109.

(5) Mellinghoff I K, Vivanco I, Kwon A, Tran C, Wongvipat J, Sawyers C L. HER2/neu kinase-dependent modulation of androgen receptor function through effects on DNA binding and stability. Cancer Cell 2004 November; 6(5):517-27.

(6) Radomski N, Jost E. Molecular cloning of a murine cDNA encoding a novel protein, p38-2G4, which varies with the cell cycle. Exp Cell Res 1995 October; 220(2):434-45.

(7) Heery D M, Hoare 5, Hussain 5, Parker M G, Sheppard H M. Core LXXLL motif sequences in CBP, SRC1 and RIP140 define affinity and selectivity for steroid and retinoid receptors. J Biol Chem 2000 Nov. 14.
(8) Zhang Y X, Fondell J D, Wang Q B, Xia X M, Cheng A W, Lu M L, et al. Repression of androgen receptor mediated transcription by the ErbB-3 binding protein, Ebp1. Oncogene 2002 Aug. 15; 21(36):5609-18.
(9) Zhang Y, Wang X W, Jelovac D, Nakanishi T, Yu M H, Akinmade D, et al. The ErbB3-binding protein Ebp1 suppresses androgen receptor-mediated gene transcription and tumorigenesis of prostate cancer cells. Proc Natl Acad Sci USA 2005 Jul. 12; 102(28):9890-5.
(10) Grasso A W, Wen D, Miller C M, Rhim J S, Pretlow T G, Kung H J. ErbB kinases and NDF signaling in human prostate cancer cells. Oncogene 1997 Nov. 27; 15(22): 2705-16.
(11) Tal-Or P, Di Segni A, Lupowitz Z, Pinkas-Kramarski R. Neuregulin promotes autophagic cell death of prostate cancer cells. Prostate 2003 May 1; 55(2):147-57.
(12) Abreu-Martin M T, Charm A, Palladino A A, Craft N A, Sawyers C L. Mitogen activated protein kinase kinase kinase 1 activates androgen receptor-dependent transcription and apoptosis in prostate cancer. Mol Cell Biol 1999 July; 19 (7):5143-54.
(13) Gregory C W, Whang Y E, McCall W, Fei X, Liu Y, Ponguta L A, et al. Heregulin induced activation of HER2 and HER3 increases androgen receptor transactivation and CWR-R1 human recurrent prostate cancer cell growth. Clin Cancer Res 2005 Mar. 1; 11(5):1704-12.
(14) Mendoza N, Phillips G L, Silva J, Schwall R, Wickramasinghe D. Inhibition of ligand-mediated HER2 activation in androgen-independent prostate cancer. Cancer Res 2002 Oct. 1; 62(19):5485-8.
(15) Nakanishi T, Karp J E, Tan M, Doyle L A, Peters T, Yang W, et al. Quantitative analysis of breast cancer resistance protein and cellular resistance to flavopiridol in acute leukemia patients. Clin Cancer Res 2003 Aug. 15; 9(9):3320-8.
(16) Krick R, Jakubiczka 5, Arnemann J. Expression, alternative splicing and haplotype analysis of transcribed testis specific protein (TSPY) genes. Gene 2003 Jan. 2; 302(1-2):11-9.
(17) Fritzsche F R, Dahl E, Pahl 5, Burkhardt M, Luo J, Mayordomo E, et al. Prognostic relevance of AGR2 expression in breast cancer. Clin Cancer Res 2006 Mar. 15; 12 (6):1728-34.
(18) Santegoets S J, Schreurs M W, Reurs A W, Lindenberg J J, Kueter E W, van den Eertwegh A J, et al. Identification and characterization of ErbB-3-binding protein1 as a target for immunotherapy. J Immunol 2007 Aug. 1; 179 (3):2005-12.
(19) Xia X, Lessor T J, Zhang Y, Woodford N, Hamburger A W. Analysis of the expression pattern of Ebp1, an ErbB-3-binding protein. Biochem Biophys Res Commun 2001 Nov. 23; 289(1):240-4.
(20) Zhang J S, Gong A, Cheville J C, Smith D I, Young C Y. AGR2, an androgen inducible secretory protein overexpressed in prostate cancer. Genes Chromosomes Cancer 2005 July; 43(3):249-59.
(21) Lessor T J, Yoo J Y, Xia X, Woodford N, Hamburger A W. Ectopic expression of the ErbB-3 binding protein ebp1 inhibits growth and induces differentiation of human breast cancer cell lines. J Cell Physiol 2000 June; 183(3):321-9.
(22) Yu Y P, Landsittel D, Jing L, Nelson J, Ren B, Liu L, et al. Gene expression alterations in prostate cancer predicting tumor aggression and preceding development of malignancy. J Clin Oncol 2004 Jul. 15; 22(14):2790-9.
(23) Vanaja D K, Cheville J C, Iturria S J, Young C Y. Transcriptional silencing of zinc finger protein 185 identified by expression profiling is associated with prostate cancer progression. Cancer Res 2003 Jul. 15; 63(14):3877-82.
(24) Singh D, Febbo P G, Ross K, Jackson D G, Manola J, Ladd C, et al. Gene expression correlates of clinical prostate cancer behavior. Cancer Cell 2002 March; 1 (2):203-9.
(25) LaTulippe E, Satagopan J, Smith A, Scher H, Scardino P, Reuter V, et al. Comprehensive gene expression analysis of prostate cancer reveals distinct transcriptional programs associated with metastatic disease. Cancer Res 2002 Aug. 1; 62(15):4499-506.
(26) Squatrito M, Mancino M, Donzelli M, Areces L B, Draetta G F. EBP1 is a nucleolar growth-regulating protein that is part of pre-ribosomal ribonucleoprotein complexes. Oncogene 2004 May 27; 23 (25):4454-65.
(27) Ahn J Y, Liu X, Liu Z, Pereira L, Cheng D, Peng J, et al. Nuclear Akt associates with PKC-phosphorylated Ebp 1, preventing DNA fragmentation by inhibition of caspase-activated DNase. EMBO J 2006 May 17; 25(10):2083-95.
(28) Igawa T, Lin F F, Lee M S, Karan D, Batra S K, Lin M F. Establishment and characterization of androgen-independent human prostate cancer LNCaP cell model. Prostate 2002 Mar. 1; 50(4):222-35.
(29) Tannock I F, de W R, Berry W R, Horti J, Pluzanska A, Chi K N, et al. Docetaxel plus prednisone or mitoxantrone plus prednisone for advanced prostate cancer. N Engl J Med 2004 Oct. 7; 351(15):1502-12.
(30) Zelivianski S, Spellman M, Kellerman M, Kakitelashvilli V, Zhou X W, Lugo E, et al. ERK inhibitor PD98059 enhances docetaxel-induced apoptosis of androgen dependent human prostate cancer cells. Int J Cancer 2003 Nov. 10; 107(3):478-85.
(31) Colombel M, Synimans F, Gil 5, O'Toole K M, Chopin D, Benson M, et al. Detection of the apoptosis-suppressing oncoprotein bc 1-2 in hormone-refractory human prostate cancers. Am J Pathol 1993 August; 143(2):390-400.
(32) Oesterling J E. PSA and early prostate cancer detection: the importance of age-specific reference ranges. Can J Oncol 1994 November; 4 Suppl 1:52-6.
(33) Partin A W, Catalona W J, Finlay J A, Darte C, Tindall D J, Young C Y, et al. Use of human glandular kallikrein 2 for the detection of prostate cancer: preliminary analysis. Urology 1999 November; 54(5):839-45.
(34) limes H E, Liu D, Barraclough R, Davies M P, O'Neill P A, Platt-Higgins A, et al. Significance of the metastasis-inducing protein AGR2 for outcome in hormonally treated breast cancer patients. Br J Cancer 2006 Apr. 10; 94(7): 1057-65.
(35) Pfeil K, Eder I E, Putz T, Ramoner R, Culig Z, Ueberall F, et al. Long-term androgen-ablation causes increased resistance to PI3KIAkt pathway inhibition in prostate cancer cells. Prostate 2004 Feb. 15; 58(3):259-68.
(36) Wen Y, Hu M C, Makino K, Spohn B, Bartholomeusz G, Yan D H, et al. HER 2/neu promotes androgen-independent survival and growth of prostate cancer cells through the Akt pathway. Cancer Res 2000 Dec. 15; 60(24): 6841-5.
(37) Miyamoto H, A!tuwaijri 5, Cai Y, Messing E M, Chang C. Inhibition of the Akt, cyclooxygenase-2, and matrix metalloproteinase-9 pathways in combination with androgen deprivation therapy: potential therapeutic approaches for prostate cancer. Mol Carcinog 2005 September; 44(1): 1-10.
(38) Hermans K G, van A, Veltman J A, van W W, van Kessel A G, Trapman J. Loss of a small region around the PTEN locus is a major chromosome 10 alteration in prostate cancer xenografts and cell lines. Genes Chromosomes Cancer 2004 March; 39(3): 17 1-84.
(39) Scher H I, Sawyers C L. Biology of progressive, castration-resistant prostate cancer: directed therapies targeting the androgen-receptor signaling axis. J Clin Oncol 2005 Nov. 10; 23(32):8253-61.
(40) Zhang Y, Akinmade D, Hamburger A W. The ErbB3 binding protein Ebp1 interacts with Sin3A to repress E2F 1 and AR-mediated transcription. Nucleic Acids Res 2005; 33(18):6024-33.
(41) Zhang Y, Forootan S S, Liu D, Barraclough R, Foster C S, Rudland P S, et al. Increased expression of anterior gradient-2 is significantly associated with poor survival of prostate cancer patients. Prostate Cancer Prostatic Dis 2007; 10 (3):293-300.
(42) Berry W, Dakhil 5, Gregurich M A, Asmar L. Phase II trial of single-agent weekly docetaxel in hormone-refractory, symptomatic, metastatic carcinoma of the prostate. Semin Oncol 2001 August; 128(4 Suppl 15):8-15.
(43) Shi X B, Ma A H, Tepper C G, Xia L, Gregg J P, Gandour-Edwards R, et al. Molecular alterations associated with LNCaP cell progression to androgen independence. Prostate 2004 Aug. 1; 60(3):257-71.
(44) Lu 5, Tsai S Y, Tsai M J. Molecular mechanisms of androgen-independent growth of human prostate cancer LNCaP-AI cells. Endocrinology 1999 November; 1140 (11):5054-9.
(45) Bose S K, Sengupta T K, Bandyopadhyay S, Spicer E K. Identification of Ebp1 as a component of cytoplasmic bcl-2 mRNP (messenger ribonucleoprotein particle) complexes. Biochem J 2006 May 15; 11396(1):99-107.
(46) Nehme A, Varadarajan P, Sellakumar G, Gerhold M, Niedner H, Zhang Q, et al. Modulation of docetaxel-induced apoptosis and cell cycle arrest by all-trans retinoic acid in prostate cancer cells. Br J Cancer 2001 Jun. 1; 1184(11):1571-6.

Example 3

Inhibition of Heregulin Mediated MCF-7 b Breast Cancer Cell Growth by the ErbB3 Binding Protein EBP1

Summary: The ErbB2/3 heterodimer plays a critical role in breast cancer genesis and progression. EBP1, an ErbB3 binding protein, inhibits breast cancer growth but its effects on ErbB3 ligand mediated signal transduction or ErbB receptors is not known. We report here that ectopic expression of EBP1 in MCF-7 and AU565 breast cancer cell lines inhibited HRG induced proliferation. ErbB2 protein levels were substantially decreased in EBP1 transfectants, while ErbB3 levels were unchanged. HRG-induced AKT activation was attenuated in EBP1 stable transfectants and transfection of a constitutively activated AKT partially restored the growth response to HRG. Down-regulation of EBP1 expression in MCF-7 cells by shRNA resulted in increased cell growth in response to HRG and increased cyclin D1 and ErbB2 expression. These results suggest that EBP1, by down-regulating ErbB signal transduction, attenuates HRG-mediated growth of breast cancer cells.

Introduction: A wealth of clinical data has demonstrated the aberrant expression of ErbB family members in breast cancer [1,2]. The ErbB2 gene is amplified in 20-30% of breast carcinomas contributing to more aggressive disease [3]. The overexpression of ErbB2 has been successfully exploited therapeutically by use of the monoclonal antibody Trastuzumab and by tyrosine kinase inhibitors. ErbB3 is also overexpressed in many breast tumors [4]. Coexpression of ErbB2 and ErbB3 is significantly associated with decreased survival [5]. The ErbB2/ErbB3 receptor pair forms the most potent mitogenic receptor complex in vitro [6] and is key to the proliferation of human breast cancer cells that express these receptors [7].

Our laboratory has been interested in the role of ErbB3 as a regulator of growth and differentiation of human breast cancer cells. The ErbB3 receptor has impaired tyrosine kinase activity [8,9], necessitating its interactions with other proteins to exert its biological effects. Several proteins interact with ErbB3 to transduce its biological effects. For example, ErbB2 heterodimerizes with ErbB3 after HRG stimulation, leading to phosphorylation and activation of downstream substrates [10]. The RING finger E3 ubiquitin ligase neuregulin receptor degradation protein-1 (Nrdp1) associates with ErbB3 in an activation independent manner and is believed to be involved in ErbB3 trafficking or localization [11,12]. Another ErbB3 binding protein (EBP1) was isolated in our laboratory during a yeast two-hybrid screen for ErbB3 interacting proteins [13]. Overexpression of EBP1 inhibits growth of both estrogen receptor (ER) positive and negative, ErbB2/3 expressing cell lines such as AU565, MCF-7, SKBR3 and MDA-MB-453. EBP1 does not inhibit the growth of the MDAMB-468 cell line which does not express ErbB2. In AU565 cells, ectopic expression of EBP1 promotes G2/M cell cycle arrest and cellular differentiation [14]. Overexpression of EBP1 inhibits the transcription of reporter genes controlled by cyclin D1 cyclin E and c-myc promoters and the transcription of endogenous E2F1 and c-myc genes via its binding to an E2F1 consensus element [15-17]. The interactions of EBP1 with histone deacetylase 2 (HDAC2), Rb and Sin3A are necessary for its ability to repress transcription [16-18]. HRG increases binding of EBP1 to the E2F1 promoter complex and enhances EBP1-mediated repression of E2F1 regulated gene transcription [17]. Recent data also suggest that EBP1 is an RNA binding protein [19-21], that can affect protein translation.

While our previous work demonstrated that ectopic expression of EBP1 inhibits growth of human breast cancer cell lines, the effect of EBP1 on HRG-induced signaling and proliferation was not examined. We hypothesized that EBP1 may specifically interfere with HRG-induced growth signals. In this study, we determined that ectopic expression of EBP1 inhibited the HRG-induced growth of MCF-7 and AU565 breast cancer cells. A decrease in AKT activation after HRG treatment was observed in EBP1 MCF-7 transfectants.

2. Materials and Methods 2.1. Cell culture. MCF-7 cells were obtained from the American Type Culture Collection (Manassas, Va.) and maintained at 37° C. in a humidified atmosphere of 5% $CO_2$ in air in RPMI 1640 (Biofluids, Rockville, Md.) and 10% FBS (Sigma, St. Louis, Mo.).

2.2. Reagents. Heregulin b1 (HRGb1) was obtained from R&D Systems Inc. (Minneapolis, Minn.), EGF from Sigma and Geneticin (G418) from Invitrogen (San Jose, Calif.).

2.3. Plasmids. A full-length EBP1 cDNA (GenBank NM006191) was generated by PCR with specific reverse and forward primers containing EcoRI and BamHII restriction sites using a pcDNA-EBP1 vector as a template [18]. This cDNA includes all three possible translation initiation sites of EBP1 and encodes the largest form of the protein. The cDNA was subcloned into the BamHI-EcoR1 sites of the CMV10 vector (Sigma) which contains a 3× Flag epitope tag. The orientation and integrity of the cDNA insert was confirmed by automated DNA sequencing in the core laboratory of the University of Maryland School of Medicine using sequencing primers for the CMV 10 plasmid (Sigma). A myristylated constitutively activated AKT plasmid cloned into a CMV6 expression vector has been previously described [22].

2.4. Creation of stably transfected cell lines. To establish EBP1 overexpressing stable transfectants, subconfluent MCF-7 cells in 100-mm tissue culture dishes were transfected with 10 µg of CMV10, or CMV10-EBP1 expression plasmids using Fugene-6 according to the manufacturer's protocol. Cells were selected in G418 (500 µg/ml) for 5 weeks and mass cultures obtained. The AU565-EPB1 cell line has been previously described [14].

For creation of EBP1 silenced MCF-7 cell lines, shRNA targeted against the coding region beginning at nucleotide 476 (Genbank Accession No. U87954) (AAGCGACCAG-GAUUAUAUUCU, SEQ ID NO: 26) was cloned into the pRNAT-U6.1 lentiviral vector (GenScript Corp., Scotch Plains, N.J.). A synthetic oligo encoding this sequence was previously demonstrated to decrease EBP1 expression in prostate cancer cell lines [23]. Lentiviral particles were prepared using the Invitrogen ViraPower™ system in 293FT cells as described by the manufacturer. MCF-7 cells were transduced with lentiviral stock and polybrene (6 µg/ml) and mass cultures were selected in G418 (500 µg/ml).

2.5. Western blot analysis. Total cell extracts were prepared by direct lysis of cells with lysis buffer [50 mM Tris-HCl (pH 7.4), 1 mM EDTA, 250 mM NaCl, 1% Triton X-100, 0.5 mM DTT, and 1× Complete™ protease inhibitor]. Protein concentrations were measured using a detergent compatible kit (Bio-Rad). Proteins (30 lg per well) were resolved by SDS-PAGE, transferred to PVDF membranes, and immunoblotted as described [13]. The ErbB3 (C-17) antibody was from Santa Cruz (Santa Cruz, Calif.), the ErbB2 antibody from Calbiochem (La Jolla, Calif.), the EBP1 antibody from Upstate (Lake Placid, N.Y.), the FLAG M2 and rabbit anti-actin antibodies from Sigma, the phospho-AKT (Ser 473), and total AKT, antibodies were from Cell Signaling (Beverly, Mass.) and the p-MAPK and MAPK antibodies were from Promega (Madison, Wis.). Images were quantified using IMAGE-J software (NIH). Where indicated, blots were stripped in Restore Western blot Stripping Buffer™ (Pierce) as directed by the manufacturer and reprobed.

2.6. Cell growth assays. For studies assessing the effect of HRG or EGF on cell growth, cells ($5 \times 10^3$) were plated in 96-well plates in complete media. After a 24-h attachment period, the medium was replaced with phenol-red free RPMI 1640 with 2% FBS and HRGb1 or EGF at the indicated concentrations. Relative cell numbers were determined 4 days later using a Promega Proliferation Reagent as per manufacturer's instructions with absorbance being read at 490 nm using a Dynex plate reader.

2.7. Statistical analysis. Data were analyzed using a two-tailed Students t-test and a p <0.05 was deemed statistically significant.

3. Results 3.1. EBP1 inhibits HRG-induced growth. As ErbB3 plays a key role in the proliferation of breast cancer cells, we sought to determine the effect of EBP1, which binds ErbB3, on cell proliferation induced by HRG, an ErbB3 ligand. An MCF-7 cell line stably transfected with FLAG-EBP1 was created (FIG. 9A, left panel). EBP1 expression was increased 2.1-fold (FIG. 9A, right panel), as determined by densitometric tracing, in keeping with previous data indicating that high expression of EBP1 is incompatible with cell growth [14,24]. MCF-7 vector control or EBP1 transfectants were plated in complete media and then switched to media containing 2% FBS in the presence or absence of increasing concentrations of HRG. HRG significantly (p<0.05) enhanced the growth of MCF-7 vector control cells with a maximal increase of 42% at 10 ng/ml as expected [25]. In contrast, the growth of cells transfected with EBP1 was unchanged by HRG at any of the concentrations tested (FIG. 9B). To test if the inhibition of HRG signaling occurred in other breast cancer cell lines, we tested the ability of AU565 cells stably transfected with EBP1 [14] to respond to HRG. EBP1 expression is increased two-fold in this cell line [14]. AU565 vector control or EBP1 transfectants were plated in complete media and then switched to media containing 2% FBS in the presence or absence of increasing concentrations of HRG. HRG enhanced the growth of AU565 vector control cells with a maximal increase at 10 ng/ml. Growth at higher concentrations was inhibited by HRG as previously reported [26]. In contrast, the growth of cells transfected with EBP1 was not significantly (p<0.05) changed by HRG at any of the concentrations tested (FIG. 9C).

To determine if the inhibition of cell growth was specific for the HRG signaling pathway, we tested the ability of EBP1 to inhibit the growth response to EGF. MCF-7 vector control and EBP1 transfected cells were stimulated with EGF at increasing concentrations. MCF-7 control cells were able to respond to EGF as previously reported [27]. In contrast to the response to HRG, MCF-7 EBP1 transfected cells were growth stimulated by EGF to the same extent as control cells (FIG. 9D).

To examine the mechanism underlying the EBP1 inhibition of HRG-induced growth, we evaluated the effect of EBP1 expression on the protein levels of ErbB2 and ErbB3. There was no change in the level of ErbB3 (FIG. 10A) in the MCF-7-EBP1 transfectants when compared to vector controls. In contrast, ErbB2 protein was significantly decreased (FIG. 10B). Similar results were observed in another group of independently derived MCF-EBP1 transfected cells (data not shown). ErbB2 protein was also decreased by 57% in AU565 cells (FIG. 10C).

We next evaluated the effect of EBP1 overexpression on the activation of downstream signaling in response to HRG. HRG-induced activation of the ErbB2/ErbB3 heterodimer results in stimulation of the MEK/MAPK pathway [7]. HRG treatment caused a robust activation of MAPK in vector controls as determined using a phospho-specific MAPK antibody. In contrast, as previously reported for AU565 cells [14], MAPK was constitutively phosphorylated in EBP1 overexpressing cells. A small increase in MAPK phosphorylation was observed after HRG treatment in EBP1 transfectants (FIG. 11A). HRG induced AKT phosphorylation in vector control MCF-7 cells at both 10 and 20 min after treatment as determined using a phospho-specific AKT antibody. However, this response was attenuated in the EBP1 transfectants as compared to the vector controls (FIG. 11B).

We next examined the role of the attenuation of AKT phosphorylation in the failure of MCF-7 EBP1 transfectants to grow in response to HRG. Transient transfection of a constitutively activated AKT resulted in a partial rescue of the HRG stimulated growth of EBP1 overexpressing cells (p<0.05) (FIG. 11C).

3.2. shRNA against EBP1 augments HRG-induced cell proliferation.

The contribution of EBP1 to HRG-induced cell growth was evaluated by knockdown of endogenous EBP1 expression. As shown in FIG. 12A, transduction of MCF 7 cells with an shRNA vector targeted to EBP1 reduced EBP1 expression compared to a lentiviral control. The EBP1 knockdown cells grew about 30% faster than the vector controls in complete media (data not shown). To test the effects of ectopic expression of EBP1 on HRG-induced cell growth, cells were plated in complete media and then switched to media containing 2% FBS and 10 ng/ml of HRG. Growth was assessed 4 days later. HRG increased the growth of vector controls 40% similar to parental MCF-7 cells [25]. In contrast, HRG increased the growth of EBP1 knockdown cells 250% (FIG. 12B).

We further examined downstream effectors of HRG signaling. AKT was constitutively activated in the EBP1 knockdown cells and HRG did not further enhance the phosphorylation (FIG. 13A). As cyclin D1 is stimulated in HRG treated cells [28], we examined the protein levels of cyclin D1 in logarithmically growing control and EBP1 knockdown cells. Cyclin D1 levels were increased in cells in which EBP1 expression had been decreased as compared to lentivirus controls. As we had found that ErbB2 was decreased in EBP1 transfectants, we examined the levels of ErbB2 in EBP1 knockdown cells. EBP1 knockdown led to a 2.2-fold upregulation of ErbB2 expression when compared to actin controls (FIG. 13C).

4. Discussion

Increasing data support the clinical importance of specific ErbB heterodimers and their interacting partners in breast cancer development [2]. We have previously shown that the ErbB3 binding protein EBP1 inhibited the growth of ErbB2/ErbB3 expressing breast cancer cell lines [14]. However, the specific effect of EBP1 on HRG-induced proliferation and down stream signaling was not assessed. We hypothesized that EBP1 negatively regulates HRG signaling, resulting in growth inhibition of breast cancer cells. Studies presented here show that ectopic expression of EBP1 diminished HRG-induced cell proliferation in ErbB2/3 expressing AU565 and MCF-7 cells, while inhibition of EBP1 protein expression resulted in increased proliferation of MCF-7 cells in response to HRG. These data, along with our previously published work [14], demonstrate that EBP1 inhibits proliferation of cells that express both ErbB2 and ErbB3, regardless of ER status. Decreased cell growth was associated with a decrease in ErbB2 protein levels and attenuation of HRG-induced signaling. Our data suggest that EBP1 may function as a negative regulator of ErbB2/3 heterodimer signaling.

Ectopic expression of EBP1 specifically decreased HRG-induced stimulation of cell growth, as the ability of EGF to stimulate cell growth was not affected by EBP1 overexpression. To further examine the cause of this growth inhibition, we determined the levels of ErbB2 and ErbB3. The level of ErbB3 protein in EBP1 transfectants was unchanged from that of the vector control. This finding is in contrast to work of Jhabvala-Romera et al. [29] and Yen et al. [30] who showed that the ErbB modifying protein Ndrp1 induce decreases in the proteins levels of ErbB3. Surprisingly, levels of ErbB2 were greatly decreased in EBP1 overexpressing cells. The mechanism behind the decrease is unknown. It is possible that the binding of EBP1 to ErbB3 may inhibit ErbB2/3 heterodimers and destabilize ErbB2. In addition, EBP1 is an RNA binding protein [19,21] that may either destabilize ErbB2 mRNA or decrease its translation. ErbB4 was undetectable in control cells in our hands, and EGFR levels were unaffected (data not shown).

We examined the role that MAPK and AKT signaling might play in the inability of EBP1 transfectants to respond to HRG. As previously demonstrated in AU565 cells [14], ectopic expression of EBP1 resulted in constitutive MAPK phosphorylation. Sustained activation of MAPK is a marker of HRG-induced differentiation and inhibition of cell growth and this sustained MAPK activation may have contributed to the failure of EBP1 transfectants to grow in response to HRG. Pharmacological inhibition of MEK resulted in the inability of both EBP1 transfected and control cells to respond to HRG (data not shown). Thus, we were unable to directly test if the constitutive activation of MAPK was responsible for the inability of EBP1 transfectants to grow in response to HRG. As activation of AKT is a mediator of the growth stimulating effects of HRG in breast cancer cells [7,31], we also examined the ability of HRG to stimulate AKT phosphorylation. We found that the phosphorylation of AKT in response to HRG was decreased in EBP1 transfectants as compared to control cells. Thus, the reduced growth response to HRG in MCF-7 EBP1 transfectants may have been due in part to this attenuation of AKT signaling. Indeed, transfection of a constitutively activated AKT partially reversed the inhibitory effects of EBP1 on HRG-induced cell growth. The enhanced response to HRG in EBP1 knockout cells, in which AKT was constitutively activated, support the hypothesis that inhibition of AKT activation by endogenous EBP1 may contribute to the normal attenuation of ErbB signal transduction.

A second mechanism by which EBP1 may inhibit HRG-induced growth may be related to the ability of EBP1 to inhibit transcription of cyclin D1 and cyclin E genes [15,16]. Cyclin D1 and E are key regulators of breast cancer cell proliferation [32,33]. HRG-induced cell proliferation is mediated in part by increases in cyclin D1 levels [28]. EBP1 represses the activity of a cyclin D1 promoter luciferase reporter construct [15,16]. We have also demonstrated by ChIP analysis that EBP1 is recruited to the E2F1 promoter in response to HRG, where it can bind the transcriptional corepressors HDAC2 and Sin3A [18]. In addition, the ability of EBP1 to repress transcription is enhanced by HRG [17]. Thus, overexpression of EBP1 may result in recruitment of EBP1 to the cyclin D1 promoter, inhibiting transcription and ultimately cell growth. It is possible that endogenous EBP1, whose transcriptional repression activity is regulated by HRG, may serve as a negative feed back mechanism to prevent unrestrained HRG signaling.

In summary, we demonstrate here that the ectopic expression of EBP1 I in MCF-7 and AU565 cells resulted in the blocking of HRG mediated proliferation. In MCF-7 cells, this was accompanied by a decrease in AKT activation. Conversely, inhibiting EBP1 expression resulted in enhanced proliferation in response to HRG. These studies suggest that EBP1 may be a regulator of HRG signaling in ErbB2/3 expressing breast cancer cells and serve as a potential target for the development of anticancer agents.

REFERENCES FOR EXAMPLE 3

[1] T. Holbro, G. Civenni, N. E. Hynes, The ErbB receptors and their role in cancer progression, Exp. Cell Res. 284 (2003) 99-110.

[2] N. E. Hynes, H. A. Lane, ERBB receptors and cancer: the complexity of targeted inhibitors, Nat. Rev. Cancer 5 (2005) 341-354.

[3] D. J. Slamon, W. Godolphin, L. A. Jones, J. A. Holt, S. G. Wong, D. E. Keith, W. J. Levin, S. G. Stuart, J. Udove, A. Ullrich, Studies of the HER-2/neu proto-oncogene in human breast and ovarian cancer, Science 244 (1989) 707-712.

[4] N. R. Lemoine, D. M. Barnes, D. P. Hollywood, C. M. Hughes, P. Smith, E. Dublin, S. A. Prigent, W. J. Gullick, H. C. Hurst, Expression of the ERBB3 gene product in breast cancer, Br. J. Cancer 66 (1992) 1116-1121.

[5] S. M. Wiseman, N. Makretsov, T. O. Nielsen, B. Gilks, E. Yorida, M. Cheang, D. Turbin, K. Gelmon, D. G. Huntsman, Coexpression of the type 1 growth factor receptor family members HER-1, HER-2, and HER-3 has a synergistic negative prognostic effect on breast carcinoma survival, Cancer 103 (2005) 1770-1777.

[6] R. Pinkas-Kramarski, L. Soussan, H. Waterman, G. Levkowitz, I. Alroy, L. Klapper, S. Lavi, R. Seger, B. J. Ratzkin, M. Sela, Y. Yarden, Diversification of Neu differentiation factor and epidermal growth factor signaling by combinatorial receptor interactions, EMBO J. 15 (1996) 2452-2467.

[7] T. Holbro, R. R. Beerli, F. Maurer, M. Koziczak, C. F. Barbas III, N. E. Hynes, The ErbB2/ErbB3 heterodimer functions as an oncogenic unit: ErbB2 requires ErbB3 to drive breast tumor cell proliferation, Proc. Natl. Acad. Sci. USA 100 (2003) 8933-8938.

[8] M. H. Kraus, W. Issing, T. Miki, N. C. Popescu, S. A. Aaronson, Isolation and characterization of ERBB3, a third member of the ERBB/epidermal growth factor receptor family: evidence for overexpression in a subset of human mammary tumors, Proc. Natl. Acad. Sci. USA 86 (1989) 9193-9197.

[9] G. D. Plowman, G. S. Whitney, M. G. Neubauer, J. M. Green, V. L. McDonald, G. J. Todaro, M. Shoyab, Molecular cloning and expression of an additional epidermal growth factor receptor-related gene, Proc. Natl. Acad. Sci. USA 87 (1990) 4905-4909.

[10] R. Pinkas-Kramarski, M. Shelly, S. Glathe, B. J. Ratzkin, Y. Yarden, Neu differentiation factor/neuregulin isoforms activate distinct receptor combinations, J. Biol. Chem. 271 (1996) 19029-19032.

[11] A. J. Diamonti, P. M. Guy, C. Ivanof, K. Wong, C. Sweeney, K. L. Carraway III, An RBCC protein implicated in maintenance of steady-state neuregulin receptor levels, Proc. Natl. Acad. Sci. USA 99 (2002) 2866-2871.

[12] X. B. Qiu, A. L. Goldberg, Nrdp1/FLRF is a ubiquitin ligase promoting ubiquitination and degradation of the epidermal growth factor receptor family member, ErbB3, Proc. Natl. Acad. Sci. USA 99 (2002) 14843-14848.

[13] J. Y. Yoo, X. W. Wang, A. K. Rishi, T. Lessor, X. M. Xia, T. A. Gustafson, A. W. Hamburger, Interaction of the PA2G4 (EBP1) protein with ErbB-3 and regulation of this binding by heregulin, Br. J. Cancer 82 (2000) 683-690.

[14] T. J. Lessor, J. Y. Yoo, X. Xia, N. Woodford, A. W. Hamburger, Ectopic expression of the ErbB-3 binding protein EBP1 inhibits growth and induces differentiation of human breast cancer cell lines, J. Cell. Physiol. 183 (2000) 321-329.

[15] X. Xia, A. Cheng, T. Lessor, Y. Zhang, A. W. Hamburger, EBP1, an ErbB-3 binding protein, interacts with Rb and affects Rb transcriptional regulation, J. Cell. Physiol. 187 (2001) 209-217.

[16] Y. X. Zhang, N. Woodford, X. M. Xia, A. W. Hamburger, Repression of E2F11-mediated transcription by the ErbB3 binding protein EBP1 involves histone deacetylases, Nucleic Acids Res. 31 (2003) 2168-2177.

[17] Y. Zhang, A. W. Hamburger, Heregulin regulates the ability of the ErbB3-binding protein EBP1 to bind E2F promoter elements and repress E2F-mediated transcription, J. Biol. Chem. 279 (2004) 26126-26133.

[18] Y. Zhang, D. Akinmade, A. W. Hamburger, The ErbB3 binding protein EBP1 interacts with Sin3A to repress E2F1 and AR-mediated transcription, Nucleic Acids Res. 33 (2005) 6024-6033.

[19] S. K. Bose, T. K. Sengupta, S. Bandyopadhyay, E. K. Spicer, Identification of EBP1 as a component of cytoplasmic bcl-2 mRNP (messenger ribonucleoprotein particle) complexes, Biochem. J. 396 (2006) 99-107.

[20] M. Squatrito, M. Mancino, M. Donzelli, L. B. Areces, G. F. Draetta, EBP1 is a nucleolar growth-regulating protein that is part of pre-ribosomal ribonucleoprotein complexes, Oncogene 23 (2004) 4454-4465.

[21] M. Squatrito, M. Mancino, L. Sala, G. F. Draetta, EBP1 is a dsRNA-binding protein associated with ribosomes that modulates eIF2alpha phosphorylation, Biochem. Biophys. Res. Commun. 344 (2006) 859-868.

[22] R. Chen, O. Kim, J. Yang, K. Sato, K. M. Eisenmann, J. McCarthy, H. Chen, Y. Qiu, Regulation of Akt/PKB activation by tyrosine phosphorylation, J. Biol. Chem. 276 (2001) 31858-31862.

[23] Y. Zhang, A. W. Hamburger, Specificity and heregulin regulation of EBP1 (ErbB3 binding protein 1) mediated repression of androgen receptor signalling, Br. J. Cancer 92 (2005) 140-146.

[24] Y. X. Zhang, J. D. Fondell, Q. B. Wang, X. M. Xia, A. W. Cheng, M. L. Lu, A. W. Hamburger, Repression of androgen receptor mediated transcription by the ErbB-3 binding protein, EBP1, Oncogene 21 (2002) 5609-5618.

[25] Z. Aguilar, R. W. Akita, R. S. Finn, B. L. Ramos, M. D. Pegram, F. F. Kabbinavar, R. J. Pietras, P. Pisacane, M. X. Sliwkowski, D. J. Slamon, Biologic effects of heregulin/neu differentiation factor on normal and malignant human breast and ovarian epithelial cells, Oncogene 18 (1999) 6050-6062.

[26] S. S. Bacus, A. V. Gudkov, C. R. Zelnick, D. Chin, R. Stem, I. Stancovski, E. Peles, N. Ben-Baruch, H. Farbstein, R. Lupu, Neu differentiation factor (heregulin) induces expression of intercellular adhesion molecule 1: implications for mammary tumors, Cancer Res. 53 (1993) 5251-5261.

[27] B. B. van der, G. R. Rutteman, M. A. Blankenstein, S. W. de Laat, E. J. van Zoelen, Mitogenic stimulation of human breast cancer cells in a growth factor-defined medium: synergistic action of insulin and estrogen, J. Cell. Physiol. 134 (1988) 101-108.

[28] R. M. Neve, T. Holbro, N. E. Hynes, Distinct roles for phosphoinositide 3-kinase, mitogen-activated protein kinase and p38 MAPK in mediating cell cycle progression of breast cancer cells, Oncogene 21 (2002) 4567-4576.

[29] F. Jhabvala-Romero, A. Evans, S. Guo, M. Denton, G. M. Clinton, Herstatin inhibits heregulin-mediated breast cancer cell growth and overcomes tamoxifen resistance in breast cancer cells that overexpress HER-2, Oncogene 22 (2003) 8178-8186.

[30] L. Yen, Z. Cao, X. Wu, E. R. Ingalla, C. Baron, L. J. Young, J. P. Gregg, R. D. Cardiff, A. D. Borowsky, C. Sweeney, K. L. Carraway III, Loss of Nrdp1 enhances ErbB2/ErbB3-dependent breast tumor cell growth, Cancer Res. 66 (2006) 11279-11286.

[31] E. Peles, R. Lamprecht, R. Ben-Levy, E. Tzahar, Y. Yarden, Regulated coupling of the Neu receptor to phosphatidylinositol 30-kinase and its release by oncogenic activation, J. Biol. Chem. 267 (1992) 12266-12274.

[32] R. Hui, G. L. Finney, J. S. Carroll, C. S. Lee, E. A. Musgrove, R. L. Sutherland, Constitutive overexpression of cyclin D1 but not cyclin E confers acute resistance to antiestrogens in T-47D breast cancer cells, Cancer Res. 62 (2002) 6916-6923.

[33] G. G. McIntosh, J. J. Anderson, 1. Milton, M. Steward, A. H. Parr, M. D. Thomas, J. A. Henry, B. Angus, T. W. Lennard, C. H. Home, Determination of the prognostic value of cyclin D1 overexpression in breast cancer, Oncogene 11 (1995) 885-891.

Preferred embodiments of this invention are described herein, including the best mode known to the inventors for carrying out the invention. It should be understood that the illustrated embodiments are exemplary only, and should not be taken as limiting the scope of the invention.

All references, including publications, patent applications, and patents, cited herein are hereby incorporated by reference to the same extent as if each reference were individually and specifically indicated to be incorporated by reference and were set forth in its entirety herein.

We claim:

1. A method of treating hormone-independent prostate cancer in a subject in need thereof, comprising the steps of:
   administering to said subject a therapeutically effective amount of EPB1; and
   administering to said subject a therapeutically effective amount of at least one antiproliferation therapy.

2. The method of claim 1, wherein said at least one antiproliferation therapy is selected from the group consisting of administration of an antiandrogen, administration of an anticancer agent, radiation therapy, and surgery.

3. The method of claim 1, wherein the EPB1 is expressed from a viral vector.

4. The method of claim 3, wherein the viral vector, is a lentiviral vector.

5. The method of claim 1, wherein the EPB1 is expressed from polymer-packaged DNA.

6. The method of claim 1, wherein said step of administering to said subject a therapeutically effective amount of EPB1 comprises administering a composition comprising EPB1 and a protein transduction domain.

7. The method of claim 6, wherein said EPB1 is part of a fusion protein.

8. A method of inhibiting cell proliferation of a hormone-independent cancer cell, comprising:
   providing, to said hormone-independent cancer cell,
     a therapeutically effective amount of EPB1; and
     a therapeutically effective amount of at lest one antiproliferation therapy.

9. The method of claim 8, wherein said hormone-independent cancer cell is a hormone-refractory prostate cancer cell.

10. The method of claim 8, wherein the EPB1 is expressed from a viral vector.

11. The method of claim 10, wherein the viral vector is a lentiviral vector.

12. The method of claim 8, wherein the EPB1 is expressed from polymer-packaged DNA.

13. The method of claim 8, wherein said step of providing a therapeutically effective amount of EPB1 comprises providing a composition comprising EPB1 and a protein transduction domain.

14. The method of claim 13, wherein said EPB1 is part of a fusion protein.

15. A method of inhibiting unregulated proliferation of a cell that can otherwise be regulated by hormone administration, comprising:
   providing said cell with a therapeutically effective amount of EPB1 to convert said cell to a hormone-regulated phenotype; and
   providing said cell with at least one antiproliferation therapy to reduce unregulated cell proliferation.

16. The method of claim 15, wherein said at least one antiproliferation therapy is selected from the group consisting of administration of an antiandrogen, administration of an anticancer agent, radiation therapy, and surgery.

17. The method of claim 15, wherein the EPB1 is expressed from a viral vector.

18. The method of claim 17, wherein the viral vector is a lentiviral vector.

19. The method of claim 15, wherein the EPB1 is expressed from polymer-packaged DNA.

20. The method of claim 15, wherein said step of providing said cell with a therapeutically effective amount of EPB1 to convert said cell to a hormone-regulated phenotype comprises providing a composition comprising EPB1 and a protein transduction domain.

21. The method of claim 20, wherein said EPB1 is part of a fusion protein.

22. A method of treating a cancer cell with an antiproliferation therapy, wherein said cancer cell is first sensitized to treatment with said antiproliferation therapy, comprising
providing to said cancer cell. EPB1, wherein said EPB1 is provided in a therapeutically effective amount so as to sensitize said cancer cell to said treatment with said antiproliferation therapy; and
treating said sensitized cancer cell with said antiproliferation therapy.

23. The method of claim 22, wherein said antiproliferation therapy is selected from the group consisting of administration of an antiandrogen, administration of an anticancer agent, radiation therapy, and surgery.

24. The method of claim 22, wherein said EPB1 is expressed from a viral vector.

25. The method of claim 24, wherein the viral vector is a lentiviral vector.

26. The method of claim 22, wherein said EPB1 is expressed from polymer-packaged DNA.

27. The method of claim 22, wherein said step of providing comprises providing a composition comprising. EPB1 and a protein transduction domain.

28. The method of claim 27, wherein said EPB1 is part of a fusion protein.

29. A method of reversing a phenotype of a prostate cancer cell from hormone refractory to hormone susceptible, comprising providing EPB1 to said prostate cancer cell, wherein said EPB1 is provided in a therapeutically effective amount so as to reverse said phenotype of said prostate cancer cell from hormone refractory to hormone susceptible.

30. The method of claim 29, wherein said EPB1 is expressed from a viral vector.

31. The method of claim 30, wherein the viral vector is a lentiviral vector.

32. The method of claim 29, wherein said EPB1 is expressed from polymer-packaged DNA.

33. The method of claim 29, wherein said step of providing comprises providing a composition comprising EPB1 and a protein transduction domain.

34. The method of claim 33, wherein said EPB1 is part of a fusion protein.

35. A method of inhibiting proliferation of a cancer cell, comprising:
providing a therapeutically effective amount of EPB1 to said cancer cell; and
providing a therapeutically effective amount of at least one antiproliferation therapy to said cancer cell.

36. The method of claim 35, wherein said cell is a prostate cancer cell.

37. A composition comprising EPB1 or an EPB1 expressing entity in combination with an antiandrogen and/or an anticancer agent.

38. The composition of claim 37, wherein said EPB1 expressing entity is an EPB1 expressing viral vector.

39. The composition of claim 38, wherein the viral vector is a lentiviral vector.

40. The composition of claim 37, wherein EPB1 expressing entity is polymer-packaged EPB1 expressing DNA.

41. The composition of claim 37, wherein said EPB1 is a protein.

42. The composition of claim 41, wherein said EPB1 is part of a fusion protein.

* * * * *

SEQUENCE LISTING

<160> NUMBER OF SEQ ID NOS: 26

<210> SEQ ID NO 1
<211> LENGTH: 1185
<212> TYPE: DNA
<213> ORGANISM: Homo sapiens

<400> SEQUENCE: 1

```
atgtcgggcg aggacgagca acaggagcaa actatcgctg aggacctggt cgtgaccaag      60
tataagatgg ggggcgacat cgccaacagg gtacttcggt ccttggtgga agcatctagc     120
tcaggtgtgt cggtactgag cctgtgtgag aaaggtgatg ccatgattat ggaagaaaca     180
gggaaaatct tcaagaaaga aaaggaaatg aagaaaggta ttgctttttcc caccagcatt     240 tcggtaaata actgtgtatg tcacttctcc cctttgaaga gcgaccagga ttatattctc     300
aaggaaggtg acttggtaaa aattgacctt ggggtccatg tggatggctt catcgctaat     360
gtagctcaca cttttgtggt tgatgtagct caggggaccc aagtaacagg gaggaaagca     420
gatgttatta aggcagctca cctttgtgct gaagctgccc tacgcctggt caaacctgga     480
aatcagaaca cacaagtgac agaagcctgg aacaaagttg cccactcatt taactgcacg     540
ccaatagaag gtatgctgtc acaccagttg aagcagcatg tcatcgatgg agaaaaaacc     600
attatccaga atcccacaga ccagcagaag aaggaccatg aaaaagctga atttgaggta     660
catgaagtat atgctgtgga tgttctcgtc agctcaggag agggcaaggc caaggatgca     720
ggacagagaa ccactattta caaacgagac ccctctaaac agtatggact gaaaatgaaa     780
acttcacgtg ccttcttcag tgaggtggaa aggcgttttg atgccatgcc gtttactta     840 agagcatttg aagatgagaa gaaggctcgg atgggtgtgg tggagtgcgc caaacatgaa     900
ctgctgcaac catttaatgt tctctatgag aaggagggtg aatttgttgc ccagtttaaa     960
tttacagttc tgctcatgcc caatggcccc atgcggataa ccagtggtcc cttcgagcct    1020
gacctctaca agtctgagat ggaggtccag gatgcagagc taaaggccct cctccagagt    1080
tctgcaagtc gaaaaaccca gaaaagaaa aaaagaagg cctccaagac tgcagagaat    1140
gccaccagtg gggaaacatt agaagaaaat gaagctgggg actga                   1185
```

<210> SEQ ID NO 2
<211> LENGTH: 394
<212> TYPE: PRT
<213> ORGANISM: Homo sapiens

<400> SEQUENCE: 2

```
Met Ser Gly Glu Asp Glu Gln Gln Glu Gln Thr Ile Ala Glu Asp Leu
1               5                   10                  15

Val Val Thr Lys Tyr Lys Met Gly Gly Asp Ile Ala Asn Arg Val Leu
            20                  25                  30
```

-continued

```
Arg Ser Leu Val Glu Ala Ser Ser Gly Val Ser Val Leu Ser Leu
         35                  40                  45

Cys Glu Lys Gly Asp Ala Met Ile Met Glu Thr Gly Lys Ile Phe
 50                  55                  60

Lys Lys Glu Lys Glu Met Lys Lys Gly Ile Ala Phe Pro Thr Ser Ile
 65                  70                  75                  80

Ser Val Asn Asn Cys Val Cys His Phe Ser Pro Leu Lys Ser Asp Gln
                 85                  90                  95

Asp Tyr Ile Leu Lys Glu Gly Asp Leu Val Lys Ile Asp Leu Gly Val
                100                 105                 110

His Val Asp Gly Phe Ile Ala Asn Val Ala His Thr Phe Val Val Asp
                115                 120                 125

Val Ala Gln Gly Thr Gln Val Thr Gly Arg Lys Ala Asp Val Ile Lys
            130                 135                 140

Ala Ala His Leu Cys Ala Glu Ala Ala Leu Arg Leu Val Lys Pro Gly
145                 150                 155                 160

Asn Gln Asn Thr Gln Val Thr Glu Ala Trp Asn Lys Val Ala His Ser
                165                 170                 175

Phe Asn Cys Thr Pro Ile Glu Gly Met Leu Ser His Gln Leu Lys Gln
                180                 185                 190

His Val Ile Asp Gly Glu Lys Thr Ile Ile Gln Asn Pro Thr Asp Gln
            195                 200                 205

Gln Lys Lys Asp His Glu Lys Ala Glu Phe Glu Val His Glu Val Tyr
210                 215                 220

Ala Val Asp Val Leu Val Ser Ser Gly Glu Gly Lys Ala Lys Asp Ala
225                 230                 235                 240

Gly Gln Arg Thr Thr Ile Tyr Lys Arg Asp Pro Ser Lys Gln Tyr Gly
                245                 250                 255

Leu Lys Met Lys Thr Ser Arg Ala Phe Phe Ser Glu Val Glu Arg Arg
            260                 265                 270

Phe Asp Ala Met Pro Phe Thr Leu Arg Ala Phe Glu Asp Glu Lys Lys
                275                 280                 285

Ala Arg Met Gly Val Val Glu Cys Ala Lys His Glu Leu Leu Gln Pro
            290                 295                 300

Phe Asn Val Leu Tyr Glu Lys Glu Gly Glu Phe Val Ala Gln Phe Lys
305                 310                 315                 320

Phe Thr Val Leu Leu Met Pro Asn Gly Pro Met Arg Ile Thr Ser Gly
                325                 330                 335

Pro Phe Glu Pro Asp Leu Tyr Lys Ser Glu Met Glu Val Gln Asp Ala
            340                 345                 350

Glu Leu Lys Ala Leu Leu Gln Ser Ser Ala Ser Arg Lys Thr Gln Lys
                355                 360                 365

Lys Lys Lys Lys Ala Ser Lys Thr Ala Glu Asn Ala Thr Ser Gly
            370                 375                 380

Glu Thr Leu Glu Glu Asn Glu Ala Gly Asp
385                 390
```

<210> SEQ ID NO 3
<211> LENGTH: 39
<212> TYPE: DNA
<213> ORGANISM: Artificial
<220> FEATURE:
<223> OTHER INFORMATION: Synthetic primer

<400> SEQUENCE: 3

```
ggccagtgaa ttgtaatacg actcactata gggaggcgg                              39

<210> SEQ ID NO 4
<211> LENGTH: 16
<212> TYPE: DNA
<213> ORGANISM: Artificial
<220> FEATURE:
<223> OTHER INFORMATION: Synthetic primer

<400> SEQUENCE: 4
gcacgccaat agaagg                                                       16

<210> SEQ ID NO 5
<211> LENGTH: 17
<212> TYPE: DNA
<213> ORGANISM: Artificial
<220> FEATURE:
<223> OTHER INFORMATION: Synthetic primer

<400> SEQUENCE: 5
gtaaacggca tggcatc                                                      17

<210> SEQ ID NO 6
<211> LENGTH: 21
<212> TYPE: DNA
<213> ORGANISM: Artificial
<220> FEATURE:
<223> OTHER INFORMATION: Synthetic primer

<400> SEQUENCE: 6
aaggctatga atgtcagccc a                                                 21

<210> SEQ ID NO 7
<211> LENGTH: 22
<212> TYPE: DNA
<213> ORGANISM: Artificial
<220> FEATURE:
<223> OTHER INFORMATION: Synthetic primer

<400> SEQUENCE: 7
cattgaggct agagagcaag gc                                                22

<210> SEQ ID NO 8
<211> LENGTH: 17
<212> TYPE: DNA
<213> ORGANISM: Artificial
<220> FEATURE:
<223> OTHER INFORMATION: Synthetic primer

<400> SEQUENCE: 8
catccagtct cggattg                                                      17

<210> SEQ ID NO 9
<211> LENGTH: 19
<212> TYPE: DNA
<213> ORGANISM: Artificial
<220> FEATURE:
<223> OTHER INFORMATION: Synthetic primer

<400> SEQUENCE: 9
ctcatattgt agagcgggt                                                    19

<210> SEQ ID NO 10
<211> LENGTH: 18
<212> TYPE: DNA
```

```
<213> ORGANISM: Artificial
<220> FEATURE:
<223> OTHER INFORMATION: Synthetic primer

<400> SEQUENCE: 10
agtgctgtgt tcgccttg                                                 18

<210> SEQ ID NO 11
<211> LENGTH: 18
<212> TYPE: DNA
<213> ORGANISM: Artificial
<220> FEATURE:
<223> OTHER INFORMATION: Synthetic primer

<400> SEQUENCE: 11
cacctcagag ccgctaag                                                 18

<210> SEQ ID NO 12
<211> LENGTH: 20
<212> TYPE: DNA
<213> ORGANISM: Artificial
<220> FEATURE:
<223> OTHER INFORMATION: Synthetic primer

<400> SEQUENCE: 12
gctatccagg ctgtgctatc                                               20

<210> SEQ ID NO 13
<211> LENGTH: 17
<212> TYPE: DNA
<213> ORGANISM: Artificial
<220> FEATURE:
<223> OTHER INFORMATION: Synthetic primer

<400> SEQUENCE: 13
tgtcacgcac gatttcc                                                  17

<210> SEQ ID NO 14
<211> LENGTH: 20
<212> TYPE: DNA
<213> ORGANISM: Artificial
<220> FEATURE:
<223> OTHER INFORMATION: Synthetic primer

<400> SEQUENCE: 14
tctgcctttg tccctagat                                                20

<210> SEQ ID NO 15
<211> LENGTH: 20
<212> TYPE: DNA
<213> ORGANISM: Artificial
<220> FEATURE:
<223> OTHER INFORMATION: Synthetic primer

<400> SEQUENCE: 15
aaccttcatt ccccaggact                                               20

<210> SEQ ID NO 16
<211> LENGTH: 16
<212> TYPE: DNA
<213> ORGANISM: Artificial
<220> FEATURE:
<223> OTHER INFORMATION: Synthetic primer

<400> SEQUENCE: 16
gcacgccaat agaagg                                                   16
```

<210> SEQ ID NO 17
<211> LENGTH: 17
<212> TYPE: DNA
<213> ORGANISM: Artificial
<220> FEATURE:
<223> OTHER INFORMATION: Synthetic primer

<400> SEQUENCE: 17
gtaaacggca tggcatc                                                    17

<210> SEQ ID NO 18
<211> LENGTH: 17
<212> TYPE: DNA
<213> ORGANISM: Artificial
<220> FEATURE:
<223> OTHER INFORMATION: Synthetic primer

<400> SEQUENCE: 18
catccagtct cggattg                                                    17

<210> SEQ ID NO 19
<211> LENGTH: 19
<212> TYPE: DNA
<213> ORGANISM: Artificial
<220> FEATURE:
<223> OTHER INFORMATION: Synthetic primer

<400> SEQUENCE: 19
ctcatattgt agagcgggt                                                  19

<210> SEQ ID NO 20
<211> LENGTH: 20
<212> TYPE: DNA
<213> ORGANISM: Artificial
<220> FEATURE:
<223> OTHER INFORMATION: Synthetic primer

<400> SEQUENCE: 20
cagggcttct cattccactc                                                 20

<210> SEQ ID NO 21
<211> LENGTH: 25
<212> TYPE: DNA
<213> ORGANISM: Artificial
<220> FEATURE:
<223> OTHER INFORMATION: Synthetic primer

<400> SEQUENCE: 21
ccatcatatt caactcaaca actgg                                           25

<210> SEQ ID NO 22
<211> LENGTH: 20
<212> TYPE: DNA
<213> ORGANISM: Artificial
<220> FEATURE:
<223> OTHER INFORMATION: Synthetic primer

<400> SEQUENCE: 22
attggcagag cagtttctcc                                                 20

<210> SEQ ID NO 23
<211> LENGTH: 21
<212> TYPE: DNA
<213> ORGANISM: Artificial
<220> FEATURE:

-continued

```
<223> OTHER INFORMATION: Synthetic primer

<400> SEQUENCE: 23
gagctgtatc tgcaggttcg t                                              21

<210> SEQ ID NO 24
<211> LENGTH: 20
<212> TYPE: DNA
<213> ORGANISM: Artificial
<220> FEATURE:
<223> OTHER INFORMATION: Synthetic primer

<400> SEQUENCE: 24
gctatccagg ctgtgctatc                                                20

<210> SEQ ID NO 25
<211> LENGTH: 17
<212> TYPE: DNA
<213> ORGANISM: Artificial
<220> FEATURE:
<223> OTHER INFORMATION: Synthetic primer

<400> SEQUENCE: 25
tgtcacgcac gatttcc                                                   17

<210> SEQ ID NO 26
<211> LENGTH: 21
<212> TYPE: RNA
<213> ORGANISM: Artificial
<220> FEATURE:
<223> OTHER INFORMATION: Synthetic shRNA

<400> SEQUENCE: 26
aagcgaccag gauuauauuc u                                              21
```